(12) United States Patent
Schutt et al.

(10) Patent No.: US 9,724,302 B2
(45) Date of Patent: Aug. 8, 2017

(54) METHOD FOR FORMULATING LARGE DIAMETER SYNTHETIC MEMBRANE VESICLES

(71) Applicant: Pacira Pharmaceuticals, Inc., San Diego, CA (US)

(72) Inventors: Ernest George Schutt, San Diego, CA (US); Ronald Warren McGuire, Murrieta, CA (US); Peter Andrew Walters, San Diego, CA (US); Kathleen D. A. Los, San Diego, CA (US)

(73) Assignee: Pacira Pharmaceuticals, Inc., San Diego, CA (US)

( * ) Notice: Subject to any disclaimer, the term of this patent is extended or adjusted under 35 U.S.C. 154(b) by 731 days.

(21) Appl. No.: 13/786,378

(22) Filed: Mar. 5, 2013

(65) Prior Publication Data
US 2013/0177635 A1 Jul. 11, 2013

Related U.S. Application Data

(63) Continuation of application No. 13/083,485, filed on Apr. 8, 2011.
(Continued)

(51) Int. Cl.
*B01D 11/04* (2006.01)
*B01D 15/00* (2006.01)
(Continued)

(52) U.S. Cl.
CPC ............ *A61K 9/1271* (2013.01); *A61K 9/127* (2013.01); *A61K 9/1277* (2013.01);
(Continued)

(58) Field of Classification Search
CPC ............ A61L 2/022; B01D 39/00; C02F 1/00
(Continued)

(56) References Cited

U.S. PATENT DOCUMENTS

| | | | |
|---|---|---|---|
| 2,044,296 | A | 6/1936 | Hardgrove |
| 2,824,807 | A | 2/1958 | Laster et al. |

(Continued)

FOREIGN PATENT DOCUMENTS

| | | |
|---|---|---|
| AU | 2002301268 B2 | 2/2003 |
| AU | 2006200044 A1 | 2/2006 |

(Continued)

OTHER PUBLICATIONS

Supplementary European Search Report, EP Application No. 11766849.1 (mailed May 7, 2015).
(Continued)

*Primary Examiner* — Monzer R Chorbaji
(74) *Attorney, Agent, or Firm* — Knobbe Martens Olson & Bear LLP

(57) ABSTRACT

The present invention generally relates to the field of pharmaceutical sciences. More specifically, the present invention includes apparatus and devices for the preparation of pharmaceutical formulations containing large diameter synthetic membrane vesicles, such as multivesicular liposomes, methods for preparing such formulations, and the use of specific formulations for therapeutic treatment of subjects in need thereof. Formation and use of the pharmaceutical formulations containing large diameter synthetic membrane vesicles produced by using the apparatus and devices for therapeutic treatment of subjects in need thereof is also contemplated.

19 Claims, 19 Drawing Sheets

Related U.S. Application Data

(60) Provisional application No. 61/322,814, filed on Apr. 9, 2010.

(51) Int. Cl.
| | | |
|---|---|---|
| *B01D 24/00* | (2006.01) | |
| *A61K 9/127* | (2006.01) | |
| *B01D 1/16* | (2006.01) | |
| *A61K 31/4458* | (2006.01) | |
| *B01F 3/08* | (2006.01) | |
| *B01F 5/10* | (2006.01) | |
| *B01F 7/00* | (2006.01) | |
| *A61K 9/48* | (2006.01) | |
| *A61M 11/00* | (2006.01) | |
| *B01J 13/04* | (2006.01) | |
| *B01J 13/12* | (2006.01) | |
| *A61K 31/445* | (2006.01) | |
| *B01F 3/04* | (2006.01) | |
| *B01F 15/06* | (2006.01) | |

(52) U.S. Cl.
CPC .......... *A61K 9/4833* (2013.01); *A61K 31/445* (2013.01); *A61K 31/4458* (2013.01); *A61M 11/00* (2013.01); *B01D 1/16* (2013.01); *B01F 3/04049* (2013.01); *B01F 3/0807* (2013.01); *B01F 3/088* (2013.01); *B01F 5/104* (2013.01); *B01F 7/0075* (2013.01); *B01F 15/065* (2013.01); *B01J 13/043* (2013.01); *B01J 13/125* (2013.01); *B01F 2015/061* (2013.01); *B01F 2215/0032* (2013.01)

(58) Field of Classification Search
USPC ......... 422/255, 256; 210/634, 807, 263, 348
See application file for complete search history.

(56) References Cited

U.S. PATENT DOCUMENTS

| | | |
|---|---|---|
| 3,028,623 A | 4/1962 | Labino |
| 3,202,533 A | 8/1965 | Sachsel |
| 3,272,441 A | 9/1966 | Davis et al. |
| 3,275,063 A | 9/1966 | Tailor |
| 3,301,829 A | 1/1967 | Woodward et al. |
| 3,310,240 A | 3/1967 | Grundman |
| 3,340,334 A | 9/1967 | Feldmann et al. |
| 3,371,869 A | 3/1968 | Hughes |
| 3,408,007 A | 10/1968 | Raichle et al. |
| 3,421,693 A | 1/1969 | Fraser |
| 3,531,465 A | 9/1970 | Bridgeford |
| 3,533,558 A | 10/1970 | Masters |
| 3,539,463 A | 11/1970 | Harper |
| 3,547,695 A | 12/1970 | Agazarian |
| 3,595,926 A | 7/1971 | Mann et al. |
| 3,607,023 A | 9/1971 | Palm |
| 3,615,663 A | 10/1971 | Becker |
| 3,615,722 A | 10/1971 | Kurtz et al. |
| 3,630,775 A | 12/1971 | Winkler |
| 3,635,837 A | 1/1972 | Robson |
| 3,644,305 A | 2/1972 | Frisque et al. |
| 3,661,514 A | 5/1972 | Herink |
| 3,663,666 A | 5/1972 | Vincent |
| 3,664,963 A | 5/1972 | Pasin |
| 3,666,484 A | 5/1972 | Gurkin et al. |
| 3,674,555 A | 7/1972 | Meyer et al. |
| 3,674,557 A | 7/1972 | Gray |
| 3,677,896 A | 7/1972 | Kurimoto et al. |
| 3,684,186 A | 8/1972 | Helmrich |
| 3,696,520 A | 10/1972 | Niedner et al. |
| 3,702,252 A | 11/1972 | Veltman et al. |
| 3,706,599 A | 12/1972 | Woodruff et al. |
| 3,708,307 A | 1/1973 | Lundstedt |
| 3,738,412 A | 6/1973 | Nezbed et al. |
| 3,738,938 A | 6/1973 | Barrett |
| 3,741,273 A | 6/1973 | Meade |
| 3,746,657 A | 7/1973 | Miller et al. |
| 3,749,671 A | 7/1973 | Gedge |
| 3,751,398 A | 8/1973 | Dahl |
| 3,756,831 A | 9/1973 | Wingerd et al. |
| 3,759,450 A | 9/1973 | Fram et al. |
| 3,761,288 A | 9/1973 | Glicksman et al. |
| 3,764,346 A | 10/1973 | Noznick et al. |
| 3,770,207 A | 11/1973 | Muller et al. |
| 3,776,688 A | 12/1973 | Damgaard-Iversen et al. |
| 3,784,648 A | 1/1974 | Bergmeister et al. |
| 3,793,465 A | 2/1974 | Bohren |
| 3,803,111 A | 4/1974 | Munro et al. |
| 3,803,723 A | 4/1974 | Lamm et al. |
| 3,805,869 A | 4/1974 | Winter et al. |
| 3,821,434 A | 6/1974 | Houghton-Larsen et al. |
| 3,830,750 A | 8/1974 | Wellman |
| 3,840,996 A | 10/1974 | Grindstaff et al. |
| 3,843,380 A | 10/1974 | Beyn |
| 3,845,801 A | 11/1974 | Kuchar |
| 3,858,854 A | 1/1975 | Win et al. |
| 3,883,494 A | 5/1975 | Winter et al. |
| 3,885,918 A | 5/1975 | Isahaya |
| 3,920,187 A | 11/1975 | Willis |
| 3,923,248 A | 12/1975 | Creswell |
| 3,923,680 A | 12/1975 | Roeder et al. |
| 3,932,587 A | 1/1976 | Grantham et al. |
| 3,949,094 A | 4/1976 | Johnson et al. |
| 3,956,009 A | 5/1976 | Lundquist, Jr. et al. |
| 3,956,521 A | 5/1976 | Pisecky et al. |
| 3,959,517 A | 5/1976 | Niki et al. |
| 3,960,583 A | 6/1976 | Netting et al. |
| 3,962,468 A | 6/1976 | Pischke et al. |
| 3,971,852 A | 7/1976 | Brenner et al. |
| 3,973,053 A | 8/1976 | Galusky et al. |
| 3,980,233 A | 9/1976 | Simmons et al. |
| 3,985,913 A | 10/1976 | Johnson et al. |
| 3,989,446 A | 11/1976 | Grill et al. |
| 3,992,314 A | 11/1976 | Cherney |
| 3,993,536 A | 11/1976 | Kalka et al. |
| 3,993,713 A | 11/1976 | van Brederode et al. |
| 3,995,070 A | 11/1976 | Nagasawa et al. |
| 4,002,524 A | 1/1977 | Damgaard-Iversen et al. |
| 4,002,706 A | 1/1977 | Pretorius |
| 4,011,661 A | 3/1977 | Sezaki et al. |
| 4,012,461 A | 3/1977 | van Brederode |
| 4,020,564 A | 5/1977 | Bayliss |
| 4,028,447 A | 6/1977 | Talbert |
| 4,031,174 A | 6/1977 | Bennett |
| 4,036,891 A | 7/1977 | Moller et al. |
| 4,042,653 A | 8/1977 | Beyn |
| 4,054,541 A | 10/1977 | Mausner et al. |
| 4,087,050 A | 5/1978 | Tsuji et al. |
| 4,088,791 A | 5/1978 | Jones |
| 4,109,998 A | 8/1978 | Iverson |
| 4,133,947 A | 1/1979 | Kalka et al. |
| 4,134,719 A | 1/1979 | Velie |
| 4,162,926 A | 7/1979 | Veltman et al. |
| 4,169,556 A | 10/1979 | Muller |
| 4,182,871 A | 1/1980 | Moller |
| 4,187,323 A | 2/1980 | Gidlow |
| 4,187,617 A | 2/1980 | Becker, Jr. et al. |
| 4,211,604 A | 7/1980 | Muschelknautz et al. |
| 4,216,025 A | 8/1980 | Monti |
| 4,226,668 A | 10/1980 | Ferguson |
| 4,233,114 A | 11/1980 | Gastaldi |
| 4,246,039 A | 1/1981 | Mixon, Jr. |
| 4,261,793 A | 4/1981 | Nakamura et al. |
| 4,263,012 A | 4/1981 | Leszczynska et al. |
| 4,284,242 A | 8/1981 | Randell |
| 4,299,501 A | 11/1981 | Patil et al. |
| 4,352,717 A | 10/1982 | Watanabe et al. |
| 4,368,100 A | 1/1983 | Pyves et al. |
| 4,420,442 A | 12/1983 | Sands |
| 4,443,228 A | 4/1984 | Schlinger |
| 4,504,451 A | 3/1985 | Quee et al. |
| 4,508,703 A | 4/1985 | Redziniak et al. |
| 4,510,066 A | 4/1985 | Saar |

(56) References Cited

U.S. PATENT DOCUMENTS

| | | | |
|---|---|---|---|
| 4,515,900 A | 5/1985 | Hettinger, Jr. et al. |
| 4,517,214 A | 5/1985 | Shoaf et al. |
| 4,524,016 A | 6/1985 | Ferretti |
| 4,536,377 A | 8/1985 | Shimp |
| 4,540,629 A | 9/1985 | Sands et al. |
| 4,541,873 A | 9/1985 | Schenz et al. |
| 4,547,468 A | 10/1985 | Jones et al. |
| 4,548,822 A | 10/1985 | Schmidt |
| 4,551,436 A | 11/1985 | Johnson et al. |
| 4,590,090 A | 5/1986 | Siemers et al. |
| 4,590,142 A | 5/1986 | Yamazaki et al. |
| 4,594,075 A | 6/1986 | Schenkenberger |
| 4,595,418 A | 6/1986 | Yoshino |
| 4,600,579 A | 7/1986 | Salpekar et al. |
| 4,605,666 A | 8/1986 | Schmidt et al. |
| 4,610,760 A | 9/1986 | Kirkpatrick et al. |
| 4,612,370 A | 9/1986 | Hunt |
| 4,614,827 A | 9/1986 | Arndt et al. |
| 4,623,523 A | 11/1986 | Abrams et al. |
| 4,624,678 A | 11/1986 | Schneider |
| 4,631,284 A | 12/1986 | Salpekar et al. |
| 4,636,336 A | 1/1987 | Gay et al. |
| 4,638,029 A | 1/1987 | Meschke et al. |
| 4,640,825 A | 2/1987 | Rosenberg |
| 4,642,904 A | 2/1987 | Smith, Jr. |
| 4,652,391 A | 3/1987 | Balk |
| 4,652,411 A | 3/1987 | Swarr et al. |
| 4,655,941 A | 4/1987 | Suzuki |
| 4,656,019 A | 4/1987 | Hensler et al. |
| 4,659,583 A | 4/1987 | Hashimoto et al. |
| 4,661,281 A | 4/1987 | Seiter et al. |
| 4,681,697 A | 7/1987 | Doetsch et al. |
| 4,681,748 A | 7/1987 | Doetsch et al. |
| 4,681,759 A | 7/1987 | Porubcan |
| 4,683,073 A | 7/1987 | Diehl |
| 4,684,519 A | 8/1987 | Barabas |
| 4,695,466 A | 9/1987 | Morishita et al. |
| 4,695,475 A | 9/1987 | Zwiercan et al. |
| 4,704,416 A | 11/1987 | Eck et al. |
| 4,710,519 A | 12/1987 | Finnan et al. |
| 4,717,557 A | 1/1988 | Kowalski et al. |
| 4,720,910 A | 1/1988 | Rourke et al. |
| 4,721,608 A | 1/1988 | Kowalski et al. |
| 4,724,121 A | 2/1988 | Weyand |
| 4,728,704 A | 3/1988 | Chadwick et al. |
| 4,734,401 A | 3/1988 | Blouin |
| 4,737,411 A | 4/1988 | Graves, Jr. et al. |
| 4,741,624 A | 5/1988 | Barroyer |
| 4,746,440 A | 5/1988 | Seeger |
| 4,760,956 A | 8/1988 | Mansfield |
| 4,762,532 A | 8/1988 | Lipp |
| 4,774,012 A | 9/1988 | Ishikawa et al. |
| 4,774,271 A | 9/1988 | Lindner et al. |
| 4,781,852 A | 11/1988 | Kaczur et al. |
| 4,794,010 A | 12/1988 | Jones et al. |
| 4,806,165 A | 2/1989 | Band et al. |
| 4,812,295 A | 3/1989 | Bresowar |
| 4,830,859 A | 5/1989 | Finnan et al. |
| 4,831,015 A | 5/1989 | Waite |
| 4,835,186 A | 5/1989 | Reuter et al. |
| 4,835,187 A | 5/1989 | Reuter et al. |
| 4,835,188 A | 5/1989 | Ho et al. |
| 4,844,734 A | 7/1989 | Iwasaki et al. |
| 4,846,402 A | 7/1989 | Sandell et al. |
| 4,846,666 A | 7/1989 | Bilawa et al. |
| 4,847,371 A | 7/1989 | Schara et al. |
| 4,849,201 A | 7/1989 | Smith et al. |
| 4,863,521 A | 9/1989 | Block |
| 4,865,773 A | 9/1989 | Kim et al. |
| 4,867,986 A | 9/1989 | Desai et al. |
| 4,871,398 A | 10/1989 | Katcher et al. |
| 4,871,574 A | 10/1989 | Yamazaki et al. |
| 4,877,514 A | 10/1989 | Hettinger et al. |
| 4,882,994 A | 11/1989 | Veltman et al. |
| 4,888,161 A | 12/1989 | Adams, Jr. et al. |
| 4,891,527 A | 1/1990 | Rabatin |
| 4,898,739 A | 2/1990 | Subramaniam et al. |
| 4,915,509 A | 4/1990 | Sauer et al. |
| 4,921,705 A | 5/1990 | Arai et al. |
| 4,933,192 A | 6/1990 | Darling et al. |
| 4,948,773 A | 8/1990 | Ito |
| 4,963,226 A | 10/1990 | Chamberlain |
| 5,204,112 A | 4/1993 | Hope et al. |
| 5,277,023 A | 1/1994 | Bradley et al. |
| 5,294,298 A | 3/1994 | Maesaka et al. |
| 5,329,760 A | 7/1994 | Bradley et al. |
| 5,362,564 A | 11/1994 | Suzuki et al. |
| 5,417,054 A | 5/1995 | Lee et al. |
| 5,505,045 A | 4/1996 | Lee et al. |
| 5,554,382 A | 9/1996 | Castor |
| 5,571,281 A | 11/1996 | Allen |
| 5,576,017 A | 11/1996 | Kim |
| 5,656,491 A * | 8/1997 | Cassani .................. B01J 19/004 422/129 |
| 5,723,147 A | 3/1998 | Kim et al. |
| 5,766,627 A | 6/1998 | Sankaram et al. |
| 5,807,572 A | 9/1998 | Kim et al. |
| 5,945,126 A | 8/1999 | Thanoo et al. |
| 5,948,441 A | 9/1999 | Lenk et al. |
| 6,021,635 A | 2/2000 | Gaag et al. |
| 6,045,824 A | 4/2000 | Kim et al. |
| 6,071,534 A | 6/2000 | Kim et al. |
| 6,116,171 A | 9/2000 | Oota et al. |
| 6,156,247 A | 12/2000 | Moschini |
| 6,162,462 A | 12/2000 | Bolotin et al. |
| 6,270,802 B1 | 8/2001 | Thanoo et al. |
| 6,305,833 B1 | 10/2001 | Horn et al. |
| 6,367,960 B2 | 4/2002 | Yamazaki et al. |
| 6,386,751 B1 | 5/2002 | Wootan et al. |
| 6,554,467 B2 | 4/2003 | Snyder et al. |
| 6,568,842 B1 | 5/2003 | Murray |
| 6,596,172 B1 | 7/2003 | Kopf |
| 6,729,561 B2 | 5/2004 | Hirae et al. |
| 6,921,458 B2 | 7/2005 | Chickering, III |
| 7,348,031 B2 | 3/2008 | Montasser et al. |
| 7,434,401 B2 | 10/2008 | Hayashi |
| 7,468,151 B2 | 12/2008 | van Buitenen et al. |
| 7,628,893 B1 | 12/2009 | Bonser et al. |
| 8,182,835 B2 | 5/2012 | Kim et al. |
| 8,795,602 B2 | 8/2014 | Ergut |
| 9,545,604 B2 | 1/2017 | Pan |
| 2002/0009466 A1 | 1/2002 | Brayden |
| 2002/0039596 A1 | 4/2002 | Hartounian et al. |
| 2002/0170859 A1* | 11/2002 | Kopf .................. B01D 15/361 210/635 |
| 2002/0190404 A1 | 12/2002 | Baarda |
| 2003/0024526 A1 | 2/2003 | Ganan-Calvo |
| 2003/0060559 A1 | 3/2003 | Oliviere et al. |
| 2003/0185893 A1 | 10/2003 | Beyerinck et al. |
| 2003/0215515 A1 | 11/2003 | Truong-Le et al. |
| 2004/0005996 A1 | 1/2004 | Muir et al. |
| 2004/0145069 A1 | 7/2004 | Low |
| 2005/0117447 A1 | 6/2005 | Moore et al. |
| 2006/0002862 A1 | 1/2006 | Truong-Le et al. |
| 2006/0071357 A1 | 4/2006 | Pilon et al. |
| 2007/0084340 A1 | 4/2007 | Dou |
| 2007/0205303 A1 | 9/2007 | Nayak et al. |
| 2007/0235889 A1 | 10/2007 | Hartounian et al. |
| 2008/0075670 A1 | 3/2008 | Eilat |
| 2009/0005521 A1 | 1/2009 | Hassan et al. |
| 2009/0017108 A1 | 1/2009 | Yuzhakov |
| 2009/0131543 A1 | 5/2009 | Weitz et al. |
| 2009/0141584 A1 | 6/2009 | Boer et al. |
| 2009/0252836 A1 | 10/2009 | Hashiba |
| 2009/0281211 A1 | 11/2009 | Van Der Huizen et al. |
| 2009/0312872 A1 | 12/2009 | Burris et al. |
| 2010/0168298 A1 | 7/2010 | Kao et al. |
| 2011/0250264 A1 | 10/2011 | Schutt et al. |
| 2011/0260347 A1 | 10/2011 | Grebennikov |
| 2013/0177633 A1 | 7/2013 | Schutt et al. |
| 2013/0177634 A1 | 7/2013 | Schutt et al. |
| 2013/0177636 A1 | 7/2013 | Schutt et al. |
| 2013/0177637 A1 | 7/2013 | Schutt et al. |
| 2013/0177638 A1 | 7/2013 | Schutt et al. |

(56) References Cited

U.S. PATENT DOCUMENTS

| | | |
|---|---|---|
| 2013/0183372 A1 | 7/2013 | Schutt et al. |
| 2013/0183373 A1 | 7/2013 | Schutt et al. |
| 2013/0183375 A1 | 7/2013 | Schutt et al. |
| 2013/0195965 A1 | 8/2013 | Schutt et al. |
| 2013/0306759 A1 | 11/2013 | Schutt et al. |
| 2016/0361260 A1 | 12/2016 | Schutt et al. |

FOREIGN PATENT DOCUMENTS

| | | |
|---|---|---|
| CA | 933796 | 9/1973 |
| CA | 960811 | 1/1975 |
| CA | 2 564 120 A1 | 8/1998 |
| CA | 2464668 | 5/2003 |
| CH | 519936 | 7/1971 |
| CH | 587023 | 7/1974 |
| CN | 1627985 | 6/2005 |
| CN | 101395207 | 3/2009 |
| CN | 101396345 | 5/2009 |
| CN | 101679143 | 3/2010 |
| DE | 1199191 | 8/1965 |
| DE | 51254 | 10/1966 |
| DE | 56223 | 5/1967 |
| DE | 1903605 | 8/1970 |
| DE | 1458080 | 11/1970 |
| DE | 1767545 | 3/1972 |
| DE | 1617160 | 4/1972 |
| DE | 2118248 | 11/1972 |
| DE | 2121066 | 11/1972 |
| DE | 2142425 | 3/1973 |
| DE | 2209565 | 9/1973 |
| DE | 2214410 | 10/1973 |
| DE | 2300763 | 8/1974 |
| DE | 2426389 | 1/1975 |
| DE | 2518848 | 11/1975 |
| DE | 2553141 | 6/1976 |
| DE | 2605052 A1 | 8/1976 |
| DE | 2649088 A1 | 10/1976 |
| DE | 2519655 | 11/1976 |
| DE | 2711761 A1 | 9/1977 |
| DE | 2614261 A1 | 10/1977 |
| DE | 2713951 | 10/1977 |
| DE | 2656418 | 11/1977 |
| DE | 2719306 A1 | 12/1977 |
| DE | 2746489 | 4/1979 |
| DE | 219039 A3 | 2/1985 |
| DE | 3523988 A1 | 1/1986 |
| DE | 3537480 A1 | 4/1987 |
| DE | 3539631 | 5/1987 |
| DE | 3630577 A1 | 3/1988 |
| DE | 256708 A1 | 5/1988 |
| DE | 261162 A1 | 10/1988 |
| DE | 275583 | 1/1990 |
| DE | 197 50 679 A1 | 5/1999 |
| EP | 0 116 311 A1 | 8/1984 |
| EP | 0138410 B1 | 4/1985 |
| EP | 0141509 | 5/1985 |
| EP | 0143576 | 6/1985 |
| EP | 0154189 A2 | 9/1985 |
| EP | 0173069 | 3/1986 |
| EP | 0175799 A1 | 4/1986 |
| EP | 0199930 | 11/1986 |
| EP | 0209510 | 1/1987 |
| EP | 0237353 | 9/1987 |
| EP | 0242831 | 10/1987 |
| EP | 0252374 | 1/1988 |
| EP | 0260971 | 3/1988 |
| EP | 0273688 | 7/1988 |
| EP | 0274053 | 7/1988 |
| EP | 0277730 | 8/1988 |
| EP | 0279818 | 8/1988 |
| EP | 0280503 A2 | 8/1988 |
| EP | 0282747 | 9/1988 |
| EP | 0284186 | 9/1988 |
| EP | 0289311 | 11/1988 |
| EP | 0289312 | 11/1988 |
| EP | 0295389 | 12/1988 |
| EP | 0223718 | 1/1989 |
| EP | 0305042 | 3/1989 |
| EP | 0309322 | 3/1989 |
| EP | 0314987 | 5/1989 |
| EP | 032043 | 6/1989 |
| EP | 0323129 | 7/1989 |
| EP | 0337779 | 10/1989 |
| EP | 0338799 | 10/1989 |
| EP | 0341383 | 11/1989 |
| EP | 0345576 | 12/1989 |
| EP | 0345717 | 12/1989 |
| EP | 0345765 | 12/1989 |
| EP | 0354609 | 2/1990 |
| EP | 0358951 | 3/1990 |
| EP | 0366303 B1 | 5/1990 |
| EP | 0366898 | 5/1990 |
| EP | 0369339 A2 | 5/1990 |
| EP | 0371211 A2 | 6/1990 |
| EP | 0371329 | 6/1990 |
| EP | 0376863 A2 | 7/1990 |
| EP | 0384603 | 8/1990 |
| EP | 1 306 127 | 12/2007 |
| EP | 1 920 765 | 5/2008 |
| EP | 2 008 710 | 12/2008 |
| ES | 8505618 | 8/1981 |
| FR | 2226892 | 11/1974 |
| FR | 2586256 A1 | 6/1985 |
| GB | 980062 | 1/1965 |
| GB | 995656 | 6/1965 |
| GB | 1122660 | 8/1968 |
| GB | 1124578 | 8/1968 |
| GB | 1128924 | 10/1968 |
| GB | 1233479 | 5/1971 |
| GB | 1243002 | 8/1971 |
| GB | 1249195 | 10/1971 |
| GB | 1252651 | 11/1971 |
| GB | 1265005 | 3/1972 |
| GB | 1272757 | 5/1972 |
| GB | 1276821 | 6/1972 |
| GB | 1280184 | 7/1972 |
| GB | 1281653 | 7/1972 |
| GB | 1282356 | 7/1972 |
| GB | 1299205 | 12/1972 |
| GB | 1299839 | 12/1972 |
| GB | 1301796 | 1/1973 |
| GB | 1315882 | 5/1973 |
| GB | 1316896 | 5/1973 |
| GB | 1324116 | 7/1973 |
| GB | 1327064 | 8/1973 |
| GB | 1336577 | 11/1973 |
| GB | 1338033 | 11/1973 |
| GB | 1363414 | 8/1974 |
| GB | 1363419 | 8/1974 |
| GB | 1373317 | 11/1974 |
| GB | 1390032 | 4/1975 |
| GB | 1412133 | 10/1975 |
| GB | 1412790 | 11/1975 |
| GB | 1412890 | 11/1975 |
| GB | 1422781 | 1/1976 |
| GB | 1424916 | 2/1976 |
| GB | 1449889 | 9/1976 |
| GB | 1458039 | 12/1976 |
| GB | 1458316 | 12/1976 |
| GB | 1474807 | 5/1977 |
| GB | 1477379 | 6/1977 |
| GB | 1479896 | 7/1977 |
| GB | 1482695 | 8/1977 |
| GB | 1488250 | 10/1977 |
| GB | 1491289 | 11/1977 |
| GB | 1492992 | 11/1977 |
| GB | 1525803 | 9/1978 |
| GB | 1525864 | 9/1978 |
| GB | 1553801 | 10/1978 |
| GB | 1536196 | 12/1978 |
| GB | 1556422 | 11/1979 |
| GB | 2022394 A | 12/1979 |
| GB | 1563365 | 3/1980 |
| GB | 2153381 A | 8/1985 |

(56) References Cited

FOREIGN PATENT DOCUMENTS

| | | |
|---|---|---|
| GB | 2157939 | 11/1985 |
| GB | 2160423 A | 12/1985 |
| GB | 2172006 A | 9/1986 |
| GB | 2177283 | 1/1987 |
| GB | 2178045 | 2/1987 |
| GB | 2184716 | 7/1987 |
| GB | 2206601 A | 1/1989 |
| JP | 51-008176 | 1/1976 |
| JP | 58-022062 | 2/1983 |
| JP | 60210949 | 10/1985 |
| JP | 60244288 | 12/1985 |
| JP | 61149067 | 7/1986 |
| JP | 62079841 | 4/1987 |
| JP | 62083316 | 4/1987 |
| JP | 62-201635 | 9/1987 |
| JP | 62275014 | 11/1987 |
| JP | 63022502 | 1/1988 |
| JP | 63035503 | 2/1988 |
| JP | 1132721 | 5/1989 |
| JP | 1194901 | 8/1989 |
| JP | 1301717 | 12/1989 |
| JP | 2045535 | 2/1990 |
| JP | 06-100353 | 4/1994 |
| NL | 8601185 | 12/1987 |
| SU | 424611 | 4/1974 |
| SU | 541507 | 1/1977 |
| WO | WO 87/07595 | 12/1987 |
| WO | WO 88/01862 | 3/1988 |
| WO | WO 88/09316 | 12/1988 |
| WO | WO 89/05290 | 6/1989 |
| WO | WO 90/03788 | 4/1990 |
| WO | WO 90/03838 | 4/1990 |
| WO | WO 90/09402 | 8/1990 |
| WO | WO 94/27581 | 12/1994 |
| WO | WO 95/01164 | 1/1995 |
| WO | WO 96/08235 A1 | 3/1996 |
| WO | WO 98/33483 A1 | 8/1998 |
| WO | WO 99/12522 A1 | 3/1999 |
| WO | WO 99/12523 A1 | 3/1999 |
| WO | WO 99/13865 A1 | 3/1999 |
| WO | WO 99/25319 A1 | 5/1999 |
| WO | WO 00/09089 | 2/2000 |
| WO | WO 01/03848 A1 | 1/2001 |
| WO | WO 01/68235 A1 | 9/2001 |
| WO | WO 03/035244 | 5/2003 |
| WO | WO 03/051505 | 6/2003 |
| WO | WO 03/089123 A1 | 10/2003 |
| WO | WO 2006/113229 | 10/2006 |
| WO | WO 2007/117023 A1 | 10/2007 |
| WO | WO 2008/055628 A1 | 5/2008 |
| WO | WO 2008/122288 | 10/2008 |
| WO | WO 2009/002967 A2 | 12/2008 |
| WO | WO 2009/003051 | 12/2008 |
| WO | WO 2010/077167 | 7/2010 |

OTHER PUBLICATIONS

Supplementary European Search Report, EP Application No. 14181416.0 (mailed May 19, 2015).
Atiemo-Obeng et al. "Rotor-Stator Mixing Devices", Handbook of Industrial Mixing Science and Practice, 2004, 479-505, Eds. Paul, et al., Hoboken, NJ: John Wiley and Sons, Inc.
Bennington "Mixing in Pulp Bleaching Operations", Handbook of Industrial Mixing Science and Practice, 2004, 1221-1246, Eds. Paul, et al., Hoboken, NJ: John Wiley and Sons, Inc.
Chen et al., "Particle Design Using a 4-Fluid-Nozzle-Spray-Drying Technique for Sustained Release of Acetaminophen", Chem. Pharm. Bull. 2006, 54(7): 948-953.
Legako et al., "Effect of Spray Nozzle Design on Fish Oil-Whey Protein Microcapsule Properties", Journal of Food Science, Aug. 1, 2010, 75(6): E394-400.
Manning, "Batch Emulsification Using an Inline Rotor-Stator in a Recycle Loop of Varying Volume" M.Sc Dissertation submitted to the University of Manchester, 2009, 100 pages.
Masters, "The Process Stages of Spray Drying", Spray Drying Handbook, 1991, 250-265, 5th Ed., Harlow Essex, England: Longman Scientific and Technical.
Park et al., "pH-Responsive Hydrogels From Moldable Composite Microparticles Prepared by Coaxial Electro-Spray Drying", Chemical Engineering Journal, May 1, 2011, 169: 348-357.
Wang et al., "Isoxyl Aerosols for Tuberculosis Treatment: Preparation and Characterization of Particles", American Association of Pharmaceutical Scientists, Jun. 2010, 11 (2): 538-549.
International Search Report mailed on Oct. 31, 2011 for International Application No. PCT/US2011/031858, filed Apr. 8, 2011.
Written Opinion mailed on Oct. 31, 2011 for International Application No. PCT/US2011/031858, filed Apr. 8, 2011.
Buchi Labortechnik AG, Nov. 16, 2009, Operation Manual Mini Spray Dryer B-290, 93001en, Version G, 56 pages.
Kawashima et al., Sep. 1991, Shear-Induced Phase Inversion and Size Control of Water/Oil/Water Emulsion Droplets with Porous Membrane, J Coll Inter Science, 145(2):512-523.
U.S. Appl. No. 13/083,485, Method for Formulating Large Diameter Synthetic Membrane Vesicles, filed Apr. 8, 2011.
U.S. Appl. No. 13/786,364, Method for Formulating Large Diameter Synthetic Membrane Vesicles, filed Mar. 5, 2013.
U.S. Appl. No. 13/786,377, Method for Formulating Large Diameter Synthetic Membrane Vesicles, filed Mar. 5, 2013.
U.S. Appl. No. 13/786,371, Method for Formulating Large Diameter Synthetic Membrane Vesicles, filed Mar. 5, 2013.
U.S. Appl. No. 13/786,405, Method for Formulating Large Diameter Synthetic Membrane Vesicles, filed Mar. 5, 2013.
U.S. Appl. No. 13/786,873, Method for Formulating Large Diameter Synthetic Membrane Vesicles, filed Mar. 6, 2013.
U.S. Appl. No. 13/786,945, Method for Formulating Large Diameter Synthetic Membrane Vesicles, filed Mar. 6, 2013.
U.S. Appl. No. 13/787,117, Method for Formulating Large Diameter Synthetic Membrane Vesicles, filed Mar. 6, 2013.
U.S. Appl. No. 13/786,890, Method for Formulating Large Diameter Synthetic Membrane Vesicles. filed Mar. 6, 2013.
U.S. Appl. No. 13/786,933, Method for Formulating Large Diameter Synthetic Membrane Vesicles, filed Mar. 6, 2013.
U.S. Appl. No. 13/791,569, Method for Formulating Large Diameter Synthetic Membrane Vesicles, filed Mar. 8, 2013.
Declaration of William J. Lambert submitted in the Opposition of European Patent No. 1 306 127 B, dated Sep. 9, 2009.
Definition of homogenizer, Chambers Science and Technology Dictionary, 1984.
Fermentation and Biochemical Engineering Handbook, 1997.
Guideline on Sterile Drug Products Produced by Aseptic Processing, Center for Drug Evaluation and Research, Guidance for Industry, Jun. 1987.
Millipore Technical Brief, "Protein Concentration and Diafiltration by Tangential Flow Filtration," 2003.
Silverson In-Line Mixer Product Webpage, downloaded from European Patent Register on Oct. 3, 2016 (Opposition to European Patent No. 1 306 127 B1).
SkyePharma Building Diagram, downloaded from European Patent Register on Oct. 3, 2016 (Opposition to European Patent No. 1 306 127 B1).
File History for Opposition to European Patent No. 1 306 127 B1, published Dec. 26, 2007 (equivalent to U.S. Pat. No. 7,468,151). File history downloaded from European Patent Register on Oct. 3, 2016.
European Search Report, EP Application No. 16194582.9 (dated Mar. 23, 2017).

* cited by examiner

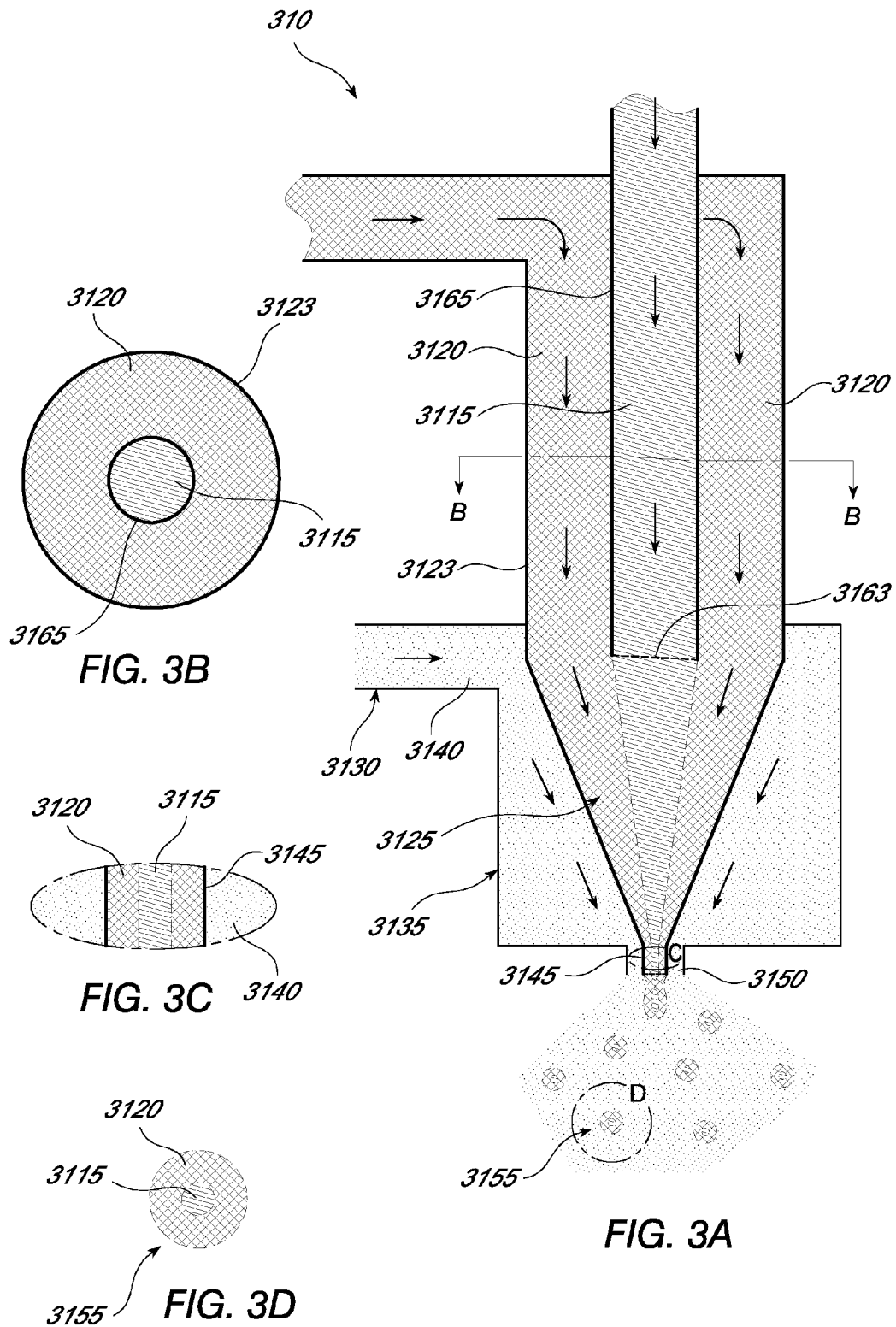

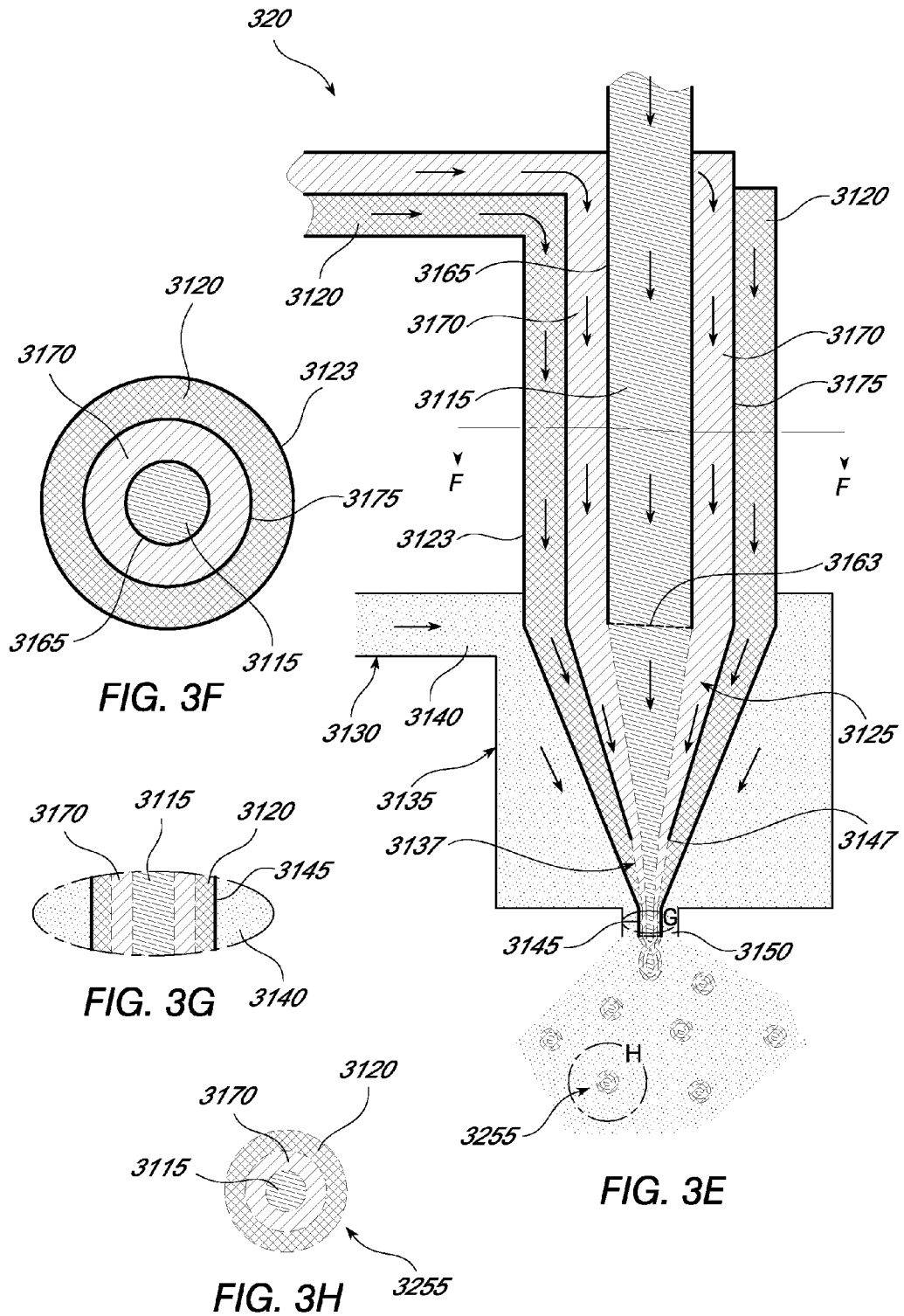

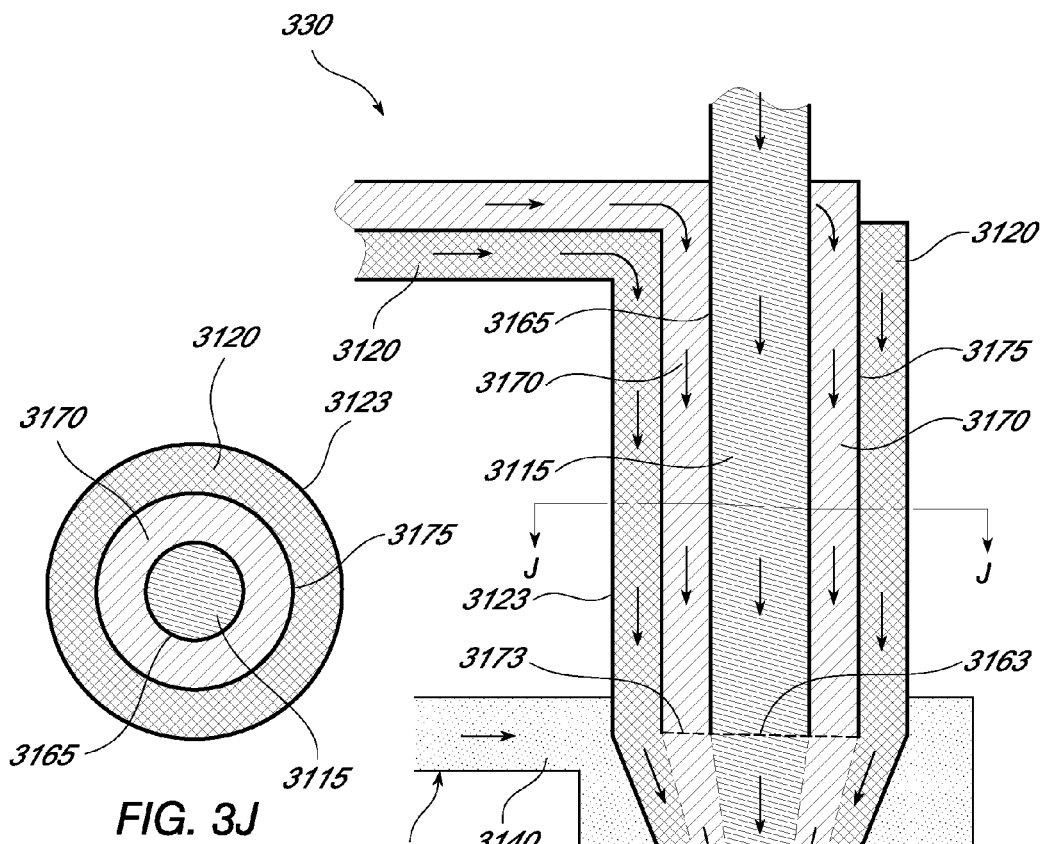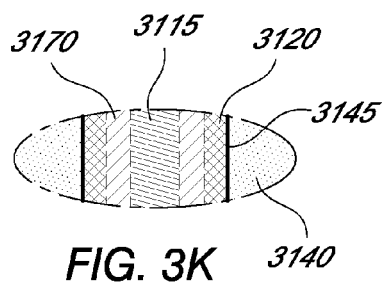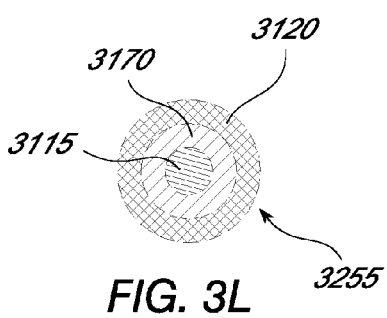

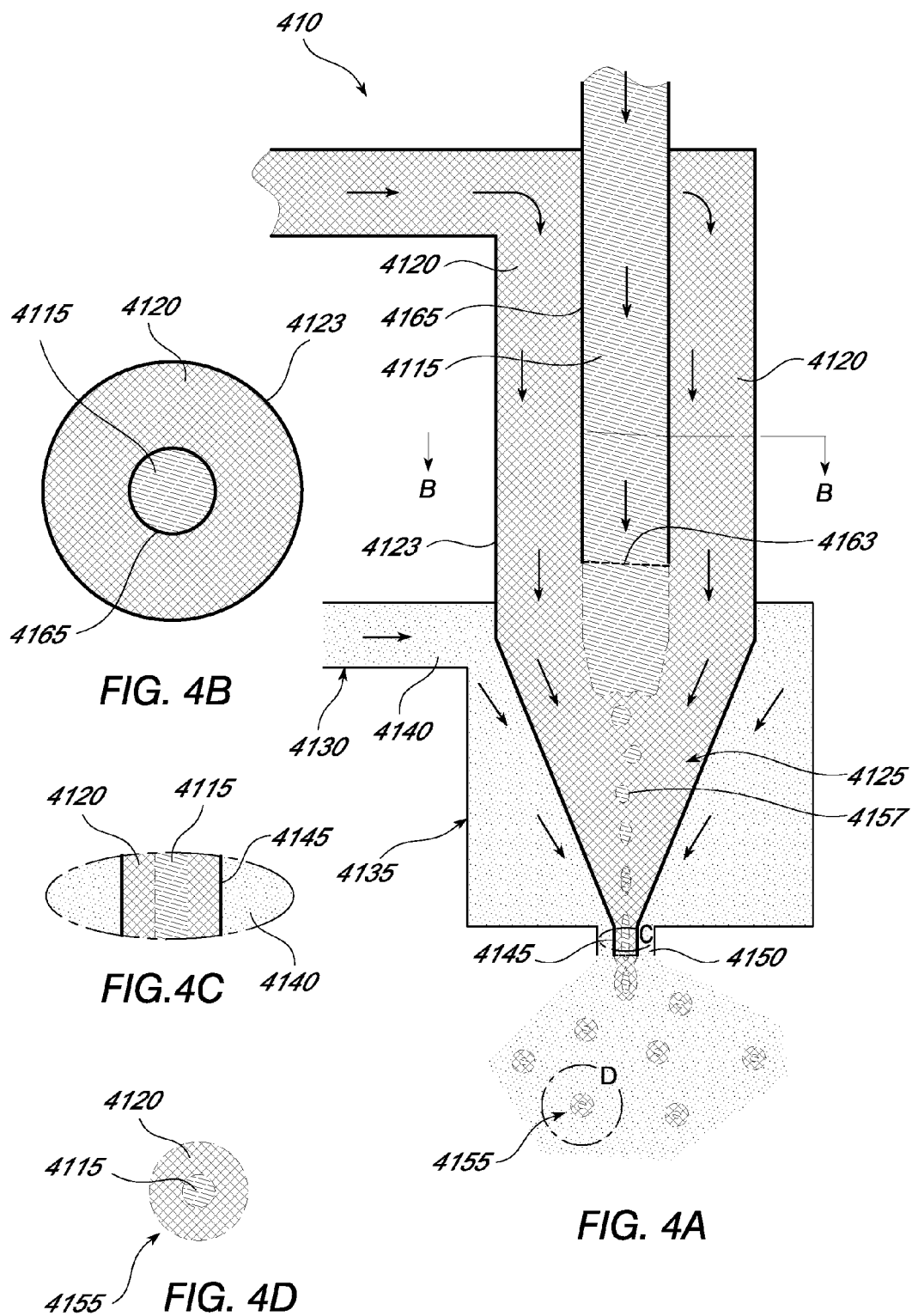

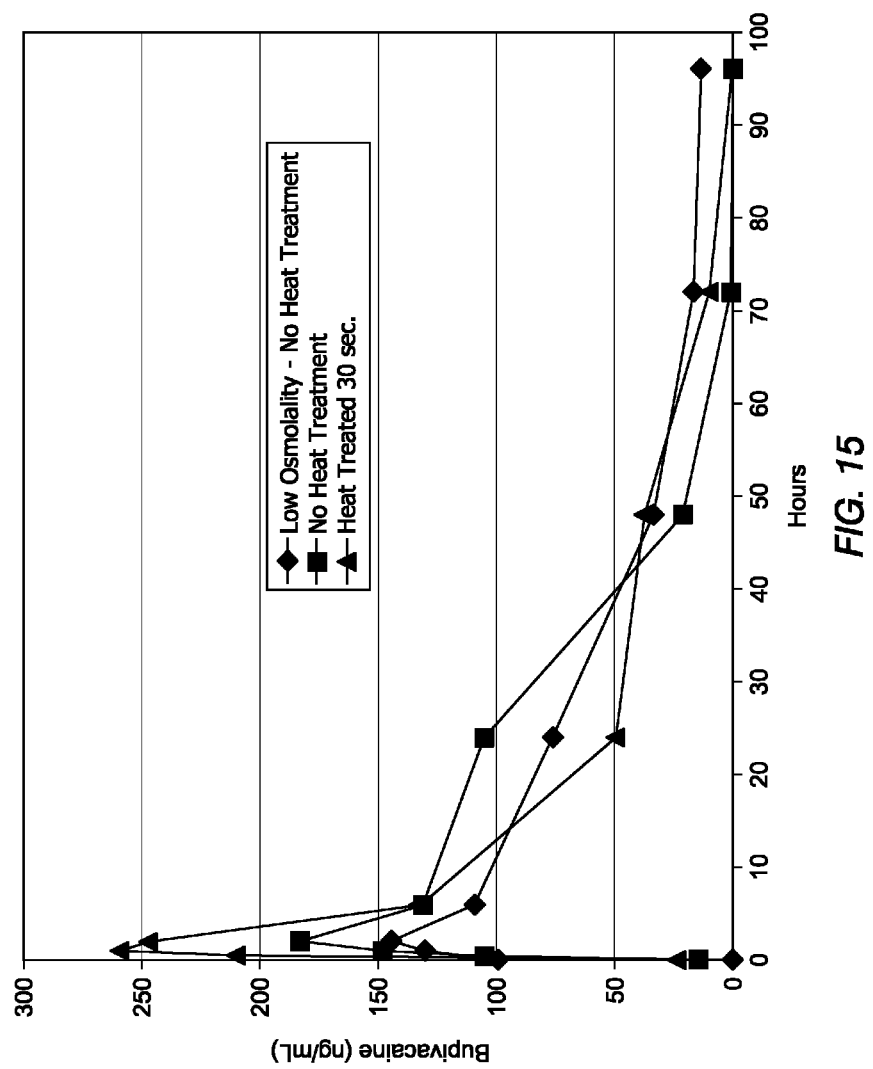

METHOD FOR FORMULATING LARGE DIAMETER SYNTHETIC MEMBRANE VESICLES

INCORPORATION BY REFERENCE TO ANY PRIORITY APPLICATIONS

Any and all priority claims identified in the Application Data Sheet, or any correction thereto, are hereby incorporated by reference under 37 CFR 1.57.

FIELD OF THE INVENTION

The present invention generally relates to the field of pharmaceutical sciences. More specifically, the present invention relates to pharmaceutical formulations containing large diameter synthetic membrane vesicles, such as multivesicular liposomes (MVL), methods for preparing such formulations, and the use of specific formulations for therapeutic treatment of subjects in need thereof.

BACKGROUND

The following includes information that may be useful in understanding the present embodiments. It is not an admission that any of the information provided herein is prior art, or relevant, to the presently described or claimed embodiments, or that any publication or document that is specifically or implicitly referenced is prior art.

Large scale methods of manufacturing large diameter synthetic membrane vesicles, such as multivesicular liposomes, often require large amounts of solvents, time sensitive steps and concentration adjustment of the final product under sterile conditions. In addition, current methods of manufacturing large diameter synthetic membrane vesicles, such as multivesicular liposomes on a commercial scale, require significant commitments in manufacturing space, cost, and time. As such, developing stable multivesicular liposome formulations containing a therapeutic agent in a cost effective and timely manner remains an ongoing challenge.

SUMMARY

Some embodiments provide an atomizing nozzle apparatus, comprising a first fluid conduit and a second fluid conduit each having at least one entrance orifice and at least one exit orifice, a fluid contacting chamber having a top comprising at least one entrance orifice and having a bottom comprising at least one exit orifice and connecting to the at least one exit orifice of the first fluid conduit, a third liquid channel, wherein the third fluid conduit annularly surrounds a portion of the fluid contacting chamber. In some embodiments, the fluid contacting chamber connects to the at least one exit orifice of the second fluid conduit. In some embodiments, the at least one exit orifice of the fluid contacting chamber and the at least one exit orifice of the third fluid conduit are flush. In some embodiments, the at least one exit orifice of the fluid contacting chamber is recessed within the at least one exit orifice of the third fluid conduit. In some embodiments, the at least one exit orifice of the fluid contacting chamber extends beyond the at least one exit orifice of the third fluid conduit. In some embodiments, the first fluid conduit and the second fluid conduit are co-axial for a first portion of the first fluid conduit length. In some embodiments, the second fluid conduit annularly surrounds a second portion of the first fluid conduit. In some embodiments, a diameter of the fluid contacting chamber is larger than a diameter of the first fluid conduit. In some embodiments, the fluid contacting chamber conically narrows in diameter from the top of the fluid contacting chamber to the exit orfice of the fluid contacting chamber. In some embodiments, the fluid contacting chamber conically narrows in diameter from a point below the top of the fluid contacting chamber to the exit orfice of the fluid contacting chamber.

Some embodiments provide a process for preparing droplets using an atomizing nozzle as disclosed herein comprising applying a first liquid to the first fluid conduit, applying a second liquid to the second fluid conduit, applying a gas to the third fluid conduit, wherein the gas exiting the third fluid conduit exit orifice impinges the liquid exiting the at least one exit orifice of the fluid contacting chamber, providing atomized droplets, wherein the droplets have an average diameter from about 100 nm to about 300 μM. In some embodiments, the first liquid is an emulsion comprised of a first aqueous phase, and a first organic phase comprising a first organic solvent. In some embodiments, the first organic solvent is chloroform or methylene chloride. In some embodiments, the first organic phase further comprises at least one amphipathic lipid and at least one neutral lipid. In some embodiments, the at least one amphipathic lipid is selected from the group consisting of phosphatidylcholines, phosphatidylserines, phosphatidylethanolamines, phosphatidylinositols, sphingomyelin, soybean lecithin (soya lecithin), egg lecithin, lysophosphatidylcholines, lysophosphatidylethanolamines, phosphatidylglycerols, phosphatidylserines, phosphatidylinositols, phosphatidic acids, cardiolipins, acyl trimethylammonium propane, diacyldimethylammonium propane, stearylamine, and ethyl phosphatidylcholine. In some embodiments, the at least one amphipathic lipid is selected from the group consisting of 1,2-dioleoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1,2-diarachidoyl-sn-glycero-3~phosphocholine, 1,2-dibehenoyl-sn-glycero-3-phosphocholine, 1,2-dipalmitoleoyl-sn-glycero-3-phosphocholine, 1,2-dieicosenoyl-sn-glycero-3-phosphocholine, 1,2-dierucoyl-sn-glycero-3-phosphocholine, 1,2-dipalmitoyl-sn-glycero-3-phosphoglycerol, 1,2-dioleoyl-sn-glycero-3-phosphoglycerol. In some embodiments, the at least one neutral lipid is selected from the group consisting of glycerol esters, glycol esters, tocopherol esters, sterol esters, hydrocarbons and squalenes. In some embodiments, the at least one neutral lipid is selected from the group consisting of triolein, tripalmitolein, trimyristolein, trilinolein, tributyrin, tricaprylin, tricaproin, and tricaprin. In some embodiments, the first aqueous phase further comprises a therapeutic agent. In some embodiments, the therapeutic agent is bupivacaine. In some embodiments, the second liquid applied to the second fluid conduit is a second aqueous phase. In some embodiments, the droplet comprises a first component core and a second aqueous phase shell. In some embodiments, the gas is nitrogen. In some embodiments, the droplets have an average diameter from about 20 μM to about 60 μM. In some embodiments, the droplets have an average diameter from about 35 μM to about 45 μM.

Some embodiments provide atomized droplet comprising an emulsion core, wherein the emulsion core comprises i) a first aqueous phase; and ii) a first organic phase comprising a first organic solvent; and an aqueous phase shell, wherein said atomized droplet is made by a process comprising combining a first component, an aqueous phase, and a gas using an atomizing nozzle as disclosed and described herein, said process comprising applying a first component to the first fluid conduit, applying an aqueous phase to the second fluid conduit, and applying a gas to the third fluid conduit, wherein the gas exiting the third fluid conduit exit orifice impinges the liquid exiting the at least one exit orifice of the fluid contacting chamber, providing atomized droplets, wherein the droplets have an average diameter from about 100 nm to about 300 µM.

Some embodiments provide atomizing nozzle apparatus, comprising an first fluid conduit, a second fluid conduit and a third fluid conduit each having at least one entrance orifice and at least one exit orifice, a first fluid contacting chamber having a top comprising at least one entrance orifice and having a bottom comprising at least one exit orifice and connecting to the at least one exit orifice of the first fluid conduit, wherein the second fluid conduit annularly surrounds a portion of the first fluid contacting chamber, a second fluid contacting chamber having a top comprising at least one entrance orifice and having a bottom comprising at least one exit orifice and connecting to the at least one exit orifice of the first fluid contacting chamber, wherein the third fluid conduit annularly surrounds a portion of the second fluid contacting chamber, and a fourth fluid conduit, wherein the fourth fluid conduit annularly surrounds a portion of the second fluid contacting chamber. In some embodiments, the first fluid contacting chamber connects to the at least one exit orifice of the second fluid conduit. In some embodiments, the at least one exit orifice of the second fluid contacting chamber and the at least one exit orifice of the fourth fluid conduit are flush. In some embodiments, the at least one exit orifice of the second fluid contacting chamber is recessed within the at least one exit orifice of the fourth fluid conduit. In some embodiments, the at least one exit orifice of the second fluid contacting chamber extends beyond the at least one exit orifice of the fourth fluid conduit. In some embodiments, the first fluid conduit and the second fluid conduit are co-axial for a first portion of the first fluid conduits length. In some embodiments, the second fluid conduit annularly surrounds a second portion of the first fluid conduit. In some embodiments, the first fluid contacting chamber conically narrows in diameter from the top of the fluid contacting chamber to the exit orfice of the fluid contacting chamber. In some embodiments, the second fluid conduit and the third fluid conduit are co-axial for a first portion of the second fluid conduits length. In some embodiments, the third fluid conduit annularly surrounds a second portion of the second fluid conduit. In some embodiments, the first fluid contacting chamber conically narrows in diameter from the top of the fluid contacting chamber to the exit orfice of the fluid contacting chamber.

Some embodiments provide a process for preparing droplets using an atomizing nozzle apparatus as disclosed and described herein, comprising applying a first liquid to the first fluid conduit, applying a second liquid to the second fluid conduit, applying a third liquid to the third fluid conduit, applying a gas to the fourth fluid conduit, wherein the gas exiting the fourth fluid conduit exit orifice impinges the liquid exiting the at least one exit orifice of the second fluid contacting chamber, providing atomized droplets, wherein the droplets have an average diameter from about 100 nm to about 300 µM. In some embodiments, the first liquid is an emulsion comprised of i) a first aqueous phase, and ii) a first organic phase comprising a first organic solvent, the second liquid is a second aqueous phase, and the third liquid is a second organic phase. In some embodiments, the first organic solvent is chloroform or methylene chloride.

In some embodiments, the first organic phase further comprises at least one amphipathic lipid and at least one neutral lipid.

Some embodiments provide an evaporation apparatus, comprising at least one atomizing nozzle apparatus of Claim 1 and means for evaporating an organic solvent.

Some embodiments provide an evaporation apparatus, comprising a solvent removal vessel having a top, a bottom and a circular wall, at least one atomizing nozzle connected to the circular wall, a carrier gas entrance orifice connected to the circular wall, a solvent removal gas exit orifice centrally connected to the top, and a product exit orifice connected to the bottom of the vessel. In some embodiments, at least part of the solvent removal vessel is jacketed. In some embodiments, the atomizing nozzle is mounted to and extending through the top of the solvent removal vessel. In some embodiments, the top of the solvent removal vessel comprises a lid. In some embodiments, the apparatus further comprises a rinse nozzle mounted to and extending through the top of the solvent removal vessel. In some embodiments, the circular wall has a central axis and the solvent removal gas exit orifice further comprises a tube extending into the solvent removal vessel residing along the central axis. In some embodiments, the atomizing nozzle is angled at least 5 degrees measured off the central axis of the wall and in a plane parallel to the wall nearest to it. In some embodiments, the carrier gas entrance orifice is combined with the atomizing nozzle. In some embodiments, the solvent removal gas exit orifice further comprises a tube extending into the solvent removal vessel, wherein the tube is fitted with a narrowing cone and an annular ring. In some embodiments, the tube extends from about ⅓ to about ⅘ of the way into the solvent removal vessel. In some embodiments, the tube extends about ⅔ of the way into the solvent removal vessel. In some embodiments, the bottom tip of the narrowing cone of the solvent removal gas exit orifice diameter is from about 1/1000 to about ⅕ of a diameter of the inside of the solvent removal vessel. In some embodiments, the solvent removal gas exit orifice diameter is less than 1/10 of a diameter of the inside of the solvent removal vessel. In some embodiments, the at least one atomizing nozzle is an atomizing nozzle apparatus as disclosed and described herein. In some embodiments, the ratio of the inside diameter of the solvent removal vessel to the diameter of the bottom tip of the narrowing cone of the solvent removal gas exit orifice is between approximately 5:1 and 100:1. In some embodiments, the ratio of the inside diameter of the solvent removal vessel to the diameter of the bottom tip of the narrowing cone of the solvent removal gas exit orifice is between approximately 20:1 and 60:1.

Some embodiments provide a process for preparing large diameter synthetic membrane vesicles using an evaporation apparatus as disclosed and described herein, comprising introducing large diameter synthetic membrane vesicles pre-droplets to the solvent removal vessel, wherein the large diameter synthetic membrane vesicles pre-droplets comprise a first component core and an aqueous phase shell, applying a carrier gas in a tangential direction to the circular wall through the carrier gas entrance orifice, and removing a solvent removal gas through the solvent removal gas exit orifice to provide the large diameter synthetic membrane vesicles. In some embodiments, the first component core comprises a first aqueous phase and a first organic phase. In some embodiments, the first organic phase comprises a continuous first organic solvent. In some embodiments, the first organic solvent is chloroform or methylene chloride. In some embodiments, the first organic phase further comprises at least one amphipathic lipid and at least one neutral lipid. In some embodiments, the first component core is first aqueous phase droplets as a suspension in a first organic phase. In some embodiments, the first aqueous phase droplets have an average diameter of from about 10 nm to about 10 µm, about 100 nm to about 5 µm, or about 500 nm to about 2 µm. In some embodiments, the first aqueous phase droplets have an average diameter of about 1 µm. In some embodiments, the carrier gas comprises nitrogen. In some embodiments, the carrier gas comprises nitrogen and water vapor. In some embodiments, the solvent removal gas comprises nitrogen and organic solvent. In some embodiments, the carrier gas and the solvent removal gas travel in a vortex in the solvent removal vessel. In some embodiments, the large diameter synthetic membrane vesicles are multivesicular liposomes having a structure including multiple non-concentric chambers and comprising at least one amphipathic lipid and at least one neutral lipid. In some embodiments, the at least one amphipathic lipid is selected from the group consisting of phosphatidylcholines, phosphatidylserines, phosphatidylethanolamines, phosphatidylinositols, sphingomyelin, soybean lecithin (soya lecithin), egg lecithin, lysophosphatidylcholines, lysophosphatidylethanolamines, phosphatidylglycerols, phosphatidylserines, phosphatidylinositols, phosphatidic acids, cardiolipins, acyl trimethylammonium propane, diacyldimethylammonium propane, stearylamine, and ethyl phosphatidylcholine. In some embodiments, the at least one amphipathic lipid is selected from the group consisting of 1,2-dioleoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1,2-diarachidoyl-sn-glycero-3-phosphocholine, 1,2-dibehenoyl-sn-glycero-3-phosphocholine, 1,2-dipalmitoleoyl-sn-glycero-3-phosphocholine, 1,2-dieicosenoyl-sn-glycero-3-phosphocholine, 1,2-dierucoyl-sn-glycero-3-phosphocholine, 1,2-dipalmitoyl-sn-glycero-3-phosphoglycerol, and 1,2-dioleoyl-sn-glycero-3-phosphoglycerol. In some embodiments, the at least one neutral lipid is selected from the group consisting of glycerol esters, glycol esters, tocopherol esters, sterol esters, hydrocarbons and squalenes. In some embodiments, the at least one neutral lipid is selected from the group consisting of triolein, tripalmitolein, trimyristolein, trilinolein, tributyrin, tricaprylin, tricaproin, and tricaprin. In some embodiments, the multivesicular liposomes further comprises a therapeutic agent. In some embodiments, the therapeutic agent is bupivacaine. In some embodiments, the multivesicular liposomes comprises an outer surface layer whose composition is different than the composition of the internal structure.

Some embodiments provide an evaporation apparatus, comprising at least one atomizing nozzle apparatus as disclosed and described herein and means for removing an organic solvent from a droplet.

Some embodiments provide a process for preparing large diameter synthetic membrane vesicles using the evaporation apparatus as disclosed and described herein, comprising introducing large diameter synthetic membrane vesicles pre-droplets to the solvent removal vessel, wherein the large diameter synthetic membrane vesicles pre-droplets comprise a first component core and an aqueous phase shell; applying a carrier gas in a tangential direction to the circular wall through the carrier gas entrance orifice; removing a solvent removal gas through the solvent removal gas exit orifice to provide pre-temperature treatment large diameter synthetic membrane vesicles; introducing the pre-temperature treatment large diameter synthetic membrane vesicles to an outlet line; contacting the pre-temperature treatment large diameter synthetic membrane vesicles with a hot solution in the outlet line, wherein the hot solution has a temperature ranging from about 30° C. to about 100° C. to provide post-temperature treatment large diameter synthetic membrane vesicles; transferring the post-temperature treatment large diameter synthetic membrane vesicles to a continuous-flow particle-concentration system or continuous phase exchange system; cooling the post-temperature treatment large diameter synthetic membrane vesicles to a second temperature to provide the large diameter synthetic membrane vesicles; and isolating the large diameter synthetic membrane vesicles. In some embodiments, the first component core comprises a first aqueous phase and a first organic phase. In some embodiments, the first organic phase comprises a continuous first organic solvent. In some embodiments, the first organic solvent is chloroform or methylene chloride. In some embodiments, the first organic phase further comprises at least one amphipathic lipid and at least one neutral lipid. In some embodiments, the first component core is a suspension of first aqueous phase droplets in a first organic phase. In some embodiments, the first aqueous phase droplets have an average diameter of from about 10 nm to about 10 µm, about 100 nm to about 5 µm, or about 500 nm to about 2 µm. In some embodiments, the first aqueous phase droplets have an average diameter of about 1 µm. In some embodiments, the carrier gas comprises nitrogen. In some embodiments, the solvent removal gas comprises nitrogen and organic solvent. In some embodiments, the carrier gas and the solvent removal gas travel in a vortex in the solvent removal vessel. In some embodiments, the large diameter synthetic membrane vesicles are multivesicular liposomes having a structure including multiple non-concentric chambers and comprising at least one amphipathic lipid and at least one neutral lipid. In some embodiments, the at least one amphipathic lipid is selected from the group consisting of phosphatidylcholines, phosphatidylserines, phosphatidylethanolamines, phosphatidylinositols, sphingomyelin, soybean lecithin (soya lecithin), egg lecithin, lysophosphatidylcholines, lysophosphatidylethanolamines, phosphatidylglycerols, phosphatidylserines, phosphatidylinositols, phosphatidic acids, cardiolipins, acyl trimethylammonium propane, diacyldimethylammonium propane, stearylamine, and ethyl phosphatidylcholine. In some embodiments, the at least one amphipathic lipid is selected from the group consisting of 1,2-dioleoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1,2-diarachidoyl-sn-glycero-3~phosphocholine, 1,2-dibehenoyl-sn-glycero-3-phosphocholine, 1,2-dipalmitoleoyl-sn-glycero-3-phosphocholine, 1,2-dieicosenoyl-sn-glycero-3-phosphocholine, 1,2-dierucoyl-sn-glycero-3-phosphocholine, 1,2-dipalmitoyl-sn-glycero-3-phosphoglycerol, and 1,2-dioleoyl-sn-glycero-3-phosphoglycerol. In some embodiments, the at least one neutral lipid is selected from the group consisting of glycerol esters, glycol esters, tocopherol esters, sterol esters, hydrocarbons and squalenes. In some embodiments, the at least one neutral lipid is selected from the group consisting of triolein, tripalmitolein, trimyristolein, trilinolein, tributyrin, tricaprylin, tricaproin, and tricaprin. In some embodiments, the multivesicular liposomes further comprises a therapeutic agent. In some embodiments, the therapeutic agent is bupivacaine.

Some embodiments provide a composition comprising multivesicular liposomes having a structure including multiple non-concentric chambers and comprising at least one amphipathic lipid and at least one neutral lipid, wherein said multivesicular liposomes are made by a process comprising removing organic solvent from multivesicular liposomes pre-droplets using an evaporation apparatus as disclosed and described herein, said process comprising introducing multivesicular liposomes pre-droplets pre-droplets to the solvent removal vessel, wherein the large diameter synthetic membrane vesicles pre-droplets comprise a first component core and an aqueous phase shell; applying a carrier gas in a tangental direction to the circular wall through the carrier gas entrance orifice; and removing a solvent removal gas through the solvent removal gas exit orifice to provide the large diameter synthetic membrane vesicles.

Some embodiments provide a composition comprising large diameter synthetic membrane vesicles made by a process disclosed and described herein. In some embodiments, the large diameter synthetic membrane vesicles are multivesicular liposomes having a structure including multiple non-concentric chambers and comprising at least one amphipathic lipid and at least one neutral lipid. In some embodiments, the at least one amphipathic lipid is selected from the group consisting of phosphatidylcholines, phosphatidylserines, phosphatidylethanolamines, phosphatidylinositols, sphingomyelin, soybean lecithin (soya lecithin), egg lecithin, lysophosphatidylcholines, lysophosphatidylethanolamines, phosphatidylglycerols, phosphatidylserines, phosphatidylinositols, phosphatidic acids, cardiolipins, acyl trimethylammonium propane, diacyldimethylammonium propane, stearylamine, and ethyl phosphatidylcholine. In some embodiments, the at least one amphipathic lipid is selected from the group consisting of 1,2-dioleoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1,2-diarachidoyl-sn-glycero-3~phosphocholine, 1,2-dibehenoyl-sn-glycero-3-phosphocholine, 1,2-dipalmitoleoyl-sn-glycero-3-phosphocholine, 1,2-dieicosenoyl-sn-glycero-3-phosphocholine, 1,2-dierucoyl-sn-glycero-3-phosphocholine, 1,2-dipalmitoyl-sn-glycero-3-phosphoglycerol, and 1,2-dioleoyl-sn-glycero-3-phosphoglycerol. In some embodiments, the at least one neutral lipid is selected from the group consisting of glycerol esters, glycol esters, tocopherol esters, sterol esters, hydrocarbons and squalenes. In some embodiments, the at least one neutral lipid is selected from the group consisting of triolein, tripalmitolein, trimyristolein, trilinolein, tributyrin, tricaprylin, tricaproin, and tricaprin. In some embodiments, the multivesicular liposomes further comprises a therapeutic agent. In some embodiments, the therapeutic agent is bupivacaine.

Some embodiments provide a continuous-flow emulsification system, comprising a mixer, comprised of a rotor and a stator; a recirculation loop, comprised of one or more recirculation lines; a heat exchanger; one or more outlet lines; one or more continuous phase inlet lines; and a discontinuous phase inlet line, wherein the heat exchanger and the mixer are connected together in the recirculation loop by one or more recirculation lines; further wherein the one or more outlet lines and one or more continuous phase inlet lines are connected to the recirculation loop; further wherein the end of the discontinuous phase inlet line is located within approximately ⅓rd of a rotor diameter from the rotor and approximately ⅓rd of a rotor diameter of the rotation axis of the rotor and is in fluid communication with the rotor. In some embodiments, a continuous phase entrance line is connected to the recirculation loop upstream of the mixer and downstream of the heat exchanger and an outlet line is connected to the recirculation loop downstream of the mixer and upstream of the heat exchanger. In some embodiments, the continuous-flow emulsification system further comprises an emulsion, which emulsion recirculates through the recirculation line back to the mixer an average of at least 5 or more times. In some embodiments, the continuous-flow emulsification system further comprises emulsion droplets produced in the mixer, which are on average less than 10 microns in diameter.

Some embodiments provide a continuous processing system, comprising one or more concentrator units, each unit comprising a retentate vessel; a particle suspension inlet line, connected to the retentate vessel; a first outlet line, connecting the retentate vessel and a particle concentrating device; a pump located along the first outlet line between the retentate vessel and the particle concentrating device; and a second outlet line, leading to another concentrator unit or the final product collection vessel; and means for removing or exchanging solvent. In some embodiments, the means for removing or exchanging solvent are each independently selected from the group consisting of a tangential flow filtration unit, a hydro-cyclone unit, and a centrifugal separator. In some embodiments, the continuous processing system further comprises a new suspending medium inlet line connected to the retentate vessel. In some embodiments, the means for removing or exchanging solvent are each a tangential flow filtration unit. In some embodiments, the means for removing or exchanging solvent are each a centrifugal separator. In some embodiments, the system comprises at least one tangential flow filtration unit and at least one centrifugal separator. In some embodiments, the continuous processing system is a continuous-flow particle-concentration system or continuous phase exchange system.

Some embodiments provide a process for making multivesicular liposomes using the atomizing nozzle apparatus as disclosed and described herein, comprising applying a first liquid to the first fluid conduit, wherein the first liquid comprises an organic solvent, applying a second liquid to the second fluid conduit, applying a pressurized gas to the third fluid conduit to provide atomized droplets, wherein the pressurized gas exiting the third fluid conduit exit orifice impinges the liquid exiting the fluid contacting chamber exit orifice, and removing the organic solvent from the atomized droplets, wherein less than 4000 ppm of the organic solvent remains in the atomized droplets. In some embodiments, the first liquid is an emulsion comprised of a discontinuous aqueous phase, and a continuous organic phase comprising the organic solvent. In some embodiments, the organic solvent is methylene chloride. In some embodiments, the continuous organic phase further comprises a therapeutic agent. In some embodiments, the therapeutic agent is bupivacaine or a salt thereof. In some embodiments, the second liquid applied to the second fluid conduit is an aqueous solution. In some embodiments, the aqueous solution further comprises dextrose and lysine. In some embodiments, the gas is a sterilized gas. In some embodiments, the gas is nitrogen. In some embodiments, the process further comprises introducing atomized droplets to an evaporation apparatus as disclosed and described herein; introducing a pressurized carrier gas tangentially to the circular wall into the solvent removal vessel through the carrier gas entrance orifice; removing a solvent removal gas wherein the solvent removal gas removes greater than 90% of the organic solvent in the atomized droplets resulting in formation of multivesicular liposomes. In some embodiments, the carrier gas is heated and humidified. In some embodiments, the process further comprises spraying a wall rinse solution into the solvent removal vessel using a rinse nozzle, wherein the wall rinse solution prevents build-up of particles in the evaporation apparatus. In some embodiments, the atomized droplets contain organic solvent in the range of from about 400 ppm to about 3500 ppm.

Some embodiments provide a process for making an emulsion using an emulsification system as disclosed and described herein, comprising feeding an organic discontinuous phase into the emulsification system through the discontinuous phase inlet line and feeding an aqueous continuous phase into the emulsification system through one or more continuous phase inlet lines.

Some embodiments provide a process for making an emulsion using the emulsification system as disclosed and described herein, comprising feeding an aqueous discontinuous phase into the emulsification system through the discontinuous phase inlet line and feeding an organic continuous phase fed into the emulsification system through the one or more continuous phase inlet lines. In some embodiments, the organic continuous phase is comprised of an organic solvent and a neutral lipid. In some embodiments, the organic solvent is methylene chloride. In some embodiments, the aqueous discontinuous phase is comprised of an acid and a therapeutic agent. In some embodiments, the acid is phosphoric acid. In some embodiments, the therapeutic agent is bupivacaine. In some embodiments, a portion of the emulsion is fed through one or more outlet lines to the inner fluid conduit of an atomizing nozzle as disclosed and described herein. In some embodiments, a portion of the emulsion is fed through one or more outlet lines to an evaporation apparatus as disclosed and described herein.

Some embodiments provide a process for preparing large diameter synthetic membrane vesicles using an evaporation apparatus as disclosed and described herein.

Some embodiments provide a large diameter synthetic membrane vesicles made by a process as disclosed and described herein.

Some embodiments produce a plurality of MVL particles made by using the process utilizing the atomizing nozzle disclosed herein.

Some embodiments produce a plurality of MVL particles made by using the process utilizing the emulsification system and the atomizing nozzle disclosed herein.

Some embodiments produce a plurality of MVL particles made by using the process utilizing the evaporation apparatus and the atomizing nozzle disclosed herein.

Some embodiments produce a plurality of MVL particles made by using the process utilizing the emulsification system, the evaporation apparatus and the atomizing nozzle disclosed herein.

Some embodiments produce a plurality of MVL particles made by using the process utilizing the evaporation apparatus, the atomizing nozzle, and particle concentration system disclosed herein.

Some embodiments produce a plurality of MVL particles made by using the process utilizing the emulsification system, the evaporation apparatus, the atomizing nozzle, and particle concentration system disclosed herein.

Some embodiments produce a plurality of MVL particles made by any of the above product-by-process embodiments, wherein the MVL contains bupivacaine or a pharmaceutically acceptable salt thereof.

BRIEF DESCRIPTION OF THE DRAWINGS

These and other objects and features of the instant embodiment will become more fully apparent in the following descriptions and appended claims taken in conjunction with the following drawings where like references numbers indicate identical or functionally similar elements.

FIG. 3A is a schematic view of one embodiment of a three channel atomizing nozzle used in a manufacturing system, such as the manufacturing system of FIG. 1A of FIG. 1B.

FIG. 3B is a cross-sectional view of the atomizing nozzle of FIG. 3A, taken along line B of FIG. 3A.

FIG. 3C is an expanded view of the cylindrical tip of the atomizing nozzle of FIG. 3A, shown as position C in FIG. 3A.

FIG. 3D is an expanded view of an atomized droplet produced by the atomizing nozzle of FIG. 3A, shown as position D in FIG. 3A.

FIG. 3E is a schematic view of one embodiment of a four channel atomizing nozzle used in a manufacturing system, such as the manufacturing system of FIG. 1A or FIG. 1B.

FIG. 3F is a cross-sectional view of the atomizing nozzle of FIG. 3E, taken along line F of FIG. 3E.

FIG. 3G is an expanded view of the cylindrical tip of the atomizing nozzle of FIG. 3E, shown as position G in FIG. 3E.

FIG. 3H is an expanded view of an atomized droplet produced by the atomizing nozzle of FIG. 3E, shown as position H in FIG. 3E.

FIG. 3I is a schematic view of another embodiment of a four channel atomizing nozzle used in a manufacturing system, such as the manufacturing system of FIG. 1A or FIG. 1B.

FIG. 3J is a cross-sectional view of the atomizing nozzle of FIG. 3I, taken along line J of FIG. 3I.

FIG. 3K is an expanded view of the cylindrical tip of the atomizing nozzle of FIG. 3I, shown as position K in FIG. 3I.

FIG. 3L is an expanded view of an atomized droplet produced by the atomizing nozzle of FIG. 3I, shown as position L in FIG. 3I.

FIG. 4A is a schematic view of one embodiment of an atomizing nozzle used in a manufacturing system, such as the manufacturing system of FIG. 1A or FIG. 1B.

FIG. 4B is a cross-sectional view of the atomizing nozzle of FIG. 4A, taken along line B of FIG. 4A.

FIG. 4C is an expanded view of the cylindrical tip of the atomizing nozzle of FIG. 4A, shown as position C in FIG. 4A.

FIG. 4D is an expanded view of an atomized droplet produced by the atomizing nozzle of FIG. 4A, shown as position D in FIG. 4A.

FIG. 15 is a graph of an in-vivo release profile study of a multivesicular formulation made with and without heat treatment.

Large scale methods of manufacturing large diameter synthetic membrane vesicles, such as multivesicular liposomes, often require large amounts of solvents, time sensitive steps and concentration adjustment of the final product under sterile conditions, for example, as described in WO99/25319. In addition, current methods of manufacturing large diameter synthetic membrane vesicles, such as multivesicular liposomes on a commercial scale, require significant commitments in manufacturing space, cost, and time. As such, developing stable multivesicular liposome formulations containing a therapeutic agent in a cost effective and timely manner remains an ongoing challenge.

In large scale manufacturing of large diameter synthetic membrane vesicles, the present embodiments require less water for injection (WFI), space, time and energy to produce an equivalent amount of the large diameter synthetic membrane vesicles than under previously described large scale manufacturing conditions. As a result, waste disposal is reduced and overall costs are reduced. For example, the present embodiments provide systems that can be housed in a one story room (e.g. 5×5 meter room) that previously described systems would require a multistory room with at least a ten fold increase in the area of the room. Additionally, the present embodiments provide systems that are particularly well adapted to continuous processing for more rapid production of large diameter synthetic membrane vesicles and allowing for more efficient implementation of clean-in-place (CIP) and sterile-in-place (SIP) protocols. Allowing for greatly reduced utility requirements to implement CIP and SIP protocols.

Figure 1A:
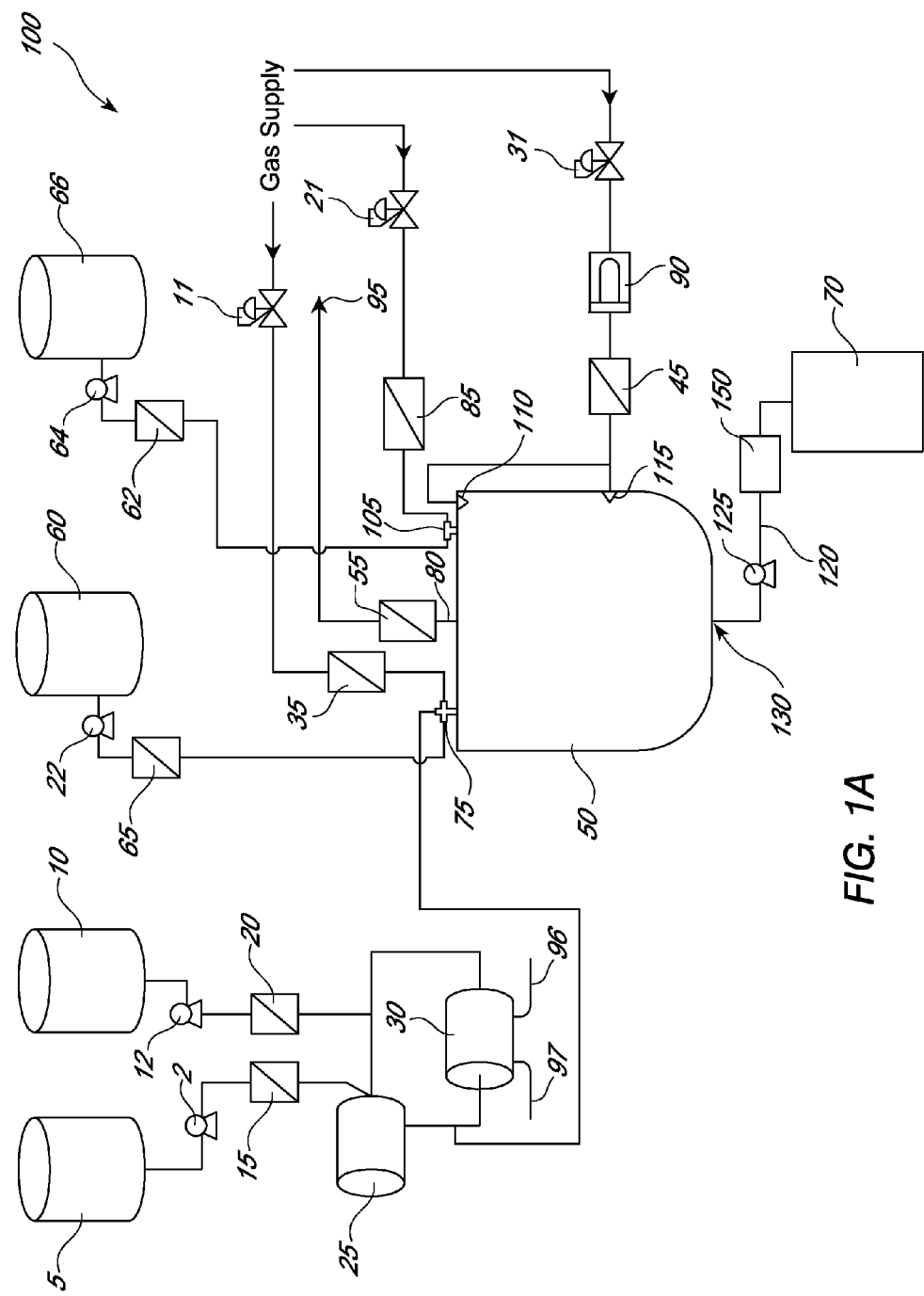
FIG. 1A is a schematic diagram of significant components used in one of the instant systems for manufacturing synthetic membrane vesicles.
Figure 1B:
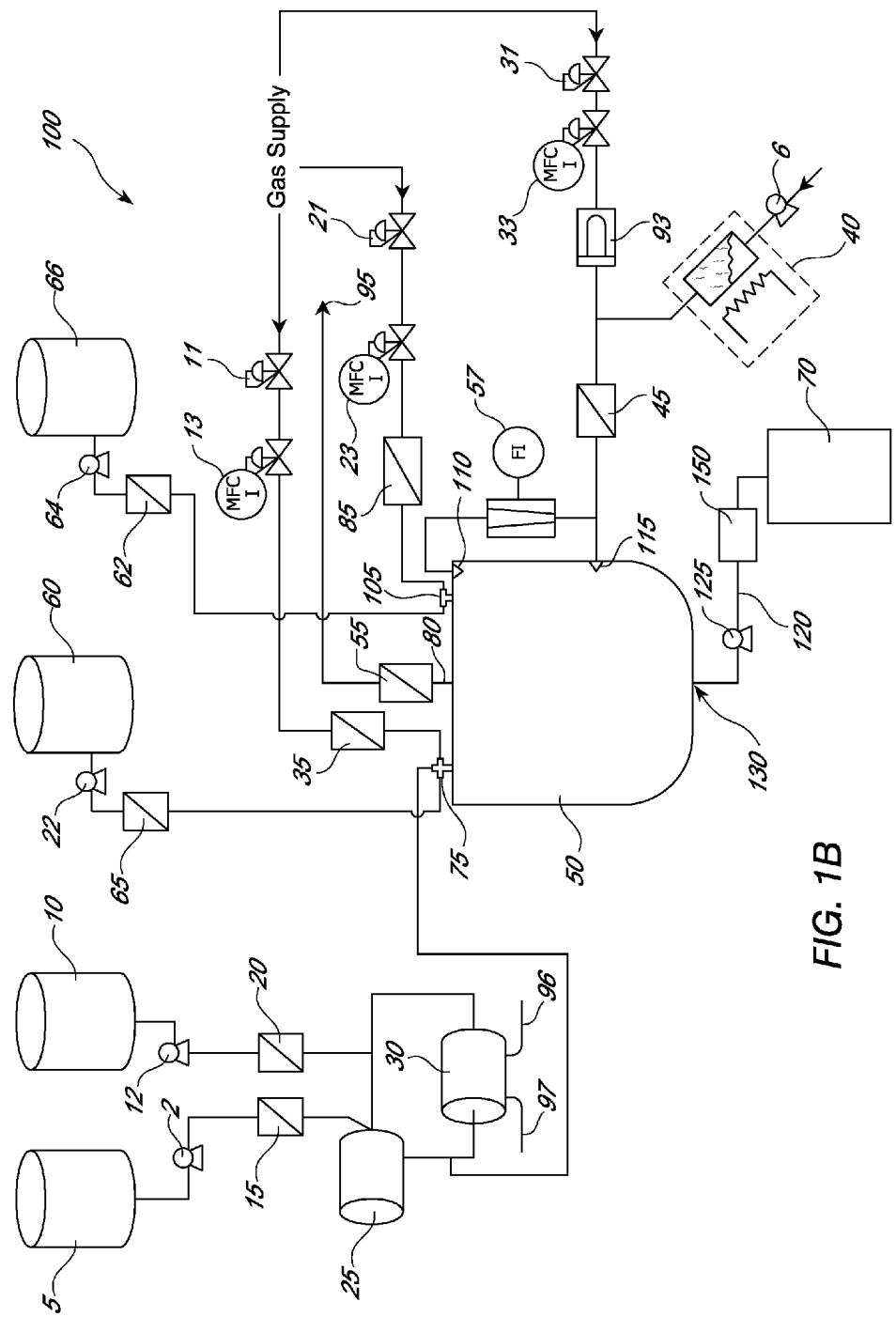
FIG. 1B is a schematic diagram of significant components used in another system for manufacturing synthetic membrane vesicles.

The devices described in FIGS. 1A and 1B are particularly well suited for making multivesicular liposomes (MVL). Multivesicular liposomes (MVL), first reported by Kim, et al. (Biochim, Biophys. Acta, 728:339-348, 1983), are uniquely different from other lipid-based drug delivery systems such as unilamellar (Huang, Biochemistry, 8:334-352, 1969; Kim, et al., Biochim. Biophys. Acta, 646:1-10, 1981) and multilamellar (Bangham, et al., J Mol. Bio., 13:238-252, 1965) liposomes. For example, multivesicular liposomes made by the processes described herein typically can have diameters ranging from about 10 to 100 μm, and more typically ranging from about 20 to 55 μm. In contrast, multilamellar liposomes usually have diameters of from 0.2 to 5 μm and unilamellar liposomes usually have diameters of from 0.02 to 0.5 μm.

Additionally, multivesicular liposomes (MVL) contain multiple aqueous chambers per particle and the multiple aqueous chambers are non-concentric. In contrast unilamellar liposomes (also known as unilamellar vesicles) and multilamellar liposomes (also known as multilamellar vesicles) contain a single chamber per particle. Further, neutral lipids are necessary to form multivesicular liposomes (MVL). In contrast unilamellar liposomes (also known as unilamellar vesicles) and multilamellar liposomes (also known as multilamellar vesicles) do not require inclusion of neutral lipids to form.

Multivesicular liposomes (MVL) are entirely distinct from unilamellar liposomes and multilamellar liposomes. The structural and functional characteristics of multivesicular liposomes are not directly predictable from current knowledge of unilamellar liposomes and multilamellar liposomes. As described in the book edited by Jean R. Philippot and Francis Schuber (Liposomes as Tools in Basic Research and Industry, CRC press, Boca Raton, Fla., 1995, page 19), Multivesicular liposomes (MVL) are bounded by an external bilayer membrane shell, but have a very distinctive internal morphology, which may arise as a result of the special method employed in the manufacture. Topologically, multivesicular liposomes (MVL) are defined as liposomes containing multiple non-concentric chambers within each liposome particle, resembling a "foam-like" matrix; whereas multilamellar vesicles contain multiple concentric chambers within each liposome particle, resembling the "layers of an onion".

The presence of internal membranes distributed as a network throughout multivesicular liposomes (MVL) may serve to confer increased mechanical strength to the vesicle, while still maintaining a high volume:lipid ratio compared with multilamellar vesicles. The multivesicular nature of multivesicular liposomes (MVL) also indicates that, unlike for unilamellar liposomes, a single breach in the external membrane of a multivesicular liposomes (MVL) will not result in total release of the internal aqueous contents. Thus, both structurally and functionally the multivesicular liposomes (MVL) are unusual, novel and distinct from all other types of liposomes. As a result, the functional properties of multivesicular liposomes (MVL) are not predictable based on the prior art related to conventional liposomes such as unilamellar liposomes and multilamellar liposomes.

In some embodiments, the large diameter synthetic membrane vesicles are multivesicular liposomes. In some embodiments, the multivesicular liposomes further comprise bupivaciane, DEPC, DPPG, and tricaprylin. In some embodiments, the multivesicular liposomes further comprise bupivacaine phosphate, DEPC, DPPG, and tricaprylin. In some embodiments, the multivesicular liposomes further comprise bupivacaine, DEPC, DPPG, tricaprylin and cholesterol. In some embodiments, the multivesicular liposomes further comprise bupivacaine phosphate, DEPC, DPPG, tricaprylin and cholesterol.

In some embodiments, the multivesicular liposomes further comprise bupivaciane, dextrose, L-Lysine, DEPC, DPPG, and tricaprylin. In some embodiments, the multivesicular liposomes further comprise bupivacaine phosphate, dextrose, L-Lysine, DEPC, DPPG, and tricaprylin. In some embodiments, the multivesicular liposomes further comprise bupivacaine, dextrose, L-Lysine, DEPC, DPPG, tricaprylin and cholesterol. In some embodiments, the multivesicular liposomes further comprise bupivacaine phosphate, dextrose, L-Lysine, DEPC, DPPG, tricaprylin and cholesterol.

In some embodiments, the multivesicular liposomes further comprise bupivaciane, dextrose, DEPC, DPPG, and tricaprylin. In some embodiments, the multivesicular liposomes further comprise bupivacaine phosphate, dextrose, DEPC, DPPG, and tricaprylin. In some embodiments, the multivesicular liposomes further comprise bupivacaine, dextrose, DEPC, DPPG, tricaprylin and cholesterol. In some embodiments, the multivesicular liposomes further comprise bupivacaine phosphate, dextrose, DEPC, DPPG, tricaprylin and cholesterol.

In some embodiments, the multivesicular liposomes further comprise bupivaciane, L-Lysine, DEPC, DPPG, and tricaprylin. In some embodiments, the multivesicular liposomes further comprise bupivacaine phosphate, L-Lysine, DEPC, DPPG, and tricaprylin. In some embodiments, the multivesicular liposomes further comprise bupivacaine, L-Lysine, DEPC, DPPG, tricaprylin and cholesterol. In some embodiments, the multivesicular liposomes further comprise bupivacaine phosphate, L-Lysine, DEPC, DPPG, tricaprylin and cholesterol.

In some embodiments, the multivesicular liposomes further comprise bupivacaine, morphine, cytarabine, or their pharmaceutically acceptable salts as the therapeutic agent. In some embodiments, the multivesicular liposomes further comprise bupivacaine phosphate, morphine sulfate, or cytarabine HCl.

Figure 1C:
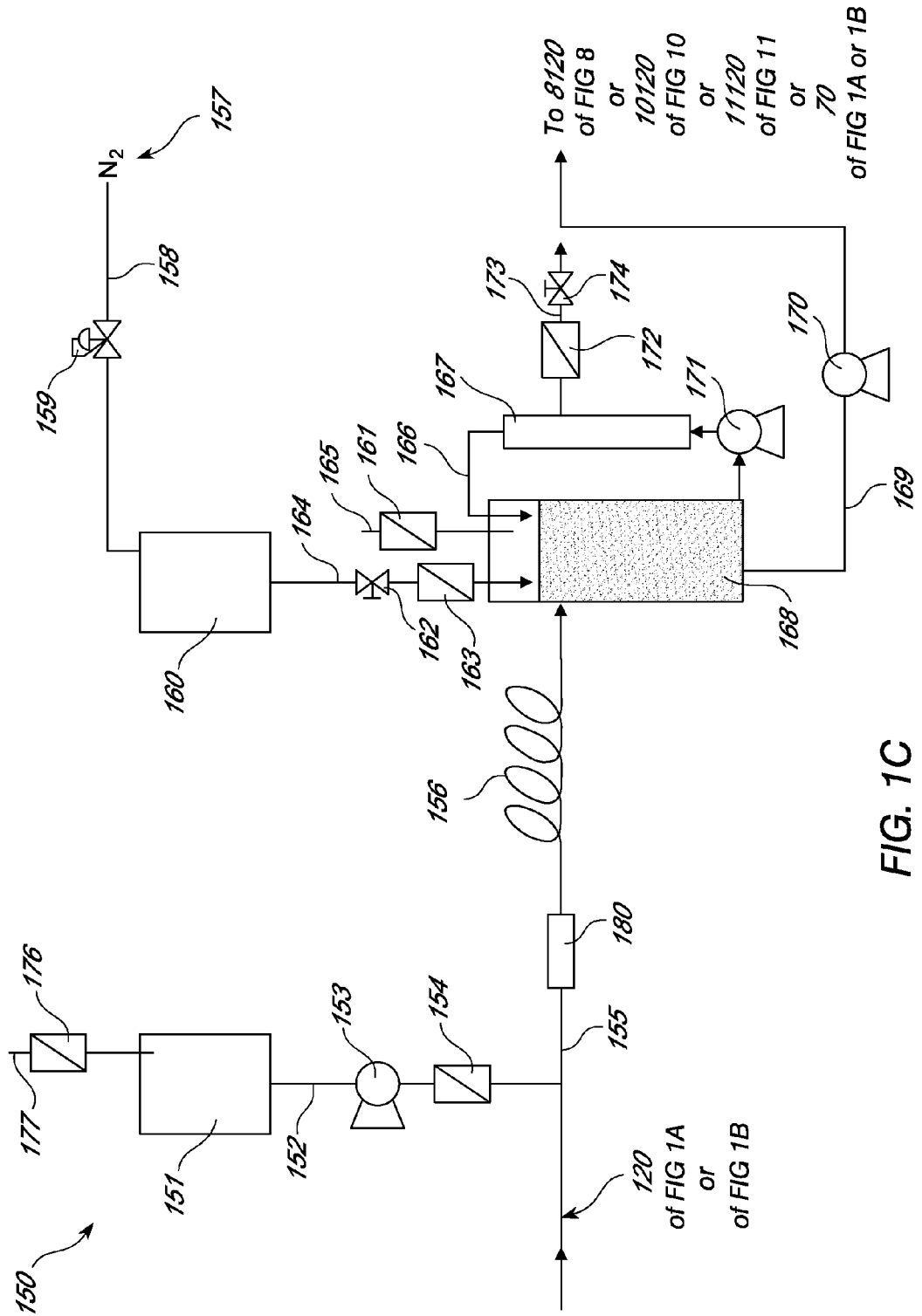
FIG. 1C is a schematic of one embodiment of a continuous heat treatment system including a temperature controlled tank and a holding coil tubing used in a manufacturing system such as the manufacturing system of FIG. 1A or FIG. 1B.
Figure 8:
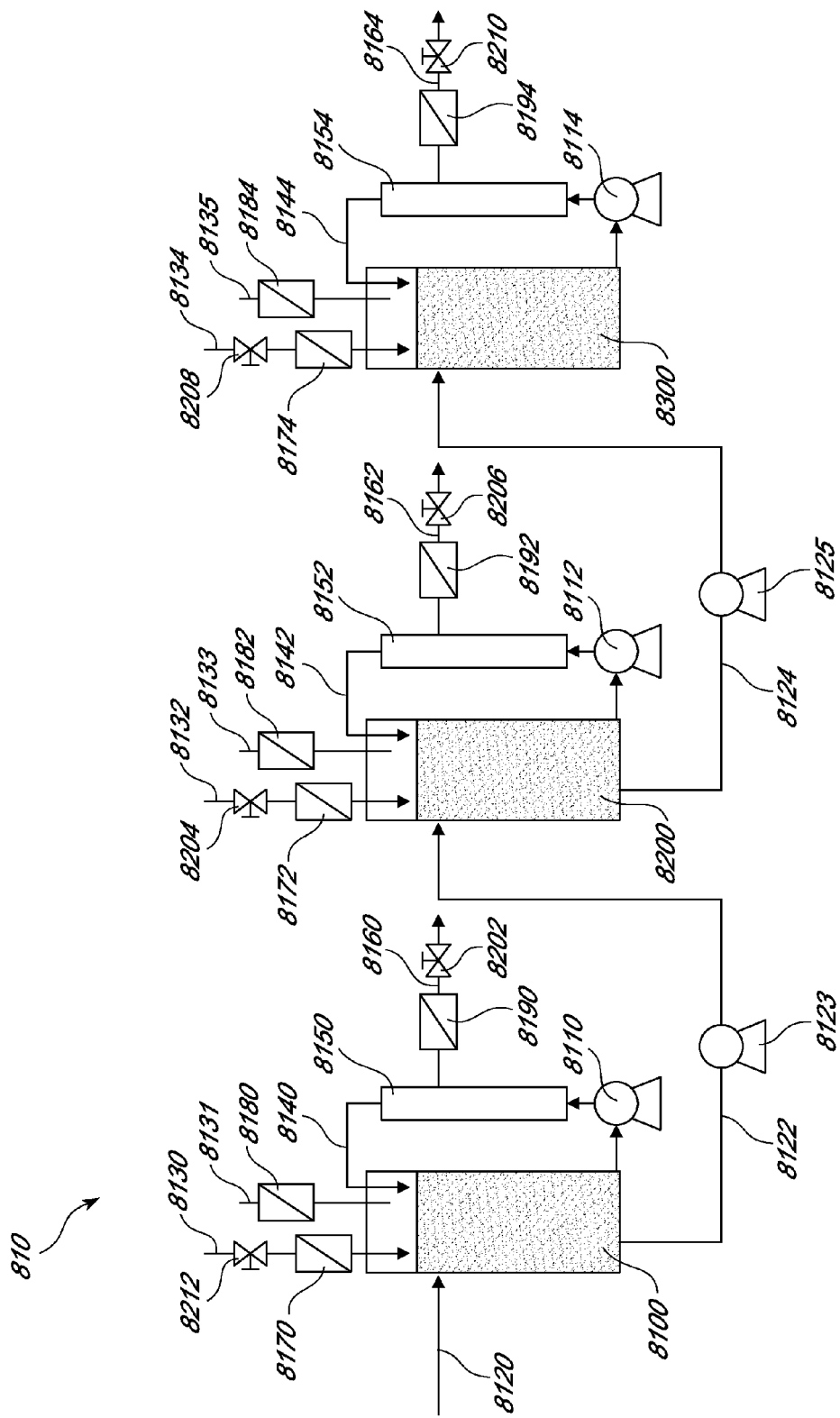
FIG. 8 is a schematic of one embodiment of a particle concentration system used in a manufacturing system such as the manufacturing system of FIG. 1A or FIG. 1B.
Figure 10:
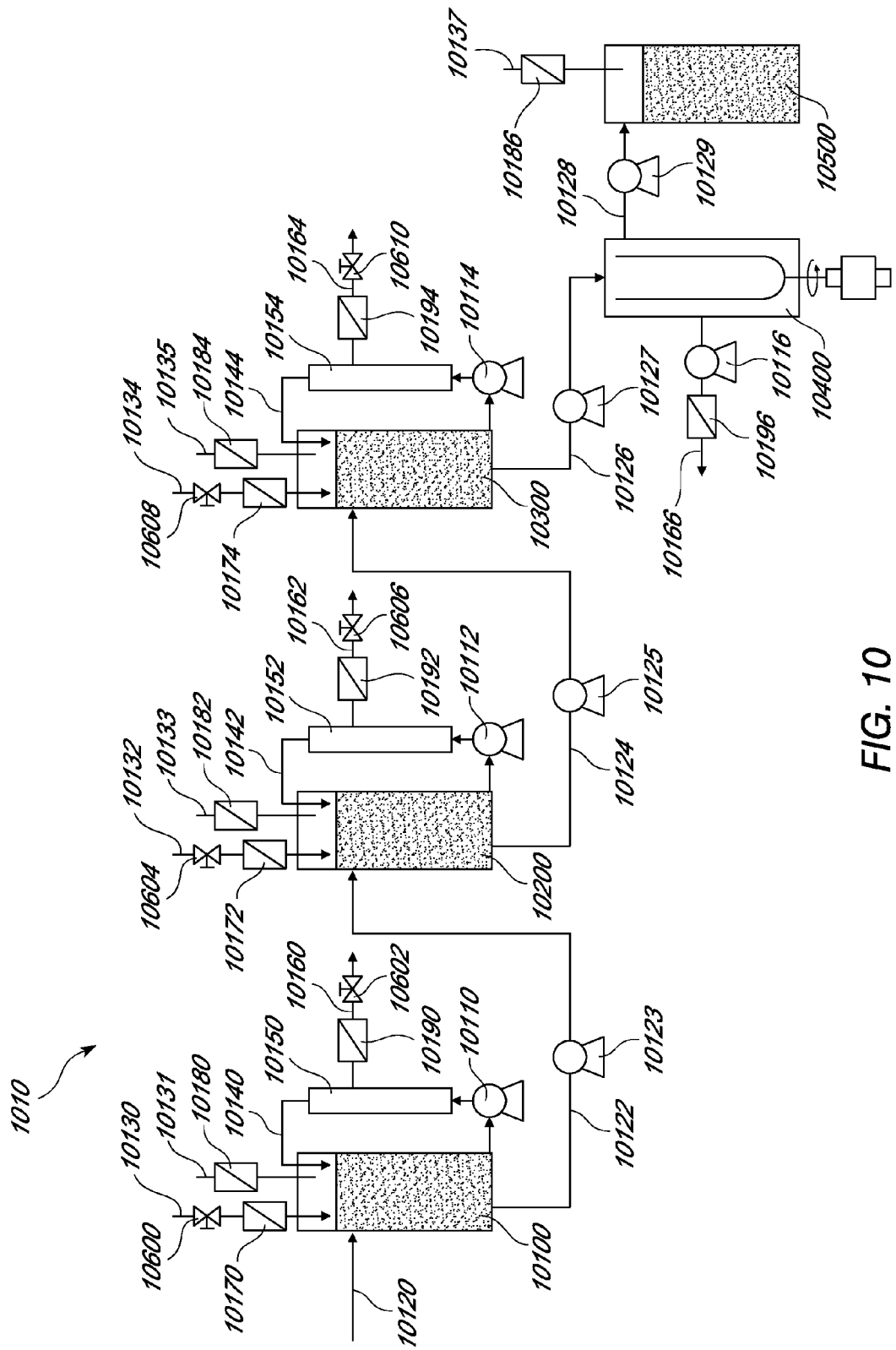
FIG. 10 is a schematic of one embodiment of a particle concentration system including a plurality of filtration units and at least one centrifuge unit used in a manufacturing system such as the manufacturing system of FIG. 1A or FIG. 1B.
Figure 11:
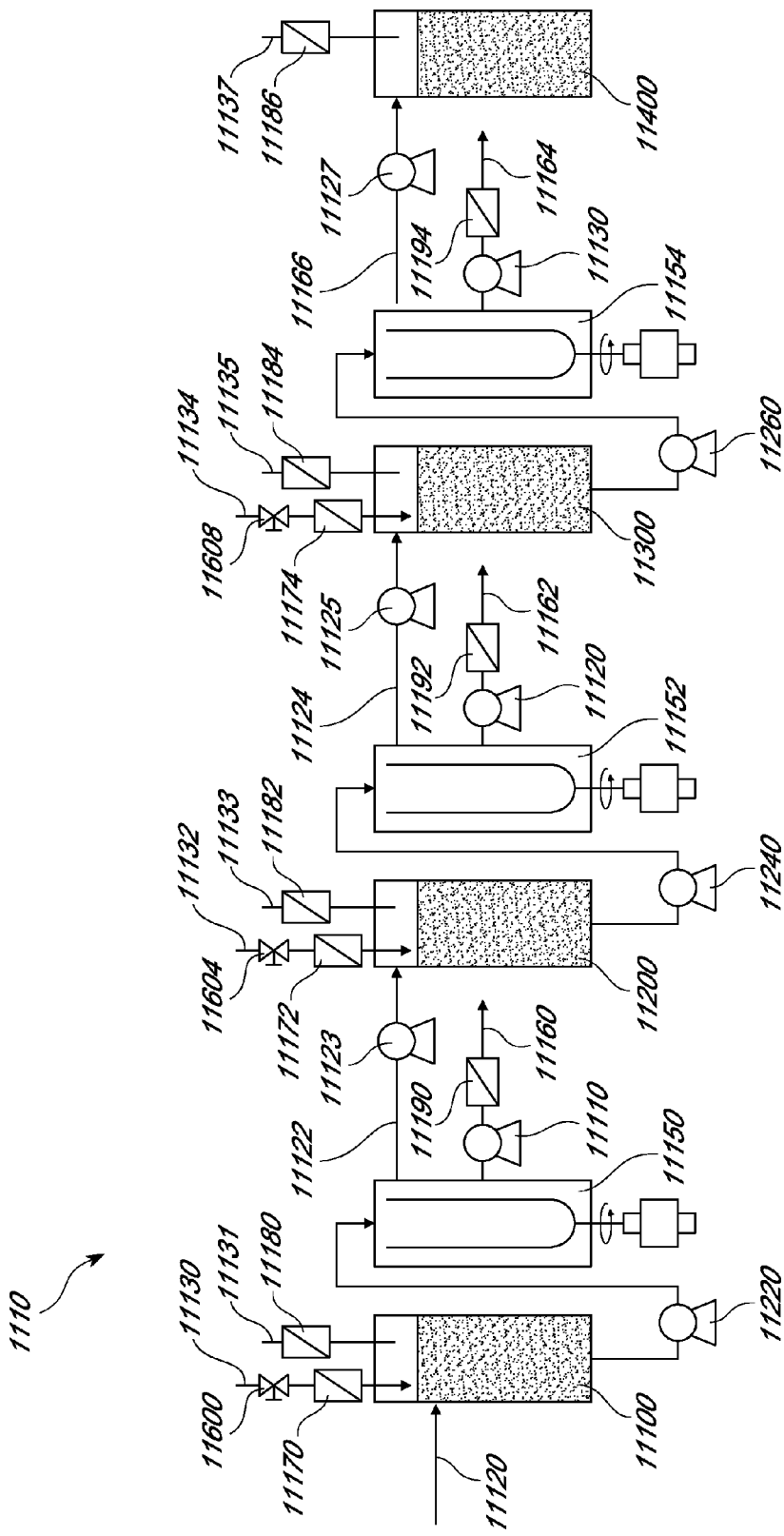
FIG. 11 is a schematic of one embodiment of a particle concentration system including a plurality of centrifuge units used in a manufacturing system such as the manufacturing system of FIG. 1A or FIG. 1B.
Figure 12:
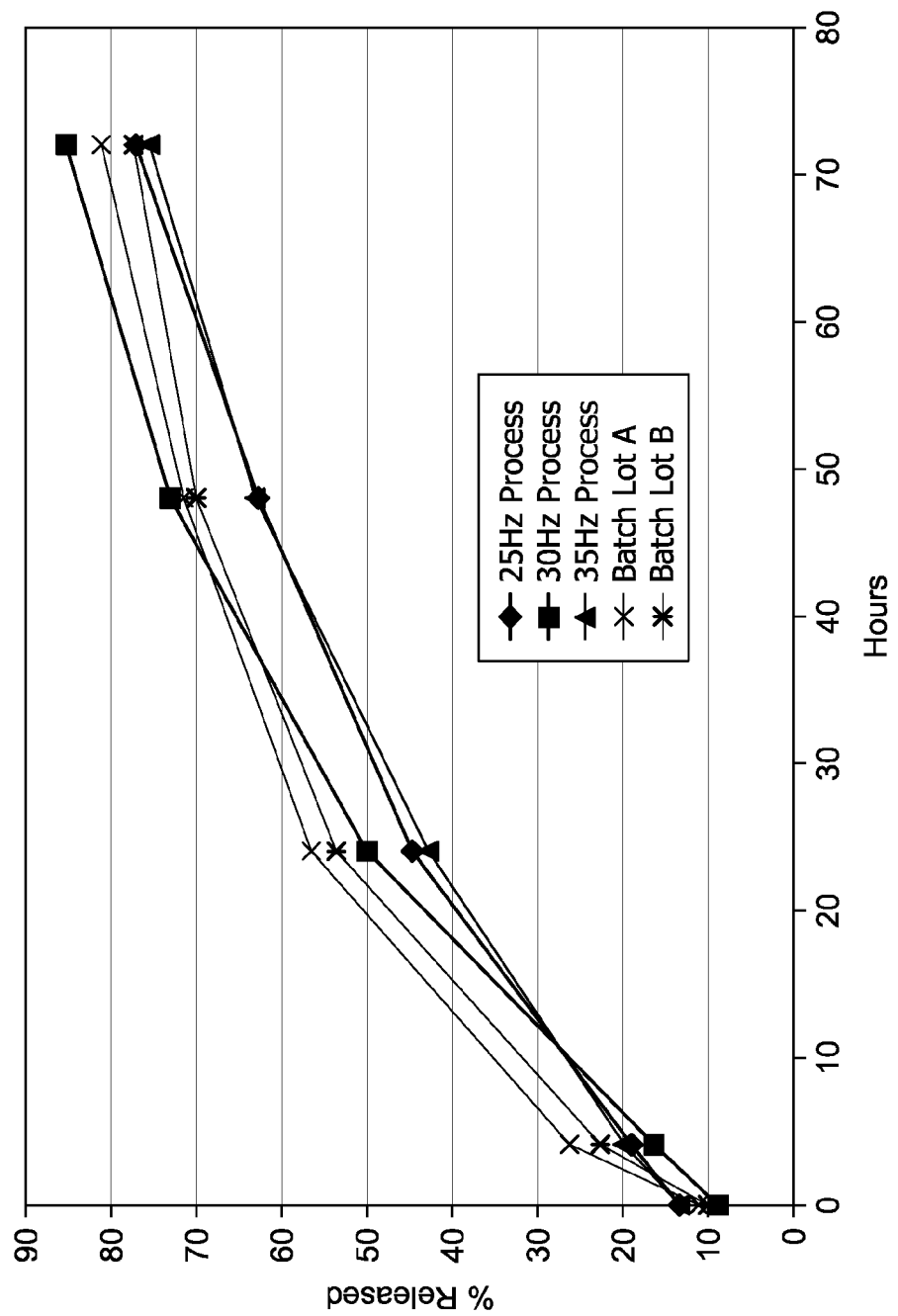
FIG. 12 is a graph of an in vitro release study of multivesicular liposome formulations.
Figure 13:
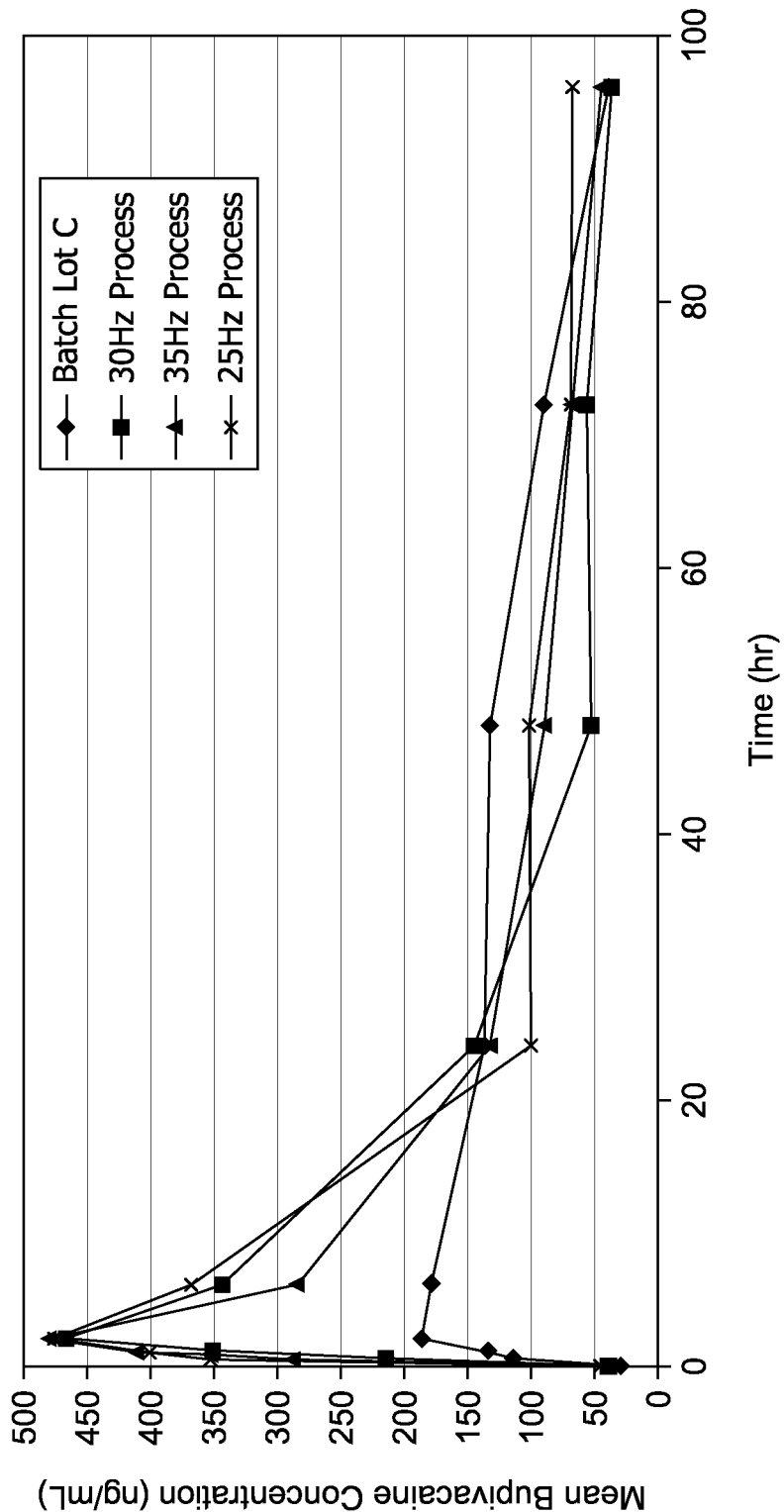
FIG. 13 is a graph of an in vivo PK study of multivesicular liposome formulations.

In another embodiment, any one of the above described embodiments can be used alone or in combination with any one or more of the above described embodiments. For example, any above described atomizing nozzle, evaporation apparatus, continuous-flow emulsification system, continuous-flow diafiltration system, continuous-flow diafiltration further comprising one or more centrifuges, continuous-flow centrifuge system, or continuous processing system can be used alone or in combination. Thus, an evaporation apparatus can be used in conjunction with a three-fluid atomizing nozzle. This evaporation system/atomizing nozzle can be used with a continuous-flow emulsification system, as depicted in FIGS. 1A, 1B, and 1C. The three-fluid atomizing nozzle/evaporation apparatus combination can be used in conjunction with a continuous-flow system, as depicted in FIGS. 8, 10, and 11. Any of these combinations can be used to make multivesicular liposomes. In particular any of the combinations can be used to make multivesicular liposomes containing bupivacaine or its salts as the therapeutic agent.

DETAILED DESCRIPTION OF THE PREFERRED EMBODIMENT

Features of the present disclosure will become more fully apparent from the following description and appended claims, taken in conjunction with the accompanying drawings. It will be understood these drawings depict only certain embodiments in accordance with the disclosure and, therefore, are not to be considered limiting of its scope; the disclosure will be described with additional specificity and detail through use of the accompanying drawings. An apparatus, system or method according to some of the described embodiments can have several aspects, no single one of which necessarily is solely responsible for the desirable attributes of the apparatus, system or method. After considering this discussion, and particularly after reading the section entitled "Detailed Description of the Preferred Embodiment" one will understand how illustrated features serve to explain certain principles of the present disclosure.

In the following detailed description, only certain exemplary embodiments have been shown and described, simply by way of illustration. As those skilled in the art would realize, the described embodiments may be modified in various different ways, all without departing from the spirit or scope of the present disclosure. Accordingly, the drawings and description are to be regarded as illustrative in nature and not restrictive. In addition, when an element is referred to as being "on" another element, it can be directly on the another element or be indirectly on the another element with one or more intervening elements interposed therebetween. Also, when an element is referred to as being "connected to" another element, it can be directly connected to the another element or be indirectly connected to the another element with one or more intervening elements interposed therebetween. Hereinafter, like reference numerals refer to like elements. Since the disclosure may be modified in various ways and have various embodiments, the disclosure will be described in detail with reference to the drawings. However, it should be understood that the disclosure is not limited to a specific embodiment but includes all changes and equivalent arrangements and substitutions included in the spirit and scope of the disclosure. In the following description, if the detailed description of the already known structure and operation may confuse the subject matter of the present disclosure, the detailed description thereof will be omitted.

While such terms as "first," "second," etc., may be used to describe various components, such components must not be limited to the above terms. The above terms are used only to distinguish one component from another. Terms used in the following description are to describe specific embodiments and is not intended to limit the disclosure. The expression of singularity includes plurality meaning unless the singularity expression is explicitly different in context. It should be understood that the terms "comprising," "having," "including," and "containing" are to indicate features, numbers, steps, operations, elements, parts, and/or combinations but not to exclude one or more features, numbers, steps, operations, elements, parts, and/or combinations or additional possibilities.

Some embodiments provide continuous processes for making multivesicular liposomes. Prior methods of making multivesicular liposomes required batch processing. This batch processing required removal of the solvent from the droplets of first emulsion surrounded by a second aqueous phase by contacting the suspension of first emulsion droplets in a continuous aqueous phase with a discontinuous gas phase by sparging (bubbling) gas through the aqueous phase or blowing gas over a flask containing continuous aqueous phase. This batch processing takes tens of minutes to remove the solvent.

It was surprisingly discovered that forming a first emulsion surrounded by an aqueous shell in the form of a droplet and contacting it with a continuous gas phase, reduces the time needed to remove the organic solvent to a few seconds and possibly a fraction of a second. (much less than the tens of minutes stated above for batch processing).

This is due to the tremendous gas contacting surface area of the atomized droplets; and the much faster diffusion of the solvent in gasses versus water; and the very short distances that the solvent has to diffuse through the aqueous phase to reach the gas (now only microns instead of the distanced between sparging bubbles.)

This extremely fast solvent removal enables the continuous processing. The solvent is removed in less than the time that it takes for the atomized droplets to reach the bottom of the solvent removal vessel (a few seconds at most).

Definitions

As used herein, abbreviations are defined as follows:

aq. Aqueous
CIP Clean-in-place processing
° C. Temperature in degrees Celsius
d10 the diameter where 10 mass-% (volume %) (of the particles) of the particles have a smaller equivalent diameter, and the other 90 mass-% (volume %) have a larger equivalent diameter in μm
d50 the diameter where 50 mass-% (volume %) (of the particles) of the particles have a smaller equivalent diameter, and the other 50 mass-% (volume %) have a larger equivalent diameter in μm
d90 the diameter where 90 mass-% (volume %) (of the particles) of the particles have a smaller equivalent diameter, and the other 100 mass-% (volume %) have a larger equivalent diameter in μm
DCM methylene chloride
g Gram(s)
h Hour (hours)
mL Milliliter(s)
mg Milligram(s)
mOsm/kg Osmolality per kilogram
pH measure of the acidity or alkalinity of a liquid using a pH meter or pH indicator
PPV Packed particle volume
PSD Particle size distribution
RT, rt Room temperature
SIP Sterile-in-place processing
Tert, t tertiary
μL Microliter(s)
μg Microgram(s)
WFI Water for injection Some embodiments relate to a process for preparing a large diameter synthetic membrane vesicle composition comprising preparing a first component by mixing a first aqueous phase and an organic phase, said organic phase comprising an organic solvent, at least one amphipathic lipid and at least one neutral lipid; preparing a droplet(s) by mixing said first component and a second aqueous phase, said droplet(s) comprising an aqueous phase; preparing a large diameter synthetic membrane vesicle by removing the organic solvent from the droplet(s), wherein the removing comprises contacting the droplet(s) with a gas; and collecting the large diameter synthetic membrane vesicle particles, wherein the large diameter synthetic membrane vesicle is suspended in a continuous aqueous phase.

Some embodiments relate to a process for preparing a multivesicular liposome composition comprising preparing a first component by mixing a first aqueous phase and an organic phase, said organic phase comprising an organic solvent, at least one amphipathic lipid and at least one neutral lipid, wherein the first component comprises a therapeutic agent; preparing a droplet(s) by mixing said first component and a second aqueous phase, said emulsion droplet(s) comprising an aqueous phase; preparing a multivesicular liposome particle by removing the organic solvent from the emulsion droplet, wherein the removing comprises contacting the emulsion droplet with a gas; and preparing a multivesicular liposome composition by collecting the multivesicular liposome particles, wherein the multivesicular liposome composition is suspended in a continuous aqueous phase.

Some embodiments relate to a process for preparing a multivesicular liposome composition comprising preparing a first component by mixing a first aqueous phase and an organic phase, said organic phase comprising an organic solvent, at least one amphipathic lipid and at least one neutral lipid, wherein the first component comprises a therapeutic agent, preparing an emulsion of first component droplets, a second component droplet, by mixing said first component and a second aqueous phase, said second component droplet comprising an aqueous phase, wherein the second component droplet is prepared using a device as described herein, preparing a multivesicular liposome particle by removing the organic solvent from the second component droplet, wherein the removing comprises contacting the second component droplet with a gas, and preparing a multivesicular liposome composition by collecting the multivesicular liposome particles, wherein the multivesicular liposome composition is suspended in a continuous aqueous phase.

As used herein the term "amphipathic lipid" refers to a substance including a hydrophilic region and a hydrophobic region, such as phospholipids. Amphipathic lipids can be zwitterionic phospholipids, zwitterionic lipids, lipids having a net negative charge, and lipids having a net positive charge. For example, amphipathetic lipids include, but are not limited to, phosphatidylcholines, phosphatidylserines, phosphatidylethanolamines, phosphatidylinositols, sphingomyelin, soybean lecithin (soya lecithin), egg lecithin, lysophosphatidylcholines, lysophosphatidylethanolamines, phosphatidylglycerols, phosphatidylserines, phosphatidylinositols, phosphatidic acids, cardiolipins, acyl trimethylammonium propane, diacyldimethylammonium propane, stearylamine, ethyl phosphatidylcholine and the like. Phospholipids used in the methods described herein can be of a single class or a mixture of classes. Some embodiments include crude preparations of phospholipids, such as soybean lecithin (soya lecithin) and egg lecithin. Soya lecithin is a combination predominantly of naturally-occurring phospholipids; phosphatidylcholine (PC), phosphatidylethanolamine (PE) and phosphatidylinositol (PI). Examples of phosphatidylcholines and phosphatidylglycerols include, but are not limited to, 1,2-dioleoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1,2-diarachidoyl-sn-glycero-3~phosphocholine, 1,2-dibehenoyl-sn-glycero-3-phosphocholine, 1,2-dipalmitoleoyl-sn-glycero-3-phosphocholine, 1,2-dieicosenoyl-sn-glycero-3-phosphocholine, 1,2-dierucoyl-sn-glycero-3-phosphocholine, 1,2-dipalmitoyl-sn-glycero-3-phosphoglycerol, 1,2-dioleoyl-sn-glycero-3-phosphoglycerol, and mixtures thereof.

As used herein the term "neutral lipid" refers to oils, waxes or fatty acid esters that lack a charged or hydrophilic head group. Neutral lipids include but are not limited to, glycerol esters, glycol esters, tocopherol esters, sterol esters, hydrocarbons and squalenes.

As used herein the terms "glycerol esters," "triglycerides," and "triacylglycerols" refer to triesters formed from glycerol and fatty acids. Glycerol esters include but are not limited to, triolein, tripalmitolein, trimyristolein, trilinolein, tributyrin, tricaprylin, tricaproin, and tricaprin.

As used herein the term "organic solvent" refers to ethers, esters, halogenated ethers, aromatic or aliphatic hydrocarbons, aromatic or aliphatic halohydrocarbons, or Freons. Organic solvents include but are not limited to, diethyl ether, tert-butylmethyl ether, tetrahydrofuran, sevoflurane, desflurane, isoflurane, enflurane, halothane, chloroform, dichloromethane, ethyl acetate, hexane, hexanes, cyclohexane, pentane, cyclopentane, petroleum ether, toluene, and any combinations thereof.

As used herein the term "aqueous phase" refers to any solution or mixture having water as the major component. The aqueous phase can include constituents, such as pH buffering agents, salts, osmotic agents, simple sugars, amino acids, electrolytes, preservatives, other water soluble excipients and the like. Aqueous phase constituents can include, but are not limited to, sodium chloride, hydrochloric acid, phosphoric acid, lysine, dextrose, glucose and the like.

As used herein the term "fluid" refers to a substance that has the ability to flow. Fluids can be a gas, a liquid, a liquid with a substance(s) suspended throughout the liquid, an emulsion, a vapor, or a gas/vapor mixture.

As used herein the term "therapeutic agent" and "drug" refers to a chemical compound, mixtures of chemical compounds, or biological molecules, such as biological macromolecules or peptides that may have therapeutic properties. The therapeutic agent can be purified, substantially purified or partially purified. In some embodiments, the therapeutic agent can be selected from the group including antianginas, antiarrhythmics, antiasthmatic agents, antibiotics, antidiabetics, antifungals, antihistamines, antihypertensives, antiparasitics, antineoplastics, antitumor drugs, antivirals, cardiac glycosides, hormones, immunomodulators, monoclonal antibodies, neurotransmitters, nucleic acids, proteins, radio contrast agents, radionuclides, sedatives, analgesics, steroids, tranquilizers, vaccines, vasopressors, anesthetics, peptides and the like. Any pharmaceutically acceptable salt of a particular therapeutic agent is also envisioned as being useful in the present embodiments. In some embodiments, the therapeutic agent can be introduced in either an aqueous or a solvent phase, depending on their solubility in these phases. In a typical embodiment, the therapeutic agent can be selected from the group including semisynthetic aminoglycoside antibiotics such as amikacin; antidiabetics; peptides such as insulin; antitumor drugs such as paclitaxel; antineoplastics including cytarabine, 5-fluorouracil and floxuridine; alkaloid opiate analgesics including morphine and hydromorphine; local anesthetics including bupivacaine; synthetic anti-inflammatory adrenocortical steroids including dexamethasone; antimetabolites including methotrexate; glycopeptide antibiotics including bleomycin; vincaleukoblastines and stathmokinetic oncolytic agents including vincristine and vinblastine; hormones, plasma proteins, cytokines, growth factors, DNA and RNA from a variety of organisms, and antisense oligonucleotides. In some embodiments, the therapeutic agent can be an amide anesthetic. Amide anesthetics include, but are not limited to, bupivacaine, mepivacaine, ropivacaine, lidocaine, pyrrocaine, prilocaine, their stereoisomers, and combinations thereof, and pharmaceutically acceptable salts thereof.

As used herein the term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like. In some embodiments, the therapeutic agent can have a low aqueous solubility in neutral form. In some embodiments, the pharmaceutically acceptable salt of a therapeutic agent can have higher aqueous solubility in comparison to a therapeutic agent in neutral form.

Many and varied therapeutic agents can be incorporated by encapsulation within the synthetic membrane vesicles. A non-limiting list of therapeutic agent classes include, but are not limited to, antianginas, antiarrhythmics, antiasthmatic agents, antibiotics, antidiabetics, antifungals, antihistamines, antihypertensives, antiparasitics, antineoplastics, antiobesity agents, antiviral agents, otologicals, cardiac glycosides, hormones, immunomodulators, monoclonal antibodies, neurotransmitters, sedatives, vaccines, vasopressors, anesthetics, amide anaesthetics, corticosteroids, tricyclic antidepressants, tetracyclic antidepressants, selective serotonin reuptake inhibitors, steroid receptor modulators, antipsychotic drugs, antiprotozoal drugs, opioids, antiproliferative agents, salicylanilides, antihelminthic drugs, vinca alkaloids, anti-inflammatory agents, antidepressants, prostaglandins, phosphodiesterase IV inhibitors; retinoids, steroids, β-adrenergic receptor ligands, anti-mitotic agents, microtubule inhibitors, microtubule-stabilizing agents, serotonin norepinephrine reuptake inhibitors, noradrenaline reuptake inhibitors, non-steroidal immunophilin-dependent immunosuppressants, non-steroidal immunophilin-dependent immunosuppressant enhancers; antimalarial agents, analgesics, immunosuppressants, expectorants, sulfa drugs, cardiovascular drugs, central nervous system (CNS) depressants, H2-blockers, anti-platelet drugs, anticonvulsants, alpha blockers, beta-blockers, cholinesterase inhibitors, calcium channel blockers, H1-receptor antagonists, and proteinaceous materials. The therapeutic agents listed herein can be used in the preparation of medicaments for the treatment of a disease for which the therapeutic agent is known to those of skill in the art to be effective. Therapeutic agents, and diseases for which the therapeutic agent is effective, can be identified by reference to, for example, The Physician's Desk Reference, which is incorporated herein by reference in its entirety.

Examples of proteinaceous materials that can be incorporated into the synthetic membrane vesicles, include but are not limited to, DNA, RNA, proteins of various types, protein hormones produced by recombinant DNA technology effective in humans, hematopoietic growth factors, monokines, lymphokines, tumor necrosis factor, inhibin, tumor growth factor alpha and beta, Mullerian inhibitory substance, nerve growth factor, fibroblast growth factor, platelet-derived growth factor, pituitary and hypophyseal hormones including LH and other releasing hormones.

Examples of antiarrhythmics, include but are not limited to, quinidine, procainamide, disopyramide, ajmaline, lidocaine, tocamide, mexiletine, flecainide, propafenone, moricizine, propranolol, esmolol, timolol, metoprolol, atenolol, amiodarone, sotalol, ibutilide, dofetilide, verapamil, diltiazem, and digoxin.

Examples of antiasthmatic agents, include but are not limited to, salbutamol, levalbuterol, terbutaline, bitolterol, epinephrine, ipratropium bromide, salmeterol, formoterol, bambuterol, and albuterol.

Examples of antibiotics, include but are not limited to, amikacin, gentamicin, kanamycin, neomycin, netilmicin, streptomycin, tobramycin, paromomycin, geldanamycin, herbimycin, loracarbef, ertapenem, doripenem, imipenem, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin, bacitracin, colistin, polymyxin b, ciprofloxacin, enoxacin, gatifloxacin, levofloxacin, lomefloxacin, moxifloxacin, norfloxacin, ofloxacin, trovafloxacin, grepafloxacin, sparfloxacin, mafenide, prontosil, sulfacetamide, sulfamethizole, sulfanilimide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin, rifampin, thiamphenicol, and timidazole.

Examples of antidiabetics, include but are not limited to, tolbutamide, acetohexamide, tolazamide, chlorpropamide, glipizide, glyburide, glimepiride, gliclazide, repaglinide, nateglinide, metformin, rosiglitazone, pioglitazone, troglitazone, miglitol, acarbose, exenatide, liraglutide, taspoglatide, vildagliptin, sitagliptin, GLP-1, and analog to GLP-1.

Examples of antifungals, include but are not limited to, natamycin, rimocidin, filipin, nystatin, amphotericin B, candicin, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole, abafungin, terbinafine, amorolfine, naftifine, butenafine, anidulafungin, caspofungin, micafungin, ciclopirox, tolnaftate, undecylenic acid, 5-fluorocytosine, and griseofulvin.

Examples of antihistamines, include but are not limited to, aceprometazine, alimemazine, astemizole, azatadine, azelastine, benadryl, bepotastine, bisulepine, brompheniramine, chlorcyclizine, chloropyramine, chlorothen, chlorphenamine, cinnarizine, clemastine, clemizole, clobenzepam, clobenztropine, clocinizine, cyclizine, cyproheptadine, dacemazine, dexbrompheniramine, dexchlorpheniramine, diphenhydramine, doxylamine, drixoral, ebastine, embramine, emedastine, epinastine, etymemazine, fexofenadine, homochlorcyclizine, hydroxyzine, iproheptine, isopromethazine, ketotifen, levocabastine, mebhydrolin, mepyramine, methafurylene, methapyrilene, methdilazine, moxastine, p-methyldiphenhydramine, pemirolast, pheniramine, phenyltoloxamine, resporal, rondec, semprex-d, setastine, sominex, talastine, terfenadine, thenyldiamine, thiazinamium, and triprolidine.

Examples of antihypertensives, include but are not limited to, bumetanide, ethacrynic acid, furosemide, torsemidet, epitizide, hydrochlorothiazide, chlorothiazide, bendroflumethiazide, indapamide, chlorthalidone, metolazone, amiloride, triamterene, spironolactone, atenolol, metoprolol, nadolol, oxprenolol, pindolol, propranolol, timolol, doxazosin, phentolamine, indoramin, phenoxybenzamine, prazosin, terazosin, tolazoline, bucindolol, carvedilol, labetalol, clonidine, methyldopa, guanfacine, amlodipine, felodipine, isradipine, lercanidipine, nicardipine, nifedipine, nimodipine, nitrendipine, diltiazem, verapamil, captopril, enalapril, fosinopril, lisinopril, perindopril, quinapril, ramipril, trandolapril, benazepril, candesartan, eprosartan, irbesartan, losartan, olmesartan, telmisartan, valsartan, eplerenone, spironolactone, sodium nitropruside, clonidine, guanabenz, methyldopa, moxonidine, guanethidine, and reserpine.

Examples of antiparasitics, include but are not limited to, mebendazole, pyrantel pamoate, thiabendazole, diethycarbazine, niclosamide, praziquantel, rifampin, amphotericin B, and melarsoprol.

Examples of antineoplastics, include but are not limited to, aclarubicin, altretamine, aminopterin, amrubicin, azacitidine, azathioprine, belotecan, busulfan, camptothecin, capecitabine, carboplatin, carmofur, carmustine, chlorambucil, cisplatin, cladribine, clofarabine, cyclophosphamide, cytarabine, daunorubicin, decitabine, doxorubicin, epirubicin, etoposide, floxuridine, fludarabine, 5-fluorouracil, fluorouracil, gemcitabine, idarubicin, ifosfamide, irinotecan, mechlorethamine, melphalan, mercaptopurine, methotrexate, mitoxantrone, nedaplatin, oxaliplatin, pemetrexed, pentostatin, pirarubicin, pixantrone, procarbazine, pyrimethamine raltitrexed, rubitecan, satraplatin, streptozocin, thioguanine, triplatin tetranitrate, teniposide, topotecan, tegafur, trimethoprim, uramustine, valrubicin, vinblastine, vincristine, vindesine, vinflunine, vinorelbine, and zorubicin.

Examples of antiviral agents, include but are not limited to, abacavir, aciclovir, acyclovir, adefovir, amantadine, amprenavir, arbidol, atazanavir, atripla, boceprevir, cidofovir, combivir, darunavir, delavirdine, didanosine, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, lamivudine, lopinavir, loviride, maraviroc, moroxydine, nelfinavir, nevirapine, nexavir, oseltamivir, penciclovir, peramivir, pleconaril, raltegravir, ribavirin, rimantadine, ritonavir, saquinavir, stavudine, tenofovir, tenofovir disoproxil, tipranavir, trifluridine, trizivir, tromantadine, valaciclovir, valganciclovir, vicriviroc, vidarabine, viramidine, zalcitabine, zanamivir, and zidovudine.

Examples of otologicals, include but are not limited to, betamethasone, chloramphenicol, chlorhexidine, clioquinol, dexamethasone, gentamicin, hydrocortisone, lidocaine, miconazole, neomycin, nitrofural, polymyxin b, prednisolone, rifamycin, and tetracycline.

Examples of cardiac glycosides, include but are not limited to, digitoxin, digoxin, and deslanoside.

Examples of hormones, include but are not limited to, adiponectin, adrenocorticotropic hormone, aldosterone, androstenedione, angiotensinogen, angiotensin, antidiuretic hormone, antimullerian hormone, atrial-natriuretic peptide, brain natriuretic peptide, 25-hydroxyvitamin $D_3$, calcitonin, 1,25-dihydroxyvitamin $D_3$, cholecystokinin, corticotropin-releasing hormone, cortisol, dehydroepiandrosterone, dihydrotestosterone, dopamine, endothelin, enkephalin, epinephrine, erythropoietin, estradiol, estriol, estrone, follicle-stimulating hormone, gastrin, ghrelin, glucagon, gonadotropin-releasing hormone, growth hormone, growth hormone-releasing hormone, histamine, human chorionic gonadotropin, human placental lactogen, inhibin, insulin, insulin-like growth factor, leptin, leukotrienes, lipotropin, luteinizing hormone, melanocyte stimulating hormone, melatonin, neuropeptide y, norepinephrine, orexin, oxytocin, pancreatic polypeptide, parathyroid hormone, progesterone, prolactin, prolactin releasing hormone, prostacyclin, prostaglandins, relaxin, renin, secretin, serotonin, somatostatin, testosterone, thrombopoietin, thromboxane, thyroid-stimulating hormone, thyrotropin-releasing hormone, thyroxine, and triiodothyronine.

Examples of immunomodulators, include but are not limited to, abatacept, abetimus, adalimumab, afelimomab, aflibercept, afutuzolimab, alefacept, anakinra, aselizumab, atlizumab, atorolimumab, azathioprine, basiliximab, belatacept, belimumab, bertilimumab, cedelizumab, clenoliximab, certolizumab pegol, ciclosporin, daclizumab, deforolimus, dorlimomab aritox, dorlixizumab, efalizumab, erlizumab, elsilimomab, etanercept, everolimus, faralimomab, fontolizumab, galiximab, gantenerumab, gavilimomab golimumab, gomiliximab, gusperimus, infliximab, inolimomab, ipilimumab keliximab, lebrilizumab, leflunomide, lenalidomide, lerdelimumab, lumiliximab, maslimomab, mepolizumab, metelimumab, methotrexate, morolimumab, muromonab-cd3, mycophenolic acid, natalizumab, nerelimomab, ocrelizumab, odulimomab, omalizumab, otelixizumab, pascolizumab, pexelizumab, pimecrolimus, reslizumab, rilonacept, rovelizumab, ruplizumab, siplizumab, sirolimus, tacrolimus, talizumab, telimomab aritox, temsirolimus, teneliximab, teplizumab, teriflunomide, thalidomide, tocilizumab, toralizumab, tremelimumab, ustekinumab, vapaliximab, vepalimomab, visilizumab, zanolimumab, ziralimumab, zolimomab aritox, zotarolimus, and tetrachlorodecaoxide.

Examples of monoclonal antibodies, include but are not limited to, abagovomab, abatacept, abciximab, adalimumab, adecatumumab, aflibercept, afutuzumab, alacizumab pegol, alemtuzumab, altumomab, afelimomab, anatumomab mafenatox, anrukinzumab, apolizumab, arcitumomab, aselizumab, atlizumab, atorolimumab, bapineuzumab, basiliximab, bavituximab, bectumomab, belatacept, belimumab, bertilimumab, besilesomab, bevacizumab, biciromab bralobarbital, bivatuzumab mertansine, blinatumomab, briakinumab, canakinumab, cantuzumab mertansine, capromab pendetide, catumaxomab, cedelizumab, certolizumab pegol, cetuximab, citatuzumab bogatox, cixutumumab, clenoliximab, golimumab, ustekinumab, conatumumab, dacetuzumab, dacliximab, daclizumab, denosumab, detumomab, dorlimomab aritox, dorlixizumab, ecromeximab, eculizumab, edobacomab, edrecolomab, efalizumab, efungumab, elsilimomab, enlimomab pegol, epitumomab cituxetan, epratuzumab, erlizumab, ertumaxomab, etanercept, etaracizumab, exbivirumab, fanolesomab, faralimomab, felvizumab, fezakinumab, figitumumab, fontolizumab, foravirumab, galiximab, gantenerumab, gavilimomab, gemtuzumab ozogamicin, golimumab, gomiliximab, ibalizumab, ibritumomab tiuxetan, igovomab, imciromab, infliximab, intetumumab, inolimomab, inotuzumab ozogamicin, ibalizumab, ipilimumab, iratumumab, keliximab, labetuzumab, lemalesomab, lebrilizumab, lerdelimumab, lexatumumab, libivirumab, lintuzumab, lucatumumab, lumiliximab, mapatumumab, maslimomab, matuzumab, mepolizumab, metelimumab, milatuzumab, minretumomab, mitumomab, morolimumab, motavizumab, muromonab, stamulumab, nacolomab tafenatox, naptumomab estafenatox, natalizumab, nebacumab, necitumumab, nerelimomab, nimotuzumab, nofetumomab merpentan, ocrelizumab, odulimomab, ofatumumab, omalizumab, oportuzumab monatox, oregovomab, otelixizumab, pagibaximab, palivizumab, panitumumab, panobacumab, pascolizumab, pemtumomab, pertuzumab, pexelizumab, pintumomab, priliximab, pritumumab, rafivirumab, ramucirumab, ranibizumab, raxibacumab, regavirumab, reslizumab, rilonacept, rilotumumab, rituximab, robatumumab, rovelizumab, rozrolimupab, ruplizumab, satumomab, sevirumab, sibrotuzumab, siltuximab, siplizumab, solanezumab, sonepcizumab, sontuzumab, stamulumab, sulesomab, tacatuzumab tetraxetan, tadocizumab, talizumab, tanezumab, taplitumomab paptox, tefibazumab, telimomab aritox, tenatumomab, teneliximab, teplizumab, ticilimumab, tigatuzumab, tocilizumab, toralizumab, tositumomab, trastuzumab, tremelimumab, tucotuzumab celmoleukin, tuvirumab, urtoxazumab, ustekinumab, vapaliximab, vedolizumab, veltuzumab, vepalimomab, visilizumab, volociximab, votumumab, zalutumumab, zanolimumab, ziralimumab, and zolimomab aritox.

Examples of neurotransmitters, include but are not limited to, acetylcholine, adenosine, adenosine-5'-triphosphate, aspartate, norepinephrine, dopamine, glycine, serotonin, melatonin, histamine, glutamate, gamma aminobutyric acid, and guanosine-5'-triphosphate.

Examples of sedatives, include but are not limited to, alprazolam, amobarbital, carisoprodol, chlordiazepoxide, clomethiazole, clonazepam, diazepam, diphenhydramine, estazolam, eszopiclone, ethchlorvynol, flunitrazepam, gamma-hydroxybutyrate, glutethimide, ketamine, lorazepam, methaqualone, methyprylon, midazolam, nitrazepam, oxazepam, pentobarbital, phenobarbitoltriazolam, ramelteon, secobarbital, temazepam, thalidomide, zaleplon, zolpidem, and zopiclone.

Examples of vaccines, include but are not limited to, measles vaccine, mumps vaccine, rubella vaccine, varicella vaccine, inactivated polio vaccine, inactivated influenza vaccine, influenza a virus subtype H1N1 vaccine, diphtheria toxoid vaccine, tetanus toxoid vaccine, *haemophilus influenzae* type B vaccine, hepatitis B vaccine, hepatitis A vaccine, and pneumoccocal conjugate vaccine.

Examples of vasopressors, include but are not limited to, epinephrine, phenylephrine, dobutamine, isoproterenol, norepinephrine, aceprometazine, alimemazine, astemizole, azatadine, azelastine, benadryl, bepotastine, bisulepine, brompheniramine, chlorcyclizine, chloropyramine, chlorothen, chlorphenamine, cinnarizine, clemastine, clemizole, clobenzepam, clobenztropine, clocinizine, cyclizine, cyproheptadine, dacemazine, dexbrompheniramine, dexchlorpheniramine, diphenhydramine, doxylamine, drixoral, ebastine, embramine, emedastine, epinastine, etymemazine, fexofenadine, homochlorcyclizine, hydroxyzine, iproheptine, isopromethazine, ketotifen, levocabastine, mebhydrolin, mepyramine, methafurylene, methapyrilene, methdilazine, moxastine, p-methyldiphenhydramine, pemirolast, pheniramine, phenyltoloxamine, resporal, rondec, semprex-d, setastine, sominex, talastine, terfenadine, thenyldiamine, thiazinamium, and triprolidine.

Examples of anesthetics, include but are not limited to, propofol, etomidate, methohexital and sodium thiopental, midazolam, diazepam, and ketamine, benzocaine, chloroprocaine, cocaine, cyclomethycaine, dimethocaine, propoxycaine, procaine, proparacaine, tetracaine, articaine, bupivacaine, carticaine, dibucaine, etidocaine, levobupivacaine, lidocaine, mepivacaine, piperocaine, prilocaine, ropivacaine, trimecaine, saxitoxin, and tetrodotoxin.

Examples of amide anesthetics, include but are not limited to, articaine, bupivacaine, carticaine, dibucaine, etidocaine, levobupivacaine, lidocaine, mepivacaine, piperocaine, prilocaine, ropivacaine, and trimecaine.

Examples of corticosteroids, include but are not limited to, hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate.

Examples of tricyclic antidepressants, include but are not limited to, amitriptyline, butriptyline, clomipramine, dosulepin, doxepin, imipramine, lofepramine, trimipramine, desipramine, nortriptyline, and protriptyline.

Examples of tetracyclic antidepressants, include but are not limited to, amoxapine, maprotiline, mianserin, mirtazapine, and setiptiline.

Examples of selective serotonin reuptake inhibitors, include but are not limited to, citalopram, dapoxetine, escitalopram, fluoxetine, fluvoxamine, paroxetine, sertraline, vilazodone, and zimelidine.

Examples of antipsychotic drugs, include but are not limited to, haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, chlorprothixene, flupenthixol, thiothixene, zuclopenthixol, clozapine, olanzapine, risperidone, quetiapine, ziprasidone, amisulpride, asenapine, paliperidone, aripiprazole, and bifeprunox.

Examples of antiprotozoal drugs, include but are not limited to, eflornithine, furazolidone, melarsoprol, metronidazole, ornidazole, paromomycin sulfate, pentamidine, pyrimethamine, and tinidazole.

Examples of opioids, include but are not limited to, endorphins, enkephalins, dynorphins, endomorphins, codeine, morphine, thebaine, oripavine, diacetylmorphine, dihydrocodeine, hydrocodone, hydromorphone, nicomorphine, oxycodone, oxymorphone, fentanyl, alphamethylfentanyl, alfentanil, sufentanil, remifentanil, carfentanyl, ohmefentanyl, pethidine, ketobemidone, allylprodine, prodine, propoxyphene, dextropropoxyphene, dextromoramide, bezitramide, piritramide, methadone, dipipanone, levomethadyl acetate, loperamide, diphenoxylate, dezocine, pentazocine, phenazocine, buprenorphine, dihydroetorphine, etorphine, butorphanol, nalbuphine, levorphanol, levomethorphan, lefetamine, meptazinol, tilidine, tramadol, tapentadol, nalmefene, naloxone, and naltrexone.

Examples of antiproliferative agents, include but are not limited to, aclarubicin, altretamine, aminopterin, amrubicin, azacitidine, azathioprine, belotecan, busulfan, camptothecin, capecitabine, carboplatin, carmofur, carmustine, chlorambucil, cisplatin, cladribine, clofarabine, cyclophosphamide, cytarabine, daunorubicin, decitabine, docetaxel, doxorubicin, epirubicin, etoposide, floxuridine, fludarabine, 5-fluorouracil, fluorouracil, gemcitabine, idarubicin, ifosfamide, irinotecan, mechlorethamine, melphalan, mercaptopurine, methotrexate, mitoxantrone, nedaplatin, oxaliplatin, paclitaxel, pemetrexed, pentostatin, pirarubicin, pixantrone, procarbazine, pyrimethamine raltitrexed, rubitecan, satraplatin, sirolimus, streptozocin, thioguanine, triplatin tetranitrate, teniposide, topotecan, tegafur, trimethoprim, uramustine, valrubicin, vinblastine, vincristine, vindesine, vinflunine, vinorelbine, and zorubicin.

Examples of salicylanilides, include but are not limited to, niclosamide, oxyclozanide, and rafoxanide.

Examples of antihelminthic drugs, include but are not limited to, abamectin, albendazole, diethylcarbamazine, mebendazole, niclosamide, ivermectin, suramin, thiabendazole, pyrantel pamoate, levamisole, praziquantel, triclabendazole, flubendazole, fenbendazole, emodepside, and monepantel.

Examples of vinca alkaloids, include but are not limited to, vinblastine, vincristine, vindesine and vinorelbine.

Examples of anti-inflammatory agents, include but are not limited to, phenylbutazone, mofebutazone, oxyphenbutazone, clofezone, kebuzone, indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, piroxicam, tenoxicam, droxicam, lornoxicam, meloxicam, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, mefenamic acid, tolfenamic acid, flufenamic acid, meclofenamic acid, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, and chondroitin sulfate.

Examples of cancers that can be treated with an anticancer agent include, but are not limited to, head and neck cancer, breast cancer, colorectal cancer, gastric cancer, hepatic cancer, bladder cancer, cervical cancer, endometrial cancer, lung cancer (non-small cell), ovarian cancer, pancreatic cancer, prostate cancer; choriocarcinoma (lung cancer); hairy cell leukemia, chronic lymphotic leukemia, acute lymphocytic leukemia (breast & bladder), acute myelogenous leukemia, Hodgkin's lymphoma, non-Hodgkin's lymphoma (osteogenic sarcoma, adult soft tissue sarcoma), meningeal leukemia, multiple myeloma, chronic myelogenous leukemia, erythroleukemia, and T-cell lymphoma.

Examples of inflammatory and autoimmune diseases that can be treated with an inflammatory agent include, but are not limited to, B cell disorders, T cell disorders, rheumatoid arthritis (RA), systemic lupus erythematosus (SLE), Sjogren's syndrome, immune thrombocytopenic purpura (ITP), multiple sclerosis (MS), myasthenia Gravis (MG), Graves disease, psoriasis, Hashimoto's disease, immune thrombocytopenic purpura, scleroderma, and inflamatory bowel disease (e.g. Crohn's disease and ulcerative colitis).

In some embodiments, the therapeutic agent can be used singly or in combination with the limitation that the amount of the physiologically active substance in the pharmaceutical composition be sufficient to enable the diagnosis of, prophylaxis against, or treatment of an undesired condition in a living being. In some embodiments, the pharmaceutical compositions can be administered to a living being by any desired route, for example, intramuscular, intra articular, epidural, intraperitoneal, subcutaneous, intra lymphatic, oral, submucosal, transdermal, rectal, vaginal, intranasal, intraocular, and by implantation under different kinds of epithelia, including the bronchial epithelia, the gastrointestinal epithelia, the urogenital epithelia, and the various mucous membranes of the body. Generally, the dosage will vary with the age, condition, sex and extent of the undesired condition in the patient, and can be determined by one skilled in the art. In some embodiments, the dosage range appropriate for human use includes a range of from 0.1 to 6,000 mg of the therapeutic agent per square meter of surface area. Alternate dosage range can be based on weight instead of surface area. In one embodiment, a human dosage of bupivacaine can be 50-1,000 mg, 100-600 mg 100-350 mg. For example, the human dosage of bupivacaine can be approximately 300 mg.

Methods of Preparation

Some embodiments relate to a process for preparing a large diameter synthetic membrane vesicle(s) composition comprising the steps of, forming a first component by mixing a first aqueous phase and an organic phase, said organic phase comprising an organic solvent, at least one amphipathic lipid, and at least one neutral lipid, encapsulating said first component in a second aqueous phase to provide a second component using an atomizing nozzle as disclosed and described herein, said second component comprising an aqueous phase, removing the organic solvent from the second component to form a composition of large diameter synthetic membrane vesicle particles, wherein the removing can be accomplished by contacting the second component with a gas, optionally heating and optionally filtering the composition by particle concentration. Such steps may be combined with other steps. In some embodiments the lipid phase can include cholesterol. In some embodiments, the organic solvent can be a volatile water-immiscible or sparingly miscible solvent. In some embodiments, the first component can be a first emulsion. In some embodiments, the second component can be a second emulsion. In some embodiments, the second component can be a droplet. In some embodiments, the large diameter synthetic membrane vesicle(s) can be multivesicular liposomes.

Some embodiments relate to a process for preparing a large diameter synthetic membrane vesicle(s) composition comprising the steps of, forming a first component by mixing a first aqueous phase and an organic phase, said organic phase comprising an organic solvent, at least one amphipathic lipid, and at least one neutral lipid, encapsulating said first component in a second aqueous phase to provide a second component, said second component comprising an aqueous phase, removing the organic solvent from the second component to form a composition of large diameter synthetic membrane vesicle particles, wherein the removing can be accomplished by using a solvent removal chamber as disclosed and described herein, and optionally filtering the composition by particle concentration. Such steps may be combined with other steps. In some embodiments the lipid phase can include cholesterol. In some embodiments, the organic solvent can be a volatile water-immiscible or sparingly miscible solvent. In some embodiments, the first component can be a first emulsion. In some embodiments, the second component can be a second emulsion. In some embodiments, the second component can be a droplet. In some embodiments, the large diameter synthetic membrane vesicle(s) can be multivesicular liposomes.

Some embodiments relate to a process for preparing a large diameter synthetic membrane vesicle(s) composition comprising the steps of, forming a first component by mixing a first aqueous phase and an organic phase, said organic phase comprising an organic solvent, at least one amphipathic lipid, and at least one neutral lipid, encapsulating said first component in a second aqueous phase to provide a second component using an atomizing nozzle as disclosed and described herein, said second component comprising an aqueous phase, removing the organic solvent from the second component to form a composition of large diameter synthetic membrane vesicle particles, wherein the removing can be accomplished by using a solvent removal chamber as disclosed and described herein, and optionally filtering the composition by particle concentration. Such steps may be combined with other steps. In some embodiments the lipid phase can include cholesterol. In some embodiments, the organic solvent can be a volatile water-immiscible or sparingly miscible solvent. In some embodiments, the first component can be a first emulsion. In some embodiments, the second component can be a second emulsion. In some embodiments, the second component can be a droplet. In some embodiments, the large diameter synthetic membrane vesicle(s) can be multivesicular liposomes.

Some embodiments relate to a process for preparing a multivesicular liposome composition comprising the steps of, forming a first component by mixing a first aqueous phase and an organic phase, said organic phase comprising a volatile water-immiscible or sparingly miscible solvent, at least one amphipathic lipid, and at least one neutral lipid, encapsulating said first component in a second aqueous phase to provide a second component, said second component comprising an aqueous phase, removing the volatile water-immiscible or sparingly miscible solvent from the second component to form a composition of MVL particles, wherein the removing can be accomplished by contacting the second component with a gas, and optionally filtering the multivesicular liposome composition by particle concentration. Such steps may be combined with other steps. In some embodiments the lipid phase can include cholesterol.

First Component

In embodiments that include a first component, the first component can be formed by mixing two phases, such as an organic phase and a first aqueous phase. In some embodiments, a therapeutic agent can be added to the organic phase. In some embodiments, a therapeutic agent can be added to the first aqueous phase. In some embodiments, a therapeutic agent can be added to both the organic phase and the first aqueous phase. In some embodiments, the organic phase can include at least one amphipathic lipid, at least one neutral lipid, and an organic solvent. In some embodiments, the therapeutic agent can be in the form of a pharmaceutically acceptable salt.

In some embodiments, the mixing of the two phases can be accomplished using ultrasound. In some embodiments, the mixing of the two phases can be accomplished using high pressure emulsification. Such emulsification utilizes an atomizing nozzle as disclosed and described herein. In some embodiments, the mixing of the two phases can be accomplished using mechanical processes including using high-shear type devices, rotor/stator and homogenizers, shear-type mixer, static mixer, impeller, porous pipe, any of the disclosed mechanical processes optionally in combination with a heat exchanger, or other processes known to produce water-in-oil emulsions. In some embodiments, the mixing of the two phases can be accomplished using a combination of ultrasound and high pressure emulsification. In some embodiments, the mixing of the two phases can be accomplished using a combination of mechanical processes performed by a device selected from the group consisting of high-shear type devices, rotor/stator mixers and homogenizers, shear-type mixer, static mixer, impeller, porous pipe, high energy vibration, injection into a high velocity liquid stream such as in an aspirator, and the like.

In some embodiments, the first component can comprise particles having an average diameter in the range from about 0.1 μm to about 100 μm. For example, the particles can have an average diameter of at least about 0.1 μm, 1 μm, 5 μm, 10 μm, 15 μm, 20 μm, 50 μm, or 100 μm, or a diameter within a range defined by any of two of the preceding values. In some embodiments, the particles can have an average diameter in the range from about 0.2 μm to about 100 μm, from about 0.2 μm to about 50 μm, from about 0.5 μm to about 30 μm, from about 0.5 μm to about 10 μm, from about 10 μm to about 50 μm, from about 15 μm to about 45 μm, or from about 20 μm to about 40 μm. In a typical embodiment, the particles can have an average diameter in the range of from about 0.5 μm to about 3 μm.

In some embodiments, the first component can be formed at a temperature in the range from about −5° C. to about 99° C., from about 0° C. to about 60° C., from about 2° C. to about 40° C., from about 4° C. to about 20° C., from about 5° C. to about 50° C., from about 10° C. to about 40° C., or from about 15° C. to about 35° C., or from about 10° C. to about 20° C.

In some embodiments, the organic solvent can be selected from the group consisting of diethyl ether, tert-butylmethyl ether, tetrahydrofuran, sevoflurane, desflurane, isoflurane, and enflurane. In some embodiments, the organic solvent can be selected from the group consisting of halothane, chloroform, and dichloromethane. In some embodiments, the organic solvent can be selected from the group consisting of ethyl acetate, hexane, hexanes, cyclohexane, pentane, cyclopentane, petroleum ether, and toluene. In some embodiments, the organic solvent can be selected from the group consisting of freons, chlorofluorocarbons (CFCs) and hydrochlorofluorocarbons (HCFCs) with boiling points above 15° C. In a typical embodiment, the organic solvent can be selected from the group consisting of chloroform, and dichloromethane. For example, the organic solvent can be dichloromethane.

In some embodiments, the first aqueous phase can be selected from the group consisting of water solutions including one or more components selected from the group consisting of a therapeutic agent, dextrose, lysine, dextrose/lysine, sodium chloride, hydrochloric acid, phosphoric acid, an osmotic pressure adjusting agent such as a sugar, dextrose, sucrose, trehalose, fructose, sorbitan, glycerol, or manitol, a therapeutic agent solubility enhancer, and pH modifying agents such as sodium hydroxide, arginine, histidine, sodium borate, acids, bases, (hydroxymethyl)aminomethane, or Good's buffers. In some embodiments, the concentration of any one component in the aqueous phase, other than the therapeutic agent, can be in the range from about 1 μM to about 1 M, from about 1 mM to about 500 mM, from about 10 mM to about 400 mM, from about 100 mM to about 300 mM. In a typical embodiment, any one therapeutic agent component if used in the first aqueous phase can be in the range from about 1 mM to about 1 M. For example, the therapeutic agent component can be approximately 200 mM. In a typical embodiment, the concentration of any one component in the first aqueous phase can be in the range from about 100 mM to about 300 mM. For example, the concentration can be 200 mM. In some embodiments, the first aqueous phase can include phosphoric acid as a component. In some embodiments, the concentration of phosphoric acid can be in the range from about 1 μM to about 1 M, from about 10 μM to about 750 mM, from about 1 mM to about 500 mM or from about 10 mM to about 250 mM. In a typical embodiment, the concentration of phosphoric acid can be in the range from about 100 mM to about 300 mM. For example, the concentration of phosphoric acid can be 200 mM.

In some embodiments, the organic phase can include an amphipathic lipid. In some embodiments, the amphipathic lipid can be selected from the group consisting of soya lecithin, 1,2-dioleoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1,2-diarachidoyl-sn-glycero-3-phosphocholine, 1,2-dibehenoyl-sn-glycero-3-phosphocholine, 1,2-dipalmitoleoyl-sn-glycero-3-phosphocholine, 1,2-dieicosenoyl-sn-glycero-3-phosphocholine, 1,2-dierucoyl-sn-glycero-3-phosphocholine, 1,2-dipalmitoyl-sn-glycero-3-phosphoglycerol, 1,2-dioleoyl-sn-glycero-3-phosphoglycerol, and mixture thereof. In a typical embodiment, the amphipathic lipid can be selected from the group consisting of 1,2-dierucoyl-sn-glycero-3-phosphocholine (DEPC), 1,2-dipalmitoyl-sn-glycero-3-phosphoglycerol (DPPG) and mixtures thereof. For example, the amphipathic lipid can be a mixture of 1,2-dierucoyl-sn-glycero-3-phosphocholine (DEPC) and 1,2-dipalmitoyl-sn-glycero-3-phosphoglycerol (DPPG). In some embodiments the ratio of 1,2-dierucoyl-sn-glycero-3-phosphocholine (DEPC) to 1,2-dipalmitoyl-sn-glycero-3-phosphoglycerol (DPPG) can be in the range from about 100:1 to about 1:10, from about 50:1 to about 1:1, from about 25:1 to about 2:1, from about 15:1 to about 10:1, from about 10:1 to about 30:1, or from about 15:1 to about 20:1. For example, the ratio of 1,2-dierucoyl-sn-glycero-3-phosphocholine (DEPC) to 1,2-dipalmitoyl-sn-glycero-3-phosphoglycerol (DPPG) can be about 16.8:1.

In some embodiments, the organic phase can include a neutral lipid. In some embodiments, the neutral lipid can be selected from the group consisting of triolein, tripalmitolein, trimyristolein trilinolein, tributyrin, tricaprylin, tricaproin, and tricaprin, and mixture thereof. In a typical embodiment, the neutral lipid can be selected from the group consisting of tricaprylin, tricaproin, and tricaprin, and mixtures thereof. For example, the neutral lipid can be tricaprylin. In some embodiments the ratio of amphipathic lipid to neutral lipid can be in the range from about 50:1 to about 1:5, from about 25:1 to about 1:2, from about 15:1 to about 1:1, from about 10:1 to about 2:1 or from about 6:1 to about 3:1. For example, the ratio of amphipathic lipid to neutral lipid can be about 4.4:1.

In some embodiments, the organic phase can include cholesterol. In some embodiments the ratio of amphipathic lipid to cholesterol can be in the range from about 50:1 to about 1:10, from about 25:1 to about 1:5, from about 10:1 to about 1:2, from about 5:1 to about 1:1 or from about 3:1 to about 1.5:1. For example, the ratio of amphipathic lipid to cholesterol can be about 1.8:1. In some embodiments the ratio of cholesterol to neutral lipid can be in the range from about 50:1 to about 1:10, from about 25:1 to about 1:5, from about 10:1 to about 1:2, from about 5:1 to about 1:1 or from about 3:1 to about 2:1. For example, the ratio of cholesterol to neutral lipid can be about 2.4:1. In a typical embodiment, any one therapeutic agent component if used in the organic phase can be in the range from about 1 mM to about 1 M. For example, the therapeutic agent component can be approximately 200 mM.

In some embodiments, the aqueous phase or organic phase can comprise the therapeutic agent. In a typical embodiment, the therapeutic agent can be selected from the group including semisynthetic aminoglycoside antibiotics such as amikacin; antidiabetics; peptides such as insulin; antitumor drugs such as paclitaxel; antineoplastics including cytarabine, 5-fluorouracil and floxuridine; alkaloid opiate analgesics including morphine and hydromorphine; local anesthetics including bupivacaine; synthetic anti-inflammatory adrenocortical steroids including dexamethasone; antimetabolites including methotrexate; glycopeptide antibiotics including bleomycin; vincaleukoblastines and stathmokinetic oncolytic agents including vincristine and vinblastine; hormones, plasma proteins, cytokines, growth factors, DNA and RNA from a variety of organisms, and antisense oligonucleotides. In some embodiments, the therapeutic agent can be an amide anesthetic. In some embodiments, the therapeutic agent can be selected from the group consisting of bupivacaine, mepivacaine, ropivacaine, lidocaine, pyrrocaine, prilocaine, their stereoisomers, and combinations thereof. In a typical embodiment, the therapeutic agent can be bupivacaine or a therapeutically acceptable salt thereof. For example, bupivacaine can be a free base. In some embodiments, the aqueous phase can comprise an acid in sufficient quantity to maintain the bupivacaine or a therapeutically or pharmaceutically acceptable salt thereof in the first aqueous phase.

In some embodiments, the first component can be formed by mixing two phases. In some embodiments, the first component can be an emulsion. In some embodiments, the first component can be in the form of droplets. In some embodiments, the first component droplets can be formed by mixing two phases, such as an organic phase and a first aqueous phase where the speed of mixing can control the size of the first component droplets. In some embodiments, the size of the first component droplets can have an average diameter of at least about 0.1 µm, 1 µm, 5 µm, 10 µm, 15 µm, 20 µm, 50 µm, or 1000 µm, or a diameter within a range defined by any of two of the preceding values. In some embodiments, the average first component droplet size can be preferably between 0.5 µm and 2 µm. For example, the first component droplet size can be approximately 1 µm. In some embodiments, the first component droplet can be an emulsion droplet.

Second Component Droplet

In some embodiments, the first component can then be combined with a second aqueous phase to provide a second component droplet. The second component droplet can be formed by combining the first component with the second aqueous phase using a three-fluid nozzle to form a first component/second aqueous phase mixture. In some embodiments, the first fluid applied to the nozzle is a first liquid, made up of a first component, the second fluid applied to the nozzle is a second liquid made up of a second aqueous phase, and the third fluid can be considered to be a gas (or a gas/vapor mixture), such as nitrogen gas (or a nitrogen gas/aqueous vapor mixture) or air scrubbed of $CO_2$, or air free of, or substantially free of $CO_2$. In some embodiments, contacting the first component/second aqueous phase mixture with the third fluid creates the second component droplets as the gas acts to shear the first emulsion/second aqueous phase mixture into droplets. In some embodiments, the volume:volume ratio of first component to second aqueous phase can be in the range of from about 1:1000 to about 1000:1, in the range of from about 1:500 to about 500:1, in the range of from about 1:50 to about 50:1, in the range of from about 1:10 to about 5:1, or in the range of from about 1:5 to about 5:1. In a typical embodiment, the volume:volume ratio of first component to second aqueous phase can be in the range of from about 1:3 to about 3:1. Alternately, the volume:volume ratio of first component to second aqueous phase can be in the range of from about 2:1 to 1:2. For example, the volume:volume ratio of first component to second aqueous phase can be about 1:1. In some embodiments, the first component can be an emulsion.

In some embodiments, the second aqueous phase can be selected from the group consisting of water solutions of, a therapeutic agent, or pharmaceutically acceptable salt thereof, dextrose, lysine, dextrose/lysine, sodium chloride, hydrochloric acid, phosphoric acid, an osmotic pressure adjusting agent such as a sugar, dextrose, sucrose, trehalose, fructose, sorbitan, glycerol, or manitol, a therapeutic agent solubility enhancer, pH modifying agents such as sodium hydroxide, arginine, histidine, sodium borate, acids, bases, (hydroxymethyl)aminomethane, or Good's buffers, and mixtures thereof. In some embodiments, the concentration of any one component in the second aqueous phase can be in the range from about 1 µM to about 1 M, from about 10 µM to about 750 mM, from about 100 µM to about 500 mM, 1 mM to about 250 mM, from about 10 mM to about 150 mM, from about 50 mM to about 125 mM, from about 100 mM to about 200 mM, from about 100 mM to about 500 mM, or from about 200 mM to about 400 mM. In a typical embodiment, the concentration of any one component in the second aqueous phase can be in the range from about 50 mM to about 270 mM.

In some embodiments, the second aqueous phase can be an aqueous dextrose/lysine solution. In some embodiments, the concentration of dextrose can be in the range from about 1 mM to about 500 mM from about 10 mM to about 300 mM, from about 25 mM to about 200 mM or from about 50 mM to about 150 mM. In a typical embodiment, the concentration of dextrose can be in the range from about 60 mM to about 90 mM. For example, the concentration of dextrose can be about 80 mM. In some embodiments, the concentration of lysine can be in the range from about 1 mM to about 750 mM, from about 10 mM to about 500 mM, from about 50 mM to about 400 mM or from about 100 mM to about 200 mM. In a typical embodiment, the concentration of lysine can be in the range from about 150 mM to about 250 mM. For example, the concentration of lysine can be about 200 mM.

In some embodiments, a first component can be mixed with a second organic phase comprising one or more second amphipathic lipids prior to combination with a second aqueous phase to provide a second component. In some embodiments, the second component can be in the form of droplets. For example, the second organic phase can include the same or different amphipathic lipids than in the first component. The second component droplet can be formed by combining the first component with the second aqueous phase using a three fluid nozzle with an additional inlet for the second organic phase. The second organic phase can alternatively be pumped into the conduit feeding first component to the three fluid nozzle with an optional static mixer in the conduit between the point of second organic phase addition and the three fluid nozzle. Some active agents can interact with the lipids (e.g. peptides or proteins, have seen this already, especially the charged lipids like PG, e.g. DPPG). For this and other reasons e.g. biocompatibility, storage stability, vibration stability or release rate modification, it may be desirable to have the outside layer of phospholipids composition different from the inside chamber wall composition (e.g. PG only on the outside where it gives charge stability to the MVL but not present during high shear mixing with the active agent first aqueous). In some embodiments, the outside layer of phospholipid is put on the particle when the first component contacts the second aqueous phase, inside the nozzle and is subsequently atomized and it comes from the phospholipids left dissolved in the solvent after the first emulsion is made. Phospholipids with the desired outside composition, dissolved in solvent, can be injected into the first fluid conduit, just before the 3 fluid nozzle, and just before an optional static or other mixer so that these lipids are present and dissolved in the solvent phase of the first component. These phospholipids would only contact active containing first component droplets for seconds under mild shear condition and would thus not interact appreciably with the outer layer lipids. Some of these added lipids may get incorporated between the chambers of the forming MVL which the 4 fluid nozzle avoids.

In some embodiments, the one or more second amphipathic lipids in the second organic phase can be selected from the group consisting of soya lecithin, 1,2-dioleoyl-sn-glycero-3-phosphocholine, 1,2-dilauroyl-sn-glycero-3-phosphocholine, 1,2-dimyristoyl-sn-glycero-3-phosphocholine, 1,2-dipalmitoyl-sn-glycero-3-phosphocholine, 1,2-distearoyl-sn-glycero-3-phosphocholine, 1,2-diarachidoyl-sn-glycero-3~phosphocholine, 1,2-dibehenoyl-sn-glycero-3-phosphocholine, 1,2-dipalmitoleoyl-sn-glycero-3-phosphocholine, 1,2-dieicosenoyl-sn-glycero-3-phosphocholine, 1,2-dierucoyl-sn-glycero-3-phosphocholine, 1,2-dipalmitoyl-sn-glycero-3-phosphoglycerol, 1,2-dioleoyl-sn-glycero-3-phosphoglycerol, and mixture thereof. In a typical embodiment, the amphipathic lipid can be selected from the group consisting of 1,2-dierucoyl-sn-glycero-3-phosphocholine (DEPC), 1,2-dipalmitoyl-sn-glycero-3-phosphoglycerol (DPPG) and mixtures thereof.

Solvent Removal

In some embodiments, the organic solvent, such as methylene chloride, can be nearly or completely removed from a droplet by further contacting the droplet with a gas (or a gas with some degree of aqueous phase vapor), such as nitrogen gas, or air scrubbed of CO2, or air substantially free of CO2 in a solvent removal chamber. As described below, in some embodiments, the gas can have 50% to 100% relative humidity. For example, the humidity can be 100%. In some embodiments, the droplet can remain suspended in the gas within the solvent removal chamber until nearly all of the organic solvent is removed thereby creating a large diameter synthetic membrane vesicle particle. In some embodiments, the solvent removal can be done in a solvent removal chamber as discussed herein. The large diameter synthetic membrane vesicle particle can then be collected along with multiple other large diameter synthetic membrane vesicle particles, forming large diameter synthetic membrane vesicles suspended in a continuous aqueous phase. In some embodiments, the large diameter synthetic membrane vesicles suspended in a continuous aqueous phase can undergo further processing. In some embodiments, the large diameter synthetic membrane vesicles can be multivesicular liposomes.

Particle Concentration

Optionally, the large diameter synthetic membrane vesicles suspended in the continuous aqueous solution can be processed to modify/exchange the continuous aqueous solution via a particle concentration system. In this document the term concentration unit, concentration apparatus, concentration system, particle-concentration system, particle-concentrating device, and particle concentrator are meant to encompass units and processes that remove some of the particle suspending medium of a particle suspension and therefore concentrating the particle concentration as well as encompassing the exchange of the suspending medium with a new suspending medium, performed in one step or incrementally. These two processes are closely related as exchanging the suspending medium can be accomplished by concentrating the suspension and adding new suspending medium. These terms relate to concentrating the particle suspension and exchanging the suspending medium to be done separately or simultaneously. In some embodiments, the large diameter synthetic membrane vesicles can be multivesicular liposomes.

In one embodiment, the continuous aqueous solution can be modified/exchanged by diafiltration or cross-flow filtration. The diafiltration can achieve several objectives, including: exchanging an aqueous solution by an isotonic solution, concentrating of the large diameter synthetic membrane vesicles particles, removing unencapsulated drug, and removing of residual organic solvent. In some embodiments, the large diameter synthetic membrane vesicles can be multivesicular liposomes.

Particle concentration, such as through diafiltration, can be a method employed for the filtration, purification, and separation of the large diameter synthetic membrane vesicles particles from complex mixtures by virtue of the physical characteristics of the large diameter synthetic membrane vesicles particles. For example, the most common physical characteristic used is size. This filtration can involve cross-flow filtration, as opposed to dead-end filtration. In cross-flow filtration, a suspension can be circulated under pressure and in contact with a filter, so that a permeate (the material which passes through the filter) leaves the system, and a retentate (the material which does not pass through the filter) is left behind and exits the filter housing through a port different than the permeate and can be recirculated through the filter. The suspension then becomes concentrated in material that does not pass through the filter. In processes in which a first solution is to be exchanged for a second solution, the second solution is introduced on the retentate side of the filter, until the permeate gradually consists of the second solution. By this time, the first solution has been flushed from the suspension. An additional consequence of suspending medium exchange is to further remove any residual organic solvent, such as methylene chloride which has a small but appreciable water solubility and is thus removed in the permeate stream. Likewise the therapeutic agent released during the large diameter synthetic membrane vesicles formation can also be removed in the permeate. In some embodiments, the large diameter synthetic membrane vesicles can be multivesicular liposomes.

In some embodiments, aseptic methods can be included with any of the described methods and apparatus described herein.

Although sterilization of a final filled container as a dosage form is often a preferred process in pharmaceutical manufacture for the assurance of minimal risk of microbial contamination in a lot, the large diameter synthetic membrane vesicles manufactured in the present processes can be susceptible to unacceptable damage when subjected to some terminal sterilization techniques, such as autoclaving and gamma irradiation. In the absence of validated, non-damaging terminal sterilization, some embodiments of the invention utilize aseptic techniques, in which the product is prepared according to a carefully designed series of aseptic steps. These are designed to prevent the introduction of viable microorganisms into components, where sterile, or once an intermediate process has rendered the bulk product or its components free from viable microorganisms. Products defined as aseptically processed can consist of components that have been sterilized by aseptic means. For example, bulk products which are filterable liquids, can be sterilized by filtration. Final empty container components can be sterilized by heat; dry heat for glass vials and autoclaving for rubber seal components. The requirements for properly designed, validated and maintained filling and processing facilities are directed to: an air environment free from viable microorganisms, and designed to permit effective maintenance of air supply units; training of personnel who are adequately equipped and gowned. Available published standards for controlled work areas include: Federal Standard No. 209B, Clean Room and Work Station Requirements for a Controlled Environment, Apr. 24, 1973; NASA Standard for Clean Room and Work Stations for Microbially Controlled Environment, publication NHB5340.2, August 1967; and Contamination Control of Aerospace Facilities, U.S. Air Force, T. O. 00-25-203, Dec. 1, 1972, change 1, Oct. 1, 1974. In some embodiments, the large diameter synthetic membrane vesicles can be multivesicular liposomes.

In aseptic processing, one of the most important laboratory controls is the establishment of an environmental monitoring program. Samples can be collected from areas in which components and product are exposed to the environment, including mixing rooms and component preparation areas. Microbiological quality of aseptic processing areas is monitored to determine whether or not aseptic conditions are maintained during filling and closing activities. Routine sampling and testing of the room air, floors, walls, and equipment surfaces is carried out. This program establishes the effectiveness of cleaning and sanitizing equipment and product contact surfaces, and ensures that potential contaminants are held to an acceptable level. The disinfectants are checked to assure that their efficacy against normal microbial flora is maintained. Sampling schedules, including locations and frequency of sampling, are maintained. Passive air samplers such as settling plates (Petri dishes) are employed as well.

Aseptic assembly operations can be validated by the use of a microbiological growth nutrient medium to simulate sterile product filling operations, known as "sterile media fills." The nutrient medium can be manipulated and exposed to the operators, equipment, surfaces and environmental conditions to closely simulate the same exposure which the product itself will undergo. The sealed drug product containers filled with the media can then be incubated to detect microbiological growth and the results are assessed to determine the probability that any given unit of drug product may become contaminated during actual filling and closing operations. Media filling, in conjunction with comprehensive environmental monitoring can be particularly valuable in validating the aseptic processing of sterile solutions, suspensions, and powders. Filling liquid media, as part of validating the processing of powders, may necessitate use of equipment and/or processing steps that would otherwise not be attendant to routine powder operations.

In some embodiments, clean-in-place (CIP) and sterilize-in-place (SIP) procedures can be utilized by methods generally known in the art. Some embodiments include monitoring of the temperature at the steam traps. According to this procedure, as steam is admitted into the vessels and fill lines to effect sterilization, the temperature at the outlet points is monitored until bacterial kill is assured. At this point, the seals can be closed, and the system can be sterilized for further use. Subsequently, the equipment can be used aseptically in a non-sterile room environment. The systems described herein, may also comprise additional components (e.g. valves, steam lines, condensate drains) to facilitate sterilization by steaming-in-place.

Sterility testing of product lots can be carried out directly after the lot is manufactured as a final product quality control test. Testing can be done in accordance with various procedures found in the U.S. Pharmacopeia (U.S. P.) and FDA regulations.

Sterile filtration of all fluids which enter the manufacturing system is essential for an aseptic process, as envisioned in certain embodiments of the present application. Rating of pore sizes of filter membranes is by a nominal rating reflecting the capacity of the membrane to retain microorganisms of size represented by specified trains, not by determination of an average pore size and statement of distribution of sizes. Sterilizing filter membranes include those capable of retaining 100% of a culture of $10^7$ organisms of a strain of *Pseudomonas diminua* (ATTC 19146) per square cm of membrane surface under a pressure of not less than 30 psi. Such filter membranes can be nominally rated 0.22 μm or 0.2 μm, depending on the manufacturer. Bacterial filter membranes capable of retaining only larger microorganisms (including *Serratia Marcescens* (ATTC 14756)) are labeled with a nominal rating of 0.45 μm. Filter membranes used in the present processes can be of the 0.2 μm type, and can be used in all lines feeding from liquid solution and gas storage tanks to vessels and transfer lines used in the methods disclosed herein.

In some embodiments the process apparatus is sterilized before use and isolated from the environment by the use of sterilizing filters on all apparatus inputs and outputs where the apparatus includes the sterilized product vessel. In this embodiment sterile product can be produced in an aseptic fashion, in a non sterile environment.

Description of the Instant Devices and their Methods of Use

The present embodiments will now be described in more detail in terms of features and operations with reference to the accompanying drawings.

FIG. 1A

An embodiment of the present application is a continuous-flow system for manufacturing pharmaceutical formulations. An example of such a continuous-flow system is presented in FIG. 1A. FIG. 1A is a schematic diagram of the significant components and sub-systems used in a system for manufacturing pharmaceutical formulations. Each of the components and sub-systems can be included in, and operated as, a part of the larger manufacturing system or may, in the alternative, be run autonomously in a continuous fashion to accomplish the objective of each sub-system as described herein. Additionally, each sub-system may be run in a continuous-flow manner using batch inputs and producing a batch output.

In one embodiment, the manufacturing system 100 is comprised of a tank 5, which can hold a first fluid, the first fluid can be pumped by a positive-displacement pump 2 through a hydrophilic sterilizing filter 15 and into a high shear mixer 25. In some embodiments, the first fluid can be an aqueous solution. In some embodiments, the first fluid can be a first liquid. In some embodiments, the first liquid can be an aqueous solution. Similarly, tank 10 can feed a second fluid, via a positive-displacement pump 12, through a hydrophobic sterilizing filter 20 into the high shear mixer 25. In some embodiments, the second fluid can be a second liquid. In some embodiments, the second liquid can be an organic solvent. The high shear mixer 25, a heat exchanger 30, and associated inlet line 96 and outlet line 97 comprise one embodiment of a first sub-system. In some embodiments, the first sub-system can be a first emulsification sub-system. In some embodiments, the high shear mixer 25 can create a first dispersion of aqueous particles (the "discontinuous phase") suspended in an organic continuous phase. In some embodiments, the first dispersion can be a first component. In some embodiments, a majority of the first component can then be fed from the high shear mixer 25 into the heat exchanger 30, and the cooled first component can flow back to the high shear mixer 25. In one embodiment, however, a portion of the emulsion leaving the high shear mixer 25 can be forced towards a nozzle 75, for example by the addition of additional organic solvent and aqueous solution to the first emulsification sub-system.

In some embodiments, the emulsion leaving the high shear mixer 25 can be transferred to an evaporation apparatus or evaporation sub-system. In one embodiment the evaporation apparatus, or evaporation sub-system, is comprised of a solvent removal vessel 50, the atomizing nozzle 75, a gas inlet 115, and a gas outlet 80. In some embodiments, the nozzle 75 acts to spray atomized droplets of the first component into the solvent removal vessel 50. In some embodiments, the nozzle 75 can combine the first component with a fluid from a tank 60 and spray the first component/liquid mixture into the solvent removal vessel 50 as atomized droplets. In some embodiments, the fluid from the tank 60 is a liquid. In some embodiments, the liquid from the tank 60 is a buffer solution. In some embodiments, the buffer solution can be fed by a positive-displacement pump 22 from the tank 60 through a hydrophilic sterile filter 65 into the nozzle 75. Gas from the gas supply can be passed through a pressure regulator 11 and a sterilizing gas filtration system 35 before entering the nozzle 75. In some embodiments, the gas acts to atomize the first component/liquid mixture as it exits the nozzle 75 into the solvent removal vessel 50.

In some embodiments, a carrier gas can be supplied to the solvent removal vessel 50 from the gas supply and enter the solvent removal vessel through the gas inlet 115. The carrier gas can be, for example, nitrogen gas (or a nitrogen gas/aqueous vapor mixture) or air scrubbed of $CO_2$. The pressure of the carrier gas can be regulated using a pressure regulator 31. In some embodiments, the carrier gas first passes through a heater/humidifier 90 and then through a gas filtration system 45 before entering the solvent removal vessel 50 through the gas inlet 115. In some embodiments, the carrier gas circulates through the solvent removal vessel 50, and creates an intense gas vortex, which can facilitate solvent evaporation from the atomized droplets as they are sprayed into the solvent removal vessel 50 from the nozzle 75. The gas vortex can substantially prevent the atomized droplets from exiting the solvent removal chamber with the carrier gas through gas outlet 80. With evaporation of the solvent, the atomized droplets become droplets of large diameter synthetic membrane vesicles within an aqueous phase. In some embodiments, the atomized droplets can be first component/liquid mixture droplets. In some embodiments, the large diameter synthetic membrane vesicles can be within an aqueous phase. In some embodiments, the large diameter synthetic membrane vesicles can be multivesicular liposomes. In some embodiments, the carrier gas and evaporated solvent can then be removed from the solvent removal vessel 50 through the gas outlet 80, after which they can then pass through a filtration system 55 comprised of a pre-filter and a sterilizing barrier filter, before being removed as waste 95. In some embodiments, the prefilter (not shown) can be a high efficiency cyclone separator.

In one embodiment, the evaporation sub-system is comprised of a plurality of solvent removal vessels, each with one or more atomizing nozzles, used in parallel to evaporate the solvent from the atomized droplets. In some embodiments, the evaporation sub-system can be comprised of a plurality of solvent removal vessels, such as solvent removal vessel 50, each with one or more atomizing nozzles, such as atomizing nozzle 75, used in parallel to evaporate solvent from the atomized droplets. In some embodiments, the solvent removal vessel can have additional multiple atomizing nozzles (not shown) such as 75.

In some embodiments, a portion of the gas passing through the heater/humidifier 90 can be directed towards a gas inlet 110 located in the lid of the solvent removal vessel 50. In some embodiments, the gas inlet 110 allows gas to enter the solvent removal vessel 50 and circulate in the upper portion of the vessel acting to prevent particle buildup on the lid.

In some embodiments, a two-fluid rinse nozzle 105 can be placed in and through the lid of the solvent removal vessel 50. In some embodiments, the rinse nozzle 105 can spray the wall of solvent removal vessel 50. The rinse nozzle 105, which receives a buffer solution from a buffer solution tank 66, through a pump 64 and a sterilizing filter 62, can spray atomized tank wall rinse solution particles into the solvent removal vessel 50. The buffer solution can be atomized by gas traveling into the nozzle 105 through a pressure regulator 21 and a sterilizing gas filtration system 85. Spraying atomized wall rinse solution particles into the solvent removal vessel 50 can act to prevent the large diameter synthetic membrane vesicles droplets (FIG. 7, component 7380) from sticking to the walls of the solvent removal vessel 50 by rinsing or flushing particles from the internal surfaces of the vessel 50, and out a drain port 130 on the bottom of the vessel 50.

Removal of the solvent from the atomized droplets, affords large diameter synthetic membrane vesicles coated in a buffer solution shell as droplets. In some embodiments, the large diameter synthetic membrane vesicles can be multivesicular liposomes. These droplets then can collect on the bottom of the solvent removal vessel 50 to form a suspension of large diameter synthetic membrane vesicles in a buffer solution. This large diameter synthetic membrane vesicles suspension can subsequently be pumped by a pump 125 through a solvent removal vessel outlet line 120 to an optional sub-system 70. In some embodiments, the large diameter synthetic membrane vesicles suspension can be pumped by a pump 125 through a continuous heat treatment system 150 before entering the option sub-system 70. In some embodiments, the buffer solution can be exchanged for, for example, a saline solution. In some embodiments, the sub-system 70 can be a single or series of concentration units running in batch or continuous mode. In a typical embodiment, the concentration units can be run in continuous mode. In a typical embodiment, large diameter synthetic membrane vesicles can be concentrated and the resulting suspension collected by the process. In some embodiments, the large diameter synthetic membrane vesicles can be multivesicular liposomes.

In some embodiments, one or more components of the manufacturing system 100 can be omitted from the system. FIG. 1B In some embodiments, the manufacturing system 100 further comprises a mass flow controller 13, a mass flow controller 23, a mass flow controller 33, a rotometer flow indicator 57, a heater 93, a steam generator 40, and a metering pump 6 as shown in FIG. 1B. Each of the components and sub-systems can be included in, and operated as, a part of the larger manufacturing system or may, in the alternative, be run autonomously in a continuous fashion to accomplish the objective of each sub-system as described herein. Additionally, each sub-system may be run in a continuous-flow manner using batch inputs and producing a batch output.

In some embodiments, the mass flow controllers 13, 23, and 33 measure, indicate, and control the gas flow supply to their associated apparatus. In some embodiments, the rotometer flow indicator 57 measures and indicates the gas flow to the lid protection nozzle (FIG. 1A 110 7430. In some embodiments, the steam generator 40 allows precise humidification of the carrier gas. In some embodiments, the metering pump 6 allows precise control of the water vapor generated by the steam generator 40.

FIG. 1C

One embodiment of the present application includes a continuous heat treatment system. FIG. 1C provides a schematic of one example of a continuous heat treatment system 150. In some embodiments, the large diameter synthetic membrane vesicles suspension can be pumped from the solvent removal vessel (FIG. 1A, component 50) flowing through a feed line 120 (also seen in FIG. 1A, component 120), to the continuous heat treatment system 150 before entering a subsystem (FIG. 1A, component 70).

In some embodiments, the continuous heat treatment system comprises a temperature controlled tank 151, optionally a temperature control jacket (not shown), a pressurized tank 160, a holding coil tubing 156, and a nitrogen source 157 as shown in FIG. 1C. Each of the components and sub-systems can be included in, and operated as, a part of the larger manufacturing system or may, in the alternative, be run autonomously in a continuous fashion to accomplish the objective of each sub-system as described herein. Additionally, each sub-system may be run in a continuous-flow manner using batch inputs and producing a batch output.

In some embodiments, a portion of the large diameter synthetic membrane vesicles suspension can be pumped by a pump (FIG. 1A, component 125) through the feed line 120 into a mixing vessel 180, for example an in-line static mixer. In some embodiments, the large diameter synthetic membrane vesicles suspension, flowing through the line 120, can come into contact with a solution from the tank 151 before flowing through a line 155 into the mixing vessel 180. In one embodiment, the suspension feeding the mixing vessel 180 through the line 120, flows at 165 ml/min and the solution through the line 155 flows at 247.5 ml/min, In some embodiments, the solution can be fed through a line 152 by a pump 153, the solution first passing through a hydrophilic sterile filter 154 at a rate of 1.5 L per 1 L of the large diameter synthetic membrane vesicles suspension added to the mixing vessel 180. In some embodiments, the tank 151 is temperature controlled. In some embodiments, the solution from the tank 151 is a dextrose solution. In some embodiments, the dextrose solution is heated to about 98° C. in the temperature controlled tank 151. In some embodiments, the suspension/dextrose mixture flows through the holding coil tubing 156. In some embodiments, the holding coil tubing 156 holds the suspension/dextrose mixture for a specified treatment time. In some embodiments, the treatment time is between 10 seconds and 30 seconds. In some embodiments, the suspension/dextrose mixture is continuously heated for 30 seconds to a temperature at or above 60 C. In some embodiments, the holding coil tubing 156 has a volume of 206 ml.

In some embodiments, the suspension/dextrose mixture can leave the holding coil tubing 156 to enter a retentate vessel 168. In some embodiments, a solution can be fed from the tank 160 into the retentate vessel 168 through a line 164, the solution first passing through a manual valve 162 and a sterilizing hydrophilic filter 163, at a rate of 1.4 L per 1 L suspension/dextrose mixture added to the retentate vessel 168. In some embodiments, the solution flows through the line 164 at a rate of 578 ml/min. In some embodiments, the tank 160 is temperature controlled. In some embodiments, the temperature controlled tank is pressurized. In some embodiments, the tank 160 is pressurized with the nitrogen source 157 through a line 158 and a manual valve 159. In some embodiments, the solution is a saline solution. In some embodiments, the saline solution is a cold saline solution. In some embodiments, the retentate vessel 168 is temperature controlled or cooled.

In some embodiments, a portion of the suspension/dextrose mixture in the retentate vessel 168 can be pumped by a pump 171 through a cross-flow (tangential-flow) filtration module 167. In some embodiments, the permeate can be drawn off through a permeate line 173 (passing through a sterilizing hydrophilic filter 172 and a manual valve 174), wherein for each volume of suspension/dextrose mixture added to the retentate vessel 168, a volume can be removed and discarded. In some embodiments, the retentate from the filtration module 167 can be circulated back into the retentate vessel 168 via a retentate line 166. In some embodiments, for each volume of suspension/dextrose mixture added to the retentate vessel 168, a volume of the liquid can be removed from the retentate vessel 168 through a feed line 169 and a metering pump 170 to be further processed by a subsystem (as seen in FIG. 1A, component 70; systems of FIG. 8, FIG. 10 and FIG. 11). In some embodiments, the suspension can flow through the pump 170 at a rate of 490 ml/min.

Filters 154, 163, and 172 are sterilizing hydrophilic filters. Filters, 161 and 176 are sterilizing hydrophobic gas vent filters used in the vessels and fed by gas lines 165 and 175, respectively.

FIG. 2

Figure 2:
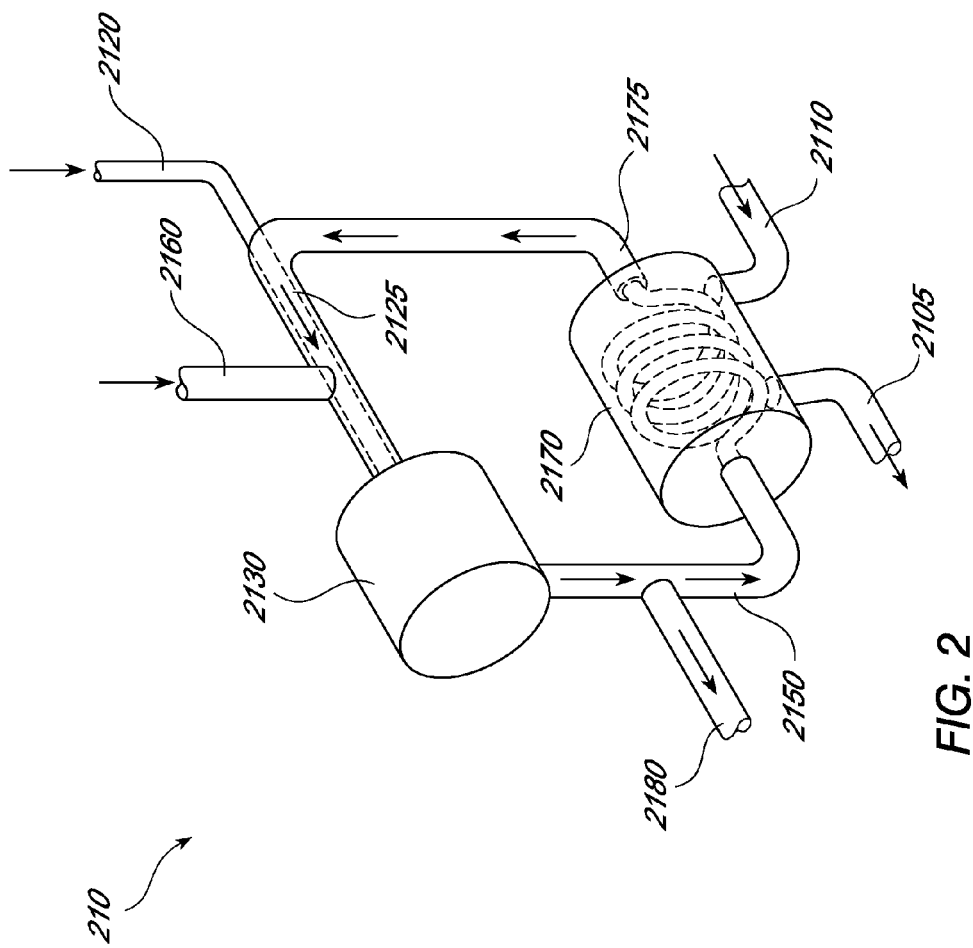
FIG. 2 is a schematic of one embodiment of an emulsification system used in the manufacturing system of FIG. 1A or FIG. 1B.

One embodiment of the present application includes an emulsification system, the process of using the system, and the large diameter synthetic membrane vesicles products made by the process. In some embodiments, the large diameter synthetic membrane vesicles can be multivesicular liposomes. FIG. 2 provides a schematic of one example of a continuous-flow emulsification system 210. The emulsification system 210 includes a high shear mixer 2130 and a heat exchanger 2170. In some embodiments, the high shear mixer 2130 can be used in preparing a first component. The high shear mixer 2130 used in one embodiment is the Ross HSM-703XS-20 Sanitary Inline High Shear Mixer made by the Charles Ross & Son Company of Hauppauge, N.Y. In some embodiments, the head of the high shear mixer 2130 can be connected to an aqueous inlet line 2120. In some embodiments, the head of the high shear mixer 2130 can be fed an aqueous solution through the aqueous inlet line 2120. In some embodiments, the head of the high shear mixer 2130 can be connected to a recirculation line 2125. In some embodiments, the high shear mixer 2130 can feed a recirculated emulsion through the recirculation line 2125. The recirculated emulsion contains already-sheared aqueous droplets dispersed in a continuous organic solution. In some embodiments, the aqueous solution can be stored in a tank (FIG. 1A, component 10) and pass through a liquid sterilization filter (FIG. 1A, component 20) attached to the aqueous inlet line 2120 before entering the high shear mixer 2130 at various volumetric flow rates. High shear mixers are available to deliver volumetric flow rates between 1 mL/minute and 4,000 mL/minute, between 10 mL/minute and 1,000 mL/minute, between 10 mL/minute and 100 mL/minute, and preferably between 15 mL/minute and 50 mL/minute. In some embodiments, the aqueous inlet line 2120 can be configured to run co-axially through a portion of the recirculation line 2125. The range of volumetric flow rates above is appropriate when contemplating the use of one, or optionally multiple, atomizing nozzles.

In some embodiments, the aqueous solution can be injected through the center of a stator inside of the head of the high shear mixer 2130 into the center of a spinning rotor (not shown) also inside the high shear mixer head 2130. As the aqueous phase passes between the rotor and the stator, inside the high shear mixer head 2130, it is sheared by the rotor teeth and stator teeth into aqueous droplets. The sheared aqueous droplets become part of a flowing stream of the recirculated emulsion which itself can be fed back into the high shear mixer through the recirculation line 2125. The combined aqueous solution and recirculated emulsion can pass through blade shear gaps (not shown) in the high shear mixer head 2130, as it travels from the center to the outside of the rotor. In one embodiment, on average, aqueous droplets are recirculated approximately 100 times through the emulsification system 210, and through that process, the aqueous droplets are sheared roughly 1,300 times by the blade shear gaps (not shown).

Exiting the high shear mixer head 2130 through an exit line 2150 is the resultant emulsion, with aqueous droplets dispersed in the organic continuous phase, traveling at a volumetric flow rate between 1 L/minute and 500 L/minute, between 5 L/minute and 100 L/minute, and preferably between 10 L/minute and 50 L/minute. The major portion of the emulsion exiting the high shear mixer 2130, approximately between 50% and 99.99%, between 70% and 99.9%, and preferably between 80% and 99.9%, is passed through the heat exchanger 2170 to cool the emulsion which has been heated by the mechanical shearing process of the high shear mixer 2130. Additionally, a smaller portion of the recirculating emulsion, approximately between 1 mL/minute and 8,000 mL/minute, between 10 mL/minute and 2,000 mL/minute, between 20 mL/minute and 200 mL/minute, and preferably between 40 mL/minute and 100 mL/minute, travels from the high shear mixer 2130 through a nozzle feed line 2180 to a nozzle for use in making the first component/buffer atomized droplets. The range of volumetric flow rates above is appropriate when contemplating the use of one, or optionally multiple, atomizing nozzles. In some embodiments, the heat exchanger 2170 can be comprised of a series of coils surrounded by circulating solution. In some embodiments, the circulating solution can be at a temperature ranging from about −5° C. to about 30° C. In some embodiments, the circulating solution can be a glycol/water solution. In some embodiments, the glycol/water solution can be at a temperature ranging from about 0° C. to about 10° C. In some embodiments, the heat exchanger 2170 is comprised of a series of coils surrounded by circulating 5° C. glycol/water solution. In some embodiments, the circulating glycol/water solution can be fed to the heat exchanger 2170 through an inlet line 2110 and an outlet line 2105. In some embodiments, the emulsion travels through the heat exchanger coils, being cooled by the glycol/water solution, and exits the heat exchanger through a heat exchanger outlet 2175. In some embodiments, the heat exchanger outlet 2175 can carry the cooled emulsion back through the recirculation line 2125 for additional mixing with added aqueous phase and added organic solution. In some embodiments, the high shear mixer 2130 can act as a high volume centrifugal pump to drive a high volumetric flow rate through the heat exchanger and around the recirculation loop, back to the high shear mixer head 2130.

Attached to the recirculation line 2125 is an organic solution inlet line 2160, which can be used to replenish the organic solution in the emulsification system 210 according to the volumetric amount of organic solution fed in the first component to the nozzle feed line 2180. In some embodiments, the organic solution can be stored in a tank (not shown) and flows, at a volumetric flow rate between 1 mL/minute and 4,000 mL/minute, between 10 mL/minute and 1,000 mL/minute, between 10 mL/minute and 100 mL/minute, and preferably between 20 mL/minute and 50 mL/minute. The range of volumetric flow rates above is appropriate when contemplating the use of one, or optionally multiple, atomizing nozzles. In some embodiments, the organic solution flows through a liquid sterilization filter (shown in FIG. 1A and FIG. 1B, component 15) attached to the organic inlet line 2160 before entering the recirculation line 2125 and the high shear mixer 2130. In one embodiment, the volumetric flow rate of the organic solution added through the inlet line 2160 can be equal to the volumetric flow rate of aqueous solution added to the high shear mixer 2130 through the aqueous inlet line 2120. That is, in one embodiment, the volumetric flow rates of the added liquids are at a 1:1 ratio. At steady-state, because these are incompressible fluids and the piping described herein is non-expandable piping, the flow rate of the first component traveling to the nozzle through the nozzle feed line 2180 is equal to the sum of the flow rates of the organic solution being replenished to the emulsification system 210 through the organic phase inlet line 2160 and the aqueous solution being replenished to the emulsification system 210 through the aqueous inlet line 2120.

In one embodiment, the emulsification system is used autonomously to make MVL where the first component is collected in a container and further processed to make the second emulsion. The second emulsion is then sparged and filtered in a batch mode as described in PCT Patent Publication No. WO99/13865 to S. Kim et al., incorporated herein by reference.

In one embodiment, the emulsification system is employed autonomously to produce common emulsions of triglycerides (vegetable oils) and surfactants (Tween-20, Pluronic F-66, egg lecithin) and water with common additives (scents, flavors). In an additional embodiment, a cosmetic lotion is made with a triglyceride as the discontinuous phase (oil in water emulsion). In still other embodiments, the emulsification system produces ointments, creams and salves, with the triglyceride as the continuous phase. Additionally, a triglyceride emulsion in water with egg yolk as the surfactant is used in the emulsification system to produce a type of edible mayonnaise.

FIG. 3A-6

One embodiment of the present application includes an atomizing nozzle, the process of using the nozzle, and the large diameter synthetic membrane vesicles made by the process. In some embodiments, the large diameter synthetic membrane vesicles can be multivesicular liposomes. Examples of the instant atomizing nozzles, the processes for using them, as well as the MVL products, are presented in FIG. 3A-6 and described herein.

FIG. 3A

FIG. 3A is a schematic partial view of an atomizing nozzle 310, providing a cross-sectional view of the lower portion of the atomizing nozzle including a fluid contacting chamber 3125. The fluid contacting chamber 3125 is conically tapered from the bottom of an inner fluid conduit 3165 to a cylindrical tip 3145. The fluid contacting chamber 3125 is annularly surrounded by an annular gas chamber (a third fluid conduit) 3135, which narrows to form an annular gas orifice 3150. The bottom portion of the cylindrical tip 3145 is annularly and concentrically surrounded by the annular gas orifice 3150.

In some embodiments, a first fluid 3115 can travel at a volumetric flow rate between 2 mL/minute and 1,000 mL/minute, between 10 mL/minute and 500 mL/minute, between 20 mL/minute and 100 mL/minute, and preferably between 50 mL/minute and 100 mL/minute through an inner fluid conduit (central needle) 3165. In a typical embodiment, the first fluid 3115 is an emulsion. In some embodiments, the first fluid exits the bottom 3163 of the inner fluid conduit 3165 and enters the fluid contacting chamber 3125, whereupon the first fluid 3115 comes in physical communication with a second fluid 3120. In a typical embodiment, the second fluid 3120 is a buffer solution. In some embodiments, the second fluid 3120 travels at a volumetric flow rate between 2 mL/minute and 1,000 mL/minute, between 10 mL/minute and 500 mL/minute, between 20 mL/minute and 100 mL/minute, and preferably between 50 mL/minute and 100 mL/minute, through the outer fluid conduit 3123, which annularly surrounds the inner fluid conduit 3165 (as seen from the downward perspective view B and displayed in FIG. 3B), to reach the fluid contacting chamber 3125. The above atomizing nozzle flow rates are for a single atomizing nozzle. In some embodiments, the first fluid 3115 forms a cylindrical core traveling through the fluid contacting chamber 3125, now being in physical communication with, and annularly surrounded by, the second fluid 3120. In some embodiments, the first fluid and the second fluid are immiscible. In some embodiments, the first fluid and second fluid can be sparingly miscible. In some embodiments, the immiscibility between the second fluid 3120 and the first fluid 3115, and the velocity at which the second fluid 3120 and the first fluid 3115, causes the second fluid 3120 to form a sheath around the first fluid 3115 core. In a typical embodiment, the first fluid 3115 is an emulsion and the second fluid 3120 is a buffer solution.

In some embodiments, the diameter of the fluid contacting chamber 3125 can be conically narrowed as it joins the cylindrical tip 3145. As the first fluid 3115 travels through the narrowing fluid contacting chamber 3125 and into the cylindrical tip 3145, the diameter of the first fluid 3115 core is correspondingly decreased. Likewise, the second fluid 3120 can be constricted to create a thinner concentric annular sheath around the first fluid 3115 core. As a result of decreasing the diameter of the fluid contacting chamber 3125 and passing the fluids through the cylindrical tip 3145, the velocities of the first fluid 3115 and second fluid 3120 are increased. In a typical embodiment, the first fluid 3115 is an emulsion and the second fluid 3120 is a buffer solution.

FIG. 3C shows an expanded cross-sectional view of the first fluid and second fluid in the cylindrical tip 3145. In some embodiments, the ratio of the diameters of the first fluid to the second fluid in the nozzle tip can be the same as the ratio of the diameters of the first fluid in inner fluid conduit 3165 to the second fluid in the outer fluid conduit 3123. In some embodiments, the ratio of the diameters of the first fluid to the second fluid in the nozzle tip can be larger than the ratio of the diameters of the first fluid in the inner fluid conduit 3165 to the second fluid in the outer fluid conduit 3123. In some embodiments, the ratio of the diameters of the first fluid to the second fluid in the nozzle tip can be smaller than the ratio of the diameters of the first fluid in inner fluid conduit 3165 to the second fluid in the outer fluid conduit 3123.

FIG. 3D shows an expanded cross-sectional view of the first fluid and second fluid in a droplet 3155. In some embodiments, the ratio of the diameters of the first fluid to the second fluid in a droplet 3155 can be the same as the ratio of the diameters of the first fluid in the inner fluid conduit 3165 to the second fluid in the outer fluid conduit 3123. In some embodiments, the ratio of the diameters of the first fluid to the second fluid in a droplet 3155 can be larger than the ratio of the diameters of the first fluid in the inner fluid conduit 3165 to the second fluid in the outer fluid conduit 3123. In some embodiments, the ratio of the diameters of the first fluid to the second fluid in a droplet 3155 can be smaller than the ratio of the diameters of the first fluid in the inner fluid conduit 3165 to the second fluid in the outer fluid conduit 3123.

The nozzle 310 comprises a gas input channel 3130 which supplies a gas 3140. In some embodiments, the volumetric flow rate of the gas can be between 30 L/minute and 1,000 L/minute, between 30 L/minute and 500 L/minute, between 20 L/minute and 200 L/minute, and preferably between 25 L/minute and 100 L/minute and at a pressure between 5 psig and 1,000 psig, between 10 psig and 250 psig, between 20 psig and 150 psig, and preferably between 40 psig and 120 psig to an annular gas chamber 3135. The above atomizing nozzle flow rates are for a single atomizing nozzle. Prior to reaching nozzle 310, the gas 3140 can be passed through a gas filtration system (not shown) comprising a hydrophobic gas sterilizer (as seen in FIG. 1A and FIG. 1b, component 35). The wall of the fluid contacting chamber 3125 provides a barrier between the annular gas chamber 3135 and the fluid contacting chamber 3125 such that there is no physical contact between the fluids in the fluid contacting chamber 3125 and the gas 3140 in the annular gas chamber 3135. In some embodiments, the outlet of the cylindrical tip 3145 and the outlet of the annular gas orifice 3150 can be flush with each other such that second fluid 3120 does not come into contact with the gas 3140 prior to the gas 3140 exiting the atomizing nozzle 310. In other embodiments, the cylindrical tip 3145 extends lower than the annular gas orifice 3150. In still other embodiments, the cylindrical tip 3145 is slightly recessed within the annular gas orifice 3150, such that the gas 3140 comes into physical communication with the second fluid 3120 prior to the second fluid fully exiting from the nozzle 310.

In some embodiments, as the gas 3140 passes through the annular gas orifice 3150 and exits the atomizing nozzle 310, it comes in physical communication with the second fluid 3120 and acts to shear the stream of the second fluid 3120 and the first fluid 3115 into multiple atomized droplets 3155 made of a first fluid 3115 core and a second fluid 3120 shell. This configuration of the three fluid nozzle can be best achieved when the cross sectional areas of the inner fluid conduit 3165 and the second fluid path within the fluid contacting chamber 3125 are chosen such that the velocities of the first fluid 3115 and the second fluid 3120 are approximately equal at the exit of the inner conduit 3163.

In some embodiments, the atomizing nozzle 310 can be configured to produce very high yield large diameter synthetic membrane vesicles (that is, vesicles that encapsulate a high amount of a therapeutic agent). In some embodiments, the large diameter synthetic membrane vesicles can be unilamilar vesicles or multilamilar vesicles or polymer spheres encasing a liquid comprising a therapeutic agent. In some embodiments, the large diameter synthetic membrane vesicles can be multivesicular liposomes. In some embodiments, the first fluid 3115 can be an aqueous (or similar hydrophilic liquid) phase containing the therapeutic agent and the second fluid 3120 can be an organic phase comprising phospholipids or other encasing material e.g. a polymer or PLGA (poly(lactic-co-glycolic acid), biocompatible and in-vivo degradable polymer) or a wax. In some embodiments, the gas 3140 combines with an aqueous phase and an organic phase to afford a droplet of aqueous phase inside a droplet of organic phase, which can, for example, be used to form unilamilar vesicles or multilamilar vesicles. In some embodiments, the size of the inner aqueous phase droplet can have an average diameter of at least about 0.5 µm, 1 µm, 5 µm, 10 µm, 15 µm, 20 µm, or 50 µm, or a diameter within a range defined by any of two of the preceding values. In some embodiments, the organic solvent can be removed by using a normal spray drying system. In some embodiments, the organic solvent can be removed by using solvent removal chamber such as the one described in FIG. 7.

In some embodiments, the nozzle 310 can comprise an additional outer fluid conduit (not shown), which annularly surrounds the inner conduit 3165 to provide a four fluid atomizing nozzle as shown in FIGS. 3E-3L. In some embodiments, the conduit which annularly surrounds the inner conduit 3165 can include an aqueous phase suitable as a suspending medium. In some embodiments, the nozzle can be operated to produce an emulsion where an aqueous drug core can be surrounded by phospholipids in a volatile solvent that in turn is surrounded by another aqueous phase, which can, for example, be used to form unilamilar vesicles or multilamilar vesicles. In some embodiments, the large diameter synthetic membrane vesicles will initially have a hydrophobic outer surface.

In some embodiments, the nozzle 310 can omit the conduit 3123 in order to provide a two fluid nozzle (not shown). In some embodiments, the two fluids are a liquid and a gas. In some embodiments, the two fluid nozzle (not shown) can be used to spray a first component into the instant solvent removal chamber such as the one described in FIG. 7. In some embodiments, the organic solvent can be removed by contacting the first component with an inert gas to in order to create the MVL. In some embodiments excess phospholipids can be used in the first component to create the MVL having a coating of phospholipids which initially has a hydrophic surface and can partially shed to afford the MVL with a hydrophilic surface.

FIG. 3E Through FIG. 3L

Liposomes with high incorporation percentages (especially important for an expensive active agents) can be made with a four fluid atomizing nozzle 320 as depicted in FIG. 3E through FIG. 3L. In some embodiments, a first fluid 3115 can be a fluid comprising an aqueous active agent, while a second fluid 3170 can be a volatile solvent comprising a lipid solution, wherein the second fluid 3170 forms a membrane while a third fluid 3120 can be a suspending buffer. Without the suspending buffer outer layer, the lipids would for with their hydrophobic regions facing out towards the hydrophobic gas. This four fluid nozzle assembles the outer membrane in a way to prevent aggregation. In such embodiments, the incorporation of the active agent is high because the active agent fluid can be surrounded by the lipid layer forming solvent 3170. Small concentrations of lipids in 3170 can provide at least one bilayer. In some embodiments, higher concentrations of lipid in the second fluid can provide liposomes comprising thick large numbers of bilayers. In some embodiments, structurally strong and stable liposomes can be made using tight packing saturated phospholipids with a high transition temperature as they are deposited from an evaporating solvent solution and do not have to be formed in aqueous solutions as per conventional liposome processes.

When the first core fluid 3115 is the first component lacking any lipids that could interact with the active agent (e.g. charged lipid like DPPG) and 3170 is volatile solvent (could be same or different that used in first component) and 3120 is a suspending buffer; MVLs with different lipids on the outside. These outside lipids (from 3170) can be highly charged for stability or long chain saturated for mechanical strength. The lipids can be put on the MVL as 1 or 2 bilayers or, if the lipid concentration in 3170 is high, be put on as a thick mechanically strong many multiple-bilayers (not previously done) to increase stability of the MVL and provide longer slower active agent release. If polymers (e.g. PLGA) were also added to 3120 (w/wo lipids), a polymer skeleton could be formed surrounding the MVL, further stabilizing it physically and chemically. If the polymer layer were strong enough. it would allow the MVLs to be lyophilized and be stable for very long times at room temperature.

FIG. 3E is a schematic partial cross-sectional view of a four fluid atomizing nozzle 320, comprising a first inner fluid conduit (central needle) 3165, a second inner fluid conduit 3175, an outer conduit 3123, a gas input channel 3130, an annular gas chamber (a fourth fluid conduit) 3135, a first fluid contacting chamber 3125, a second fluid contacting chamber 3137, and an annular gas orifice 3150. The first fluid contacting chamber 3137 is conically tapered from the bottom of the first inner fluid conduit 3165 and the exit orifice 3147 of the second inner fluid conduit 3175. The second fluid contacting chamber 3137 is conically tapered from the exit orifice 3147 of the second inner fluid conduit 3175 to a cylindrical tip 3145. In some embodiments, the exit orfice 3147 of the second inner fluid conduit 3175 can be between the exit orifice of the first inner fluid conduit 3163 and the cylindrical tip 3145.

In some embodiments, the second fluid contacting chamber, allows for the first and second fluids to contact the third fluid 3120 for a shorter duration than the nozzle described in FIG. 3I. In some embodiments, the four fluid atomizing nozzle 320 depicted in FIG. 3E can handle flow rates higher than the one fluid contacting chamber nozzle described in FIG. 3I through FIG. 3L due to lower flow instabilities. In some embodiments, the first and second fluid contacting chambers are hydraulic extrusion cones.

The second fluid contacting chamber 3137 is annularly surrounded by the annular gas chamber 3135, which narrows to form an annular gas orifice 3150. The exit orfice portion of the cylindrical tip 3145 is annularly and concentrically surrounded by the annular gas orifice 3150.

In some embodiments, a first fluid 3115 can travel at a volumetric flow rate between 2 mL/minute and 1,000 mL/minute, between 10 mL/minute and 500 mL/minute, between 10 mL/minute and 100 mL/minute, and preferably between 50 mL/minute and 100 mL/minute through the first inner fluid conduit 3165. In some embodiments, the first fluid exits the exit orfice 3163 of the first inner fluid conduit 3165 and enters the first fluid contacting chamber 3125, whereupon the first fluid 3115 comes in physical communication with the second fluid 3170. In some embodiments, the second fluid 3170 travels at a volumetric flow rate between 2 mL/minute and 1,000 mL/minute, between 10 mL/minute and 500 mL/minute, between 10 mL/minute and 100 mL/minute, and preferably between 50 mL/minute and 100 mL/minute, through a second inner fluid conduit 3175. In a typical embodiment, the first fluid 3115 is an emulsion without any lipids that could interact with the active agent (e.g. no charged lipid such as DPPG) In another embodiment, the second fluid 3170 is a volatile solvent comprising a lipid solution (could be the same or different than that used in the first component).

In some embodiments, the first fluid 3115 travels through the first fluid contacting chamber 3125, surrounded by the second fluid 3170. In some embodiments, the first fluid 3115 and the second fluid 3170 continue through the first fluid contacting chamber 3125 into the second fluid contacting chamber 3137. In some embodiments, the second fluid 3170 forms a sheath around the first fluid 3115 core.

In some embodiments, the first and second fluids can travel at a volumetric flow rate between 2 mL/minute and 1,000 mL/minute, between 10 mL/minute and 500 mL/minute, between 10 mL/minute and 100 mL/minute, and preferably between 50 mL/minute and 100 mL/minute through the second inner conduit 3175. In some embodiments, the first and second fluids exits the exit orifice 3147 the second inner conduit 3175 and enter the second fluid contacting chamber 3137, whereupon the first and second fluids come in physical communication with a third fluid 3120. In a typical embodiment, the third fluid 3120 is a buffer solution. In some embodiments, the third fluid 3120 travels at a volumetric flow rate between 2 mL/minute and 1,000 mL/minute, between 10 mL/minute and 500 mL/minute, between 10 mL/minute and 100 mL/minute, and preferably between 50 mL/minute and 100 mL/minute, through an outer fluid conduit 3123, which annularly surrounds the first inner fluid conduit 3165 and the second inner conduit 3175 (as seen from the downward perspective view F and displayed in FIG. 3F). In some embodiments, the first, second and third fluids exit the exit orifice 3145 of the second fluid contacting chamber 3137. In some embodiments, the third fluid 3120 forms a sheath around the first and second fluids.

In some embodiments, the diameter of the first fluid contacting chamber 3125 can be conically narrowed as it approaches the exit orifice 3163 of the first inner fluid conduit 3165. As the first fluid 3115 travels through the narrowing first fluid contacting chamber 3125 and toward the exit orfice 3147 of the second fluid conduit 3175, the diameter of the first fluid 3115 core is correspondingly decreased. Likewise, the second fluid 3170 can be constricted to create a thinner concentric annular sheath around the first fluid 3115 core. As a result of decreasing the diameter of the first fluid contacting chamber 3125 and passing the fluids through the exit orifice 3147 of the second fluid conduit 3175, the velocities of the first fluid 3115 and the second fluid 3170 are increased.

In some embodiments, the diameter of the second fluid contacting chamber 3125 can be conically narrowed as it joins the cylindrical tip 3145. As the first fluid 3115 core and second fluid 3120 travel through the narrowing second fluid contacting chamber 3125 into the cylindrical tip 3145, the diameter of the first fluid 3115 core, the second fluid 3120 the third fluid 3170 can be further correspondingly decreased. Likewise, the third fluid 3170 can be constricted to create a thinner concentric annular sheath around the first fluid 3115 core and the second fluid 3120 sheath. In some embodiments, the multi vesicular liposomes are lipid coated with lipids on the outside that are different than the lipids on the inside. In some embodiments, the four fluid nozzle illustrated in FIG. 3E and FIG. 3I could be used to manufacture multi vesicular liposomes coated with an additional layer of polymer PLGA or a highly charged phospholipid different from the phospholipid of the internal membrane. These multi vesicular liposomes coated with an extra layer of polymer or phospholipid or combination thereof constitute further embodiments as disclosed herein.

The four fluid atomizing nozzle 320 comprises a gas input channel 3130 which supplies a gas 3140. In some embodiments, the volumetric flow rate of the gas can be between 30 L/minute and 1,000 L/minute, between 30 L/minute and 500 L/minute, between 20 L/minute and 200 L/minute, and preferably between 25 L/minute and 100 L/minute and at a pressure between 5 psig and 1,000 psig, between 10 psig and 250 psig, between 20 psig and 150 psig, and preferably between 50 psig and 120 psig to the annular gas chamber 3135. The above atomizing nozzle flow rates are for a single atomizing nozzle. Prior to reaching the nozzle 320, the gas 3140 can be passed through a gas filtration system (not shown) comprising a hydrophobic gas sterilizer (as seen in FIG. 1A and FIG. 1B, component 35). In some embodiments, the outlet of the cylindrical tip 3145 and the outlet of the exit orifice 3147 of the first second contacting chamber 3137 have the same diameter. In some embodiments, the diameter of the outlet of the cylindrical tip 3145 is larger than the diameter of the outlet of the exit orfice 3147 of the second fluid contacting chamber 3137. In some embodiments, the diameter of the outlet of the cylindrical tip 3145 is smaller than the diameter of the exit orfice 3147 of the second fluid contacting chamber 3137.

FIG. 3G shows an expanded cross-sectional view of the first fluid, second fluid and third fluid in the cylindrical tip 3145.

FIG. 3H shows an expanded cross-sectional view of the first fluid, second fluid and third fluid in a droplet 3255

FIG. 3I

FIG. 3I is a schematic partial cross-sectional view of a four fluid atomizing nozzle 320, comprising a first inner fluid conduit 3165, a second inner conduit 3175, an outer conduit 3123, a fluid contacting chamber 3125, a gas input channel 3130, an annular gas chamber (a fourth fluid conduit) 3135, and an annular gas orifice 3150. In some embodiments, the fluid contacting chamber 3125 is conically tapered from the exit orfice 3173 of an outer fluid conduit 3123 to a cylindrical tip 3145.

The fluid contacting chamber 3125 is annularly surrounded by an annular gas chamber 3135, which narrows to form an annular gas orifice 3150. The bottom portion of the cylindrical tip 3145 is annularly and concentrically surrounded by the annular gas orifice 3150.

In some embodiments, a first fluid 3115 can travel at a volumetric flow rate between 2 mL/minute and 1,000 mL/minute, between 10 mL/minute and 500 mL/minute, between 10 mL/minute and 100 mL/minute, and preferably between 50 mL/minute and 100 mL/minute through the first inner fluid conduit 3165. In a typical embodiment, the first fluid 3115 is an emulsion. In some embodiments, the first fluid exits the bottom 3163 of the first inner fluid conduit 3165 and enters the fluid contacting chamber 3125, whereupon the first fluid 3115 comes in physical communication with a second fluid 3170. In some embodiments, a second fluid 3170 exits the bottom 3173 of the second inner conduit 3175 and enters the fluid contacting chamber 3125, whereupon the second fluid 3170 comes in physical communication with the first fluid 3115 and a third fluid 3170. In a typical embodiment, the first fluid 3115 in the first inner fluid conduit 3165 is annularly surrounded by the second fluid 3170 in the second inner conduit 3175 which is annularly surrounded by the third fluid 3120 in the outer conduit 3123 (as seen from the downward perspective view J and displayed in FIG. 3J).

In some embodiments, the first fluid 3115 travels through the first fluid contacting chamber 3125, surrounded by the second fluid 3170 which is surrounded by the third fluid 3120. In some embodiments, the second fluid 3170 forms a sheath around the first fluid 3115 and the third fluid 3120 forms a sheath around the first and second fluids.

In some embodiments, the diameter of the fluid contacting chamber 3125 can be conically narrowed as it joins the cylindrical tip 3145. In some embodiments, as the first fluid 3115 travels through the narrowing first fluid contacting chamber 3125 and toward the cylindrical tip 3145, the diameter of the first fluid 3115 core is correspondingly decreased. In some embodiments, the second fluid 3170 can be constricted to create a thinner concentric annular sheath around the first fluid 3115 core. In some embodiments, the third fluid 3120 can be constricted to create a thinner concentric annular sheath around the first fluid 3115 core and the concentric annular second fluid 3170. As a result of decreasing the diameter of the first fluid contacting chamber 3125 and passing the fluids through the cylindrical tip 3145, the velocities of the first fluid 3115, second fluid 3170 and third fluid 3120 can be increased.

The four fluid atomizing nozzle 320 comprises a gas input channel 3130 which supplies a gas 3140. In some embodiments, the volumetric flow rate of the gas can be between 30 L/minute and 1,000 L/minute, between 30 L/minute and 500 L/minute, between 20 L/minute and 200 L/minute, and preferably between 25 L/minute and 100 L/minute and at a pressure between 5 psig and 1,000 psig, between 10 psig and 250 psig, between 20 psig and 150 psig, and preferably between 40 psig and 120 psig to the annular gas chamber 3135. The above atomizing nozzle flow rates are for a single atomizing nozzle. Prior to reaching the nozzle 320, the gas 3140 can be passed through a gas filtration system (not shown) comprising a hydrophobic gas sterilizer (as seen in FIG. 1A and FIG. 1B, component 35).

FIG. 3K shows an expanded cross-sectional view of the first fluid, second fluid and third fluid in the cylindrical tip 3145.

FIG. 3L shows an expanded cross-sectional view of the first fluid, second fluid and third fluid in a droplet 3255.

FIG. 4A

FIG. 4A depicts an atomizing nozzle 410 where the first fluid 4115 can break down into large droplets in the fluid contacting chamber 4125 prior to reaching the cylindrical tip 4145.

In some embodiments, a first fluid 4115 exits a inner fluid conduit 4165 through the exit orfice 4163 of the inner fluid conduit 4165 and enters the fluid contacting chamber 4125, whereupon the first fluid 4115 comes in physical communication with a second fluid 4120. The second fluid 4120 travels through an outer fluid conduit 4123, which annularly surrounds the inner fluid conduit 4165 (as seen from the downward perspective view B and displayed in FIG. 4B), to reach the fluid contacting chamber 4125. The first fluid 4115 forms a plurality of first fluid droplets 4157 traveling through the fluid contacting chamber 4125, the first fluid droplets 4157 now being in physical communication with, and surrounded by, the second fluid 4120. In some embodiments, the first and second fluid are immiscible. In a typical embodiment, the first fluid 4115 is an emulsion and the second fluid 4120 is a buffer solution.

Figure 5:
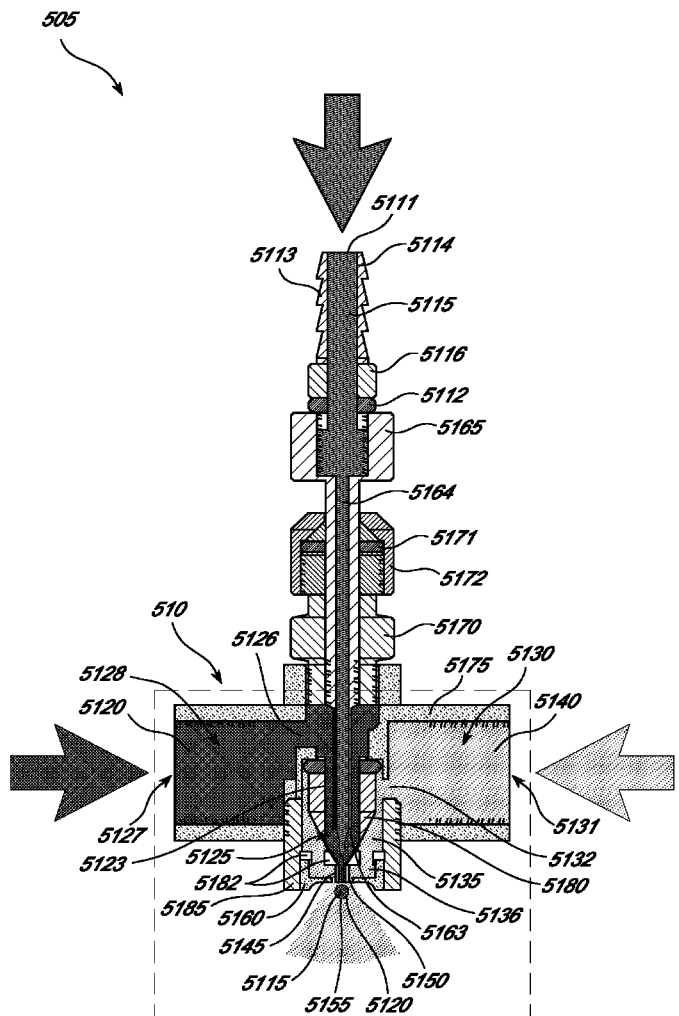
FIG. 5 is a detailed view of one embodiment of an atomizing nozzle used in a manufacturing system, such as the manufacturing system of FIG. 1A or FIG. 1B.
Figure 6:
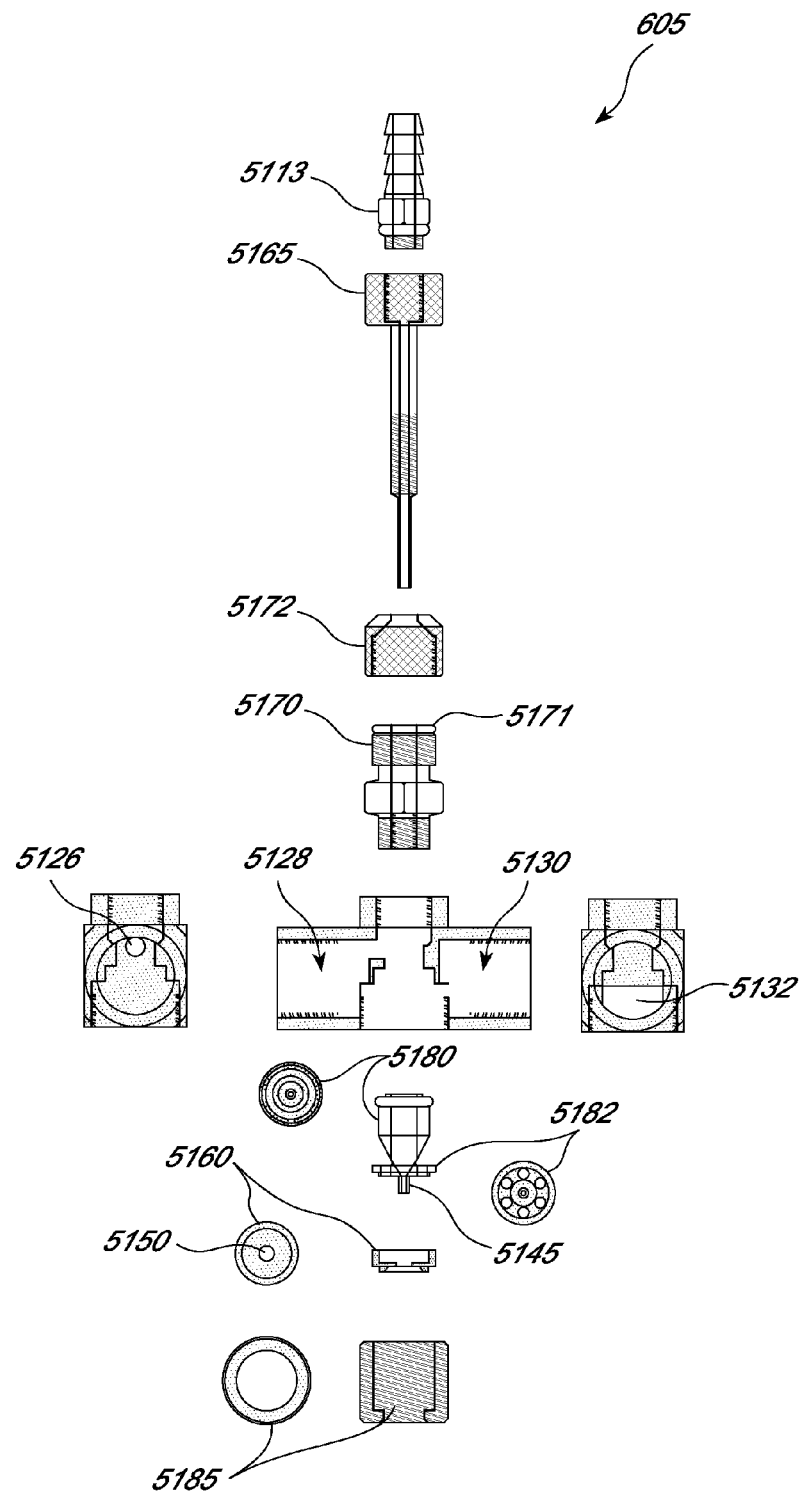
FIG. 6 is an exploded view of the individual components of the atomizing nozzle of FIG. 5.

In some embodiments, the diameter of the fluid contacting chamber 4125 is conically narrowed as it joins the cylindrical tip 4145. As the first fluid 4115 travels through the narrowing fluid contacting chamber 4125 and into the cylindrical tip 4145, the first fluid droplets 4157 are squeezed and their diameter is correspondingly decreased along the axis of travel. Likewise, the second fluid 4120 is constricted to create a thinner shell around the first fluid droplets 4157. As a result of decreasing the diameter of the fluid contacting chamber 4125 and passing the solutions through the cylindrical tip 4145, the velocities of the first fluid droplets 4157 and second fluid 4120 are increased. In a typical embodiment, the first fluid 4115 is an emulsion and the second fluid 4120 is a buffer solution.

FIG. 4C shows an expanded cross-sectional view of the first fluid droplets 4157 and second fluid 4120 in the cylindrical tip 4145.

FIG. 4D shows an expanded cross-sectional view of the first fluid and second fluid in a droplet 4155. In some embodiments, the ratio of the diameters of the first fluid to the second fluid in a droplet 4155 can be the same as the ratio of the diameters of the first fluid in the inner fluid conduit 4165 to the second fluid in the outer fluid conduit 4123. In some embodiments, the ratio of the diameters of the first fluid to the second fluid in a droplet 4155 can be the larger than the ratio of the diameters of the first fluid in the inner fluid conduit 4165 to the second fluid in the outer fluid conduit 4123. In some embodiments, the ratio of the diameters of the first fluid to the second fluid in a droplet 4155 can be the smaller than the ratio of the diameters of the first fluid in the inner fluid conduit 4165 to the second fluid in the outer fluid conduit 4123.

The nozzle 410 comprises a gas input channel 4130 which supplies a gas 4140 to an annular gas chamber (a third fluid conduit) 4135. Prior to reaching the nozzle 410, the gas 4140 can be passed through a gas filtration system (not shown) comprising a hydrophobic gas sterilizer (FIG. 1A and FIG. 1B, component 35). The wall of the fluid contacting chamber 4125 provides a barrier between the annular gas chamber 4135 and the fluid contacting chamber 4125 such that there is no physical contact between the fluids in the fluid contacting chamber 4125 and the gas 4140 in the annular gas chamber 4135. In some embodiments, the outlet of the cylindrical tip 4145 and the outlet of the annular gas orifice 4150 can be flush with each other such that the second fluid 4120 does not come into contact with the gas 4140 prior to the gas 4140 exiting the atomizing nozzle 410. In other embodiments, the cylindrical tip 4145 may extend below the end of the annular gas orifice 4150. In still other embodiments, the cylindrical tip 4145 may be slightly recessed within the annular gas orifice 4150, such that the gas 4140 comes into physical communication with the second fluid 4120 prior to the second fluid fully exiting from the nozzle 410. In a typical embodiment, the first fluid 4115 is an emulsion and the second fluid 4120 is a buffer solution.

In some embodiments, as the gas 4140 passes through the annular gas orifice 4150 and exits the atomizing nozzle 410, it comes in physical communication with the second fluid 4120 and acts to shear the stream of the second fluid 4120 and the first fluid 4115 droplets into atomized droplets 4155 made of a first fluid 4115 core and a second fluid 4120 shell. In this embodiment the first fluid core stream breaks up due to the mismatch of velocities between the first fluid 4115 and the second fluid 4120 at the exit orfice 4163 of the inner fluid conduit 4165. In a typical embodiment, the first fluid 4115 is an emulsion and the second fluid 4120 is a buffer solution.

FIG. 5

FIG. 5 is a more detailed view of one embodiment of an atomizing nozzle 505. The nozzle depicted in FIG. 5 is derived from Part No. 1/8JJN-SS+SUJ1A-SS manufactured by Spraying Systems Co. of Wheaton, Ill., as modified in FIG. 5 and described herein. The atomizing nozzle lower section 510 of FIG. 5 provides three fluid input channels for the introduction of three fluids into the nozzle 505. A first fluid input channel is the central longitudinal channel 5114, which extends substantially downwardly through the atomizing nozzle lower section 510 and extends into a fluid contacting chamber 5125. In some embodiments, a second fluid input channel is a buffer input channel 5128 and a third fluid input channel is a gas input channel 5130.

The central longitudinal channel 5114 is a channel which may be of circular cross-section. The central longitudinal channel 5114 may begin as an aperture 5111 in a line coupler 5113. The line coupler 5113 is a means for attaching a supply line to the nozzle 505 for the introduction of the first fluid 5115 into the nozzle lower section 510. A polymeric sealing washer 5112 is retained in contact with the line coupler 5113 and interposed between a coupler nut 5116 of the line coupler 5113 and a head (not shown) of a inner fluid conduit 5165.

The inner fluid conduit 5165 can provide a continuation of the central longitudinal channel 5114, with a narrowed central bore 5164 extending through a removable housing member 5170 into the horizontal channel casing 5175, and into the liquid fluid cap 5180, ending in the fluid contacting chamber 5125 of the liquid fluid cap 5180. In some embodiments, the housing member 5170 can be threaded. The housing member 5170 can be fitted on the top with a housing cap 5172 and housing gasket member 5171 to provide secure fastening and fluid seal. The housing member 5170 extends downwardly into a top portion of the horizontal channel casing 5175, wherein it can be tightened to form a secure connection with the horizontal channel casing 5175, for example using internal screw threading.

In addition to the central longitudinal channel 5114, the horizontal channel casing 5175 can be comprised of the gas input channel 5130 and the buffer input channel 5128. The gas input channel 5130 can have an external aperture 5131 to which a gas supply line (not shown) can be to be attached. The gas input channel 5130 can have an internal aperture 5132 which leads to an annular gas chamber (third fluid conduit) 5135, the annular gas chamber 5135 situated to annularly surround the liquid fluid cap 5180. The liquid fluid cap 5180 can be detachably and securely fitted into the horizontal channel casing 5175 such that fluid contents of the liquid fluid cap 5180 and the fluid contacting chamber 5125 cannot physically communicate with the fluid contents of the annular gas chamber 5135 inside the nozzle. The buffer input channel 5128 can have an external aperture 5127 to which a fluid supply line (not shown) can be attached. The buffer input channel 5128 can have an internal aperture 5126 which leads to the top opening of the liquid fluid cap 5180.

In some embodiments, the liquid fluid cap 5180 can be cylindrically shaped in a top portion and conically tapered in a exit orfice portion. In some embodiments, the liquid fluid cap 5180 can be cylindrically tapered in both a top portion and a bottom portion. In some embodiments, the fluid contacting chamber 5125 and the outer fluid conduit 5123 form the interior wall of the liquid fluid cap 5180. The fluid contacting chamber 5125 is conically tapered from the exit orfice of an annular outer fluid conduit 5123 to a cylindrical tip 5145. The exit orfice portion of the cylindrical tip 5145 can be annularly and concentrically surrounded by an annular gas orifice 5150. The annular gas orifice 5150 can be created by placement of the cylindrical tip 5145 in the center of a cylindrical opening in a gas cap 5160. The liquid fluid cap 5180 can have a gas restrictor 5182 attached to the exterior of the liquid fluid cap 5180 with several circular holes in the gas restrictor 5182, which annularly surrounding the liquid fluid cap 5180. The presence of the gas restrictor 5182 creates a lower annular gas chamber 5136 between the gas restrictor 5182 and the gas cap 5160. The gas restrictor 5182 can minimize the turbulence possibly created as a gas travels through the annular gas chamber 5135 to the annular gas orifice 5150. The nozzle lower section 510 can be fitted to an orifice housing 5185 which acts to keep the gas cap 5160 and liquid fluid cap 5180 securely fitted to the horizontal channel casing 5175. In some embodiments, the orifice housing 5185 can be threaded.

In some embodiments, the first fluid 5115 can enter the longitudinal channel 5114 of the nozzle lower section 510 from a supply line (not shown) attached to the line coupler 5113. The first fluid travels through the longitudinal channel 5114 until it reaches the fluid contacting chamber 5125 whereupon it comes in physical contact with the second fluid 5120 in the fluid contacting chamber 5125. In a typical embodiment, the first fluid 5115 is an emulsion and the second fluid 5120 is a buffer solution.

In some embodiments, the second fluid 5120 enters the nozzle lower section 510 through an input aperture 5127 and travels through the input channel 5128. In some embodiments, the second fluid 5120 then passes through the internal aperture 5126 leading to the top of the liquid fluid cap 5180 and travels through the annular outer fluid conduit 5123, and travels around and surrounds the inner fluid conduit 5165 at a lower section to reach the fluid contacting chamber 5125. In some embodiments, upon exiting the exit orfice 5163 of the inner fluid conduit 5165 or the central longitudinal channel 5114 and entering the fluid contacting chamber 5125, the first fluid 5115 can form a cylindrical core traveling through the fluid contacting chamber 5125. In some embodiments, the first fluid 5115 cylindrical core can be surrounded annularly by the second fluid 5120. In some embodiments, the immiscibility between the second fluid 5120 and the first fluid 5115, and because of the high velocity at which the second fluid 5120 and first fluid 5115 are traveling, causes the second fluid 5120 to form a sheath around the first fluid 5115 core. The first fluid 5115 and second fluid 5120 can travel through the fluid contacting chamber 5125 into the cylindrical tip 5145 of the outer conduit 5123. In a typical embodiment, the first fluid 5115 is an emulsion and the second fluid 5120 is a buffer solution.

The cross-sectional diameter of the fluid contacting chamber 5125 decreases as it conically narrows to join the cylindrical tip 5145. As the first fluid 5115 travels through the narrowing fluid contacting chamber 5125 and into the cylindrical tip 5145 the diameter of the first fluid 5115 core is decreased. Likewise, the second fluid 5120 can be constricted to create a thinner concentric annular sheath around the first component 5115 core. In some embodiments, as the solutions pass through the narrowing cylindrical tip, the velocities of the first fluid 5115 and the second fluid 5120 can be increased. In some embodiments, the threads on the inner fluid conduit 5165 and the housing member 5170 allow the outlet tip of the inner fluid conduit 5165 to be adjusted vertically within the conical portion of the fluid contacting chamber 5125 within the liquid fluid cap 5180. In some embodiments, the housing member 5170 can be adjusted so that the velocities of the second fluid 5120 and the first fluid 5115 can be made approximately equal at the point where the first fluid 5115 exits the inner fluid conduit 5165. This allows optimal operation as shown in FIG. 3A. In some embodiments, the housing member 5170 can be adjusted so that the velocities of the second fluid 5120 and the first fluid 5115 can be made uequal at the point where the first fluid 5115 exits the inner fluid conduit 5165. This allows optimal operation as shown in FIG. 4A. In a typical embodiment, the first fluid 5115 is an emulsion and the second fluid 5120 is a buffer solution.

In some embodiments, a gas 5140 can be first passed through a gas filtration system (not shown) comprising a hydrophobic gas sterilizer (not shown). In some embodiments, the gas 5140 can enter the gas input channel 5130 through the external gas input aperture 5131 and then passes through the internal gas chamber aperture 5132 to reach the annular gas chamber 5135. In some embodiments, the liquid fluid cap 5180 can be detachably and securely fitted into the horizontal channel casing 5175 such that the gas 5140 cannot physically communicate with the first fluid 5115 or the second fluid 5120 inside the nozzle lower section 510. The gas 5140 travels through the holes in the gas restrictor 5182 to reach the lower annular gas chamber 5136.

As the gas 5140 passes through the annular gas orifice 5150 and exits the atomizing nozzle lower section 510, it comes in physical communication with the second fluid 5120 and acts to shear the stream of the second fluid 5120 and first fluid 5115 into atomized droplets 5155 made of a first fluid 5115 core and a second fluid 5120 shell. In a typical embodiment, the first fluid 5115 is an emulsion and the second fluid 5120 is a buffer solution. In a typical embodiment, the first fluid 5115 core is an emulsion and the second fluid 5120 shell is a buffer solution.

Some embodiments provide an atomizing nozzle apparatus, comprising three channels, each having at least one entrance orifice and one exit orifice, the channels comprise of an inner fluid conduit and an outer fluid conduit, wherein the exit orifice for the inner fluid conduit is of a diameter smaller than, and is located centrally in, the outer fluid conduit and is directed towards the outer fluid conduit exit orifice, a gas channel, wherein a pressurized gas exiting the gas channel exit orifice impinges a liquid exiting the exit orifice of the outer fluid conduit. Additional embodiments include the processes for using such a device and the MVL products made by the same. In some embodiments, the gas channel exit orifice can annularly surround the exit orifice of the outer fluid conduit. In some embodiments, the gas channel exit orifice and the outer fluid conduit exit orifice can be flush. In some embodiments, the outer fluid conduit exit orifice can be recessed within the gas channel exit orifice. In some embodiments, the outer fluid conduit exit orifice can extend beyond the gas channel exit orifice. In some embodiments, the exit orifices of all three channels can be coaxial. In some embodiments, the exit orifice of the inner fluid conduit can be more than two outer fluid conduit exit orifice diameters away from the outer fluid conduit exit orifice.

In some embodiments, the multi vesicular liposome product produced by the atomizing nozzle in FIGS. 3-6 can be directly collected and purified. Alternatively, the MULTI VESICULAR LIPOSOME product can be processed by an evaporation tower or the evaporation apparatus of FIG. 7 (or as part of FIGS. 1A-1C) before being processed.

FIG. 6

FIG. 6 is an exploded schematic 605 of the individual components of the device of FIG. 5.

In some embodiments, component 5113 is a line coupler; component 5165 is an inner fluid conduit; component 5172 is a housing cap; component 5170 is a housing member; component 5171 is a housing gasket member; component 5180 is a liquid fluid cap; component 5145 is a cylindrical tip; component 5160 is a gas cap; component 5182 is a gas restrictor; and component 5185 is an orifice housing.

In some embodiments, location 5130 can be a gas input channel; location 5132 can be an internal gas chamber aperture; location 5128 can be a fluid channel; location 5126 can be an internal fluid cap aperture; and location 5150 can be an annular gas orifice.

FIG. 7

An embodiment of the present application is a system for manufacturing formulations including an evaporation apparatus, or evaporation sub-system, the process of using the system, and the large diameter synthetic membrane vesicles products made by the process. An example of an evaporation apparatus is the solvent removal vessel presented in FIG. 7 and described herein. FIG. 7 shows a schematic of a solvent removal vessel 710. In some embodiments, atomized droplets 7155 can be sprayed into the solvent removal vessel 710 in order to remove solvent from atomized droplets 7155. In some embodiments, the solvent removal vessel 710 can include a three-fluid atomizing nozzle 7510, described above, attached to and extending through a lid 7220 of the solvent removal vessel 710. In some embodiments, the cylindrical tip and annular gas orifice of the atomizing nozzle 7510 can be configured to be substantially flush with the inside edge of the lid 7220. In some embodiments, the cylindrical tip and annular gas orifice of the atomizing nozzle 7510 can be configured to extend beyond the inside edge of the lid 7220.

Alternatively, in some embodiments, the solvent removal vessel 710 can include a three-fluid atomizing nozzle 7510, described above, attached to and extending through a wall 7350 of the solvent removal vessel 710. In some embodiments, the cylindrical tip and annular gas orifice of the atomizing nozzle 7510 can be configured to be substantially flush with the inside edge of the wall 7350. In some embodiments, the cylindrical tip and annular gas orifice of the atomizing nozzle 7510 can be configured to extend beyond the inside edge of the wall 7350.

In some embodiments, the vessel 710 also includes a gas outlet tube 7340, which can pass through the center of the lid 7220, and extend into a solvent removal chamber 7230. In some embodiments, the gas outlet tube 7340 can extend down from the lid from about 15 to about 19 inches and can be about 1 inch in diameter. In some embodiments, the gas outlet tube 7340 can extend down from the lid from about 20 cm to about 60 cm and can be from about 1 cm to about 4 cm in diameter. In some embodiments, a conical fitting 7300 can be attached to the end of the gas outlet tube 7340. In some embodiments, the conical fitting 7300 can be used to narrow the diameter of the gas outlet tube 7340 at a gas outlet 7310. In some embodiments, the gas outlet 7310 can be approximately 0.5 inches in diameter. In some embodiments, the gas outlet 7310 can be from about 0.5 cm to about 3 cm in diameter. In some embodiments, a vortex stabilizer disk or ring 7360 can be attached to the conical fitting 7300.

In some embodiments, a gas inlet pipe 7290 can be connected to the wall 7350 of the solvent removal vessel 710 can be creating a gas inlet 7280. In some embodiments, the solvent removal vessel 710 has a bottom 7250, which can include a product exit orifice 7260. In some embodiments, the exit orifice 7260 can be in the center of the domed bottom 7250. In some embodiments, a product outlet pipe 7270 can be attached to the exit orifice 7260. In some embodiments, the solvent removal vessel 710, includes a temperature control jacket (not shown). In some embodiments, temperature controlling fluid can be circulated through a temperature control jacket (not shown) of the solvent removal vessel 710, wherein the temperature control jacket can surround the wall 7350 and the bottom 7250 of the solvent removal vessel 710 for temperature regulation in the solvent removal chamber 7230. In some embodiments, the bottom 7250 of the solvent removal vessel 710 could be of a shape such as a dome, a cone or an angled flat bottom.

In some embodiments, a carrier gas 7370 can be first heated and humidified and then passed through a gas filtration system (not shown) comprising a hydrophobic gas sterilizer (not shown). In some embodiments, the carrier gas 7370 can be supplied to the solvent removal vessel 710 through the gas inlet pipe 7290. In some embodiments, the carrier gas 7370 can pass through the gas inlet 7280 and enter a gas rotation jet 7285. In some embodiments, the gas rotation jet 7285 directs the flowing carrier gas 7370 inside the solvent removal chamber 7230 such that the carrier gas 7370 exits the gas rotation jet 7285 (and enters the solvent removal chamber 7230) horizontally and in a direction tangential to the solvent removal vessel wall 5350. In some embodiments, substantially all the carrier gas 7370 entering the solvent removal chamber 7230 through the gas rotation jet 7285 can exit the solvent removal chamber 7230 through the gas outlet 7310 and gas outlet pipe 7340.

In some embodiments, the carrier gas 7370 supplied to solvent removal chamber 7230 can be injected tangential to the wall 7350, causing the carrier gas 7370 to first travel slowly clockwise (as viewed from above) around the solvent removal vessel 710 near the wall 7350, and forming a slow gas rotation 7240. In some embodiments, the solvent removal chamber 7230 can be pressured to approximately 1 psig, creating a pressure differential between the solvent removal chamber 7230 and the gas outlet pipe 7340. In some embodiments, the carrier gas 7370 traveling in the solvent removal chamber 7230 can be pulled inwards, as it circulates, towards the gas outlet 7310. In some embodiments, the change in angular momentum on the carrier gas 7370 causes the carrier gas 7370 to accelerate as it moves closer to the gas outlet 7310. In some embodiments, the acceleration of the carrier gas 7370 near the gas outlet 7310 can be sufficiently strong to create an intense gas vortex 7245 underneath the vortex stabilizer 7360 and gas outlet 7310. In some embodiments, the carrier gas 7370 can be pushed out of the solvent removal chamber 7230 through the gas outlet 7310 into the gas outlet pipe 7340 for disposal after spinning through the gas vortex 7245.

In some embodiments, the three-fluid atomizing nozzle 7510 can be supplied with a first fluid 7115, a second fluid 7120, and a third fluid 7140, as described above. In a typical embodiment, the first fluid can be a first component, the second fluid can be a buffer solution, and the third fluid can be a gas. In some embodiments, the resultant atomized droplets 7155, comprised of a first fluid core and a second fluid shell, can be sprayed into the solvent removal chamber 7230. In some embodiments, the atomized droplets 7155 come into contact with the carrier gas 7370 being circulated in the slow gas rotation 7240 as the atomized droplets 7155 can travel down through the solvent removal chamber 7230. In some embodiments, the atomized droplets 7155 can be picked up by, and incorporated in, the slow gas rotation 7240 and begin to circulate through the solvent removal chamber 7230, and begin to settle toward the domed bottom 7250.

In some embodiments, the solvent can be substantially evaporated from the core of the atomized droplets 7155 as the atomized droplets 7155 circulate along with the carrier gas 7370 in the slow gas rotation 7240. In some embodiments, the evaporated solvent can be removed from the solvent removal chamber 7230 along with the circulating carrier gas 7370 through the gas outlet 7310 and into the gas outlet pipe 7340 for disposal. In some embodiments, the gas outlet pipe 7340 can be equipped with a sterile barrier filtration system (not shown) outside of solvent removal vessel 710. The filtration system in one embodiment can be comprised of filter (e.g. a course filter or conventional cyclone separator) and a HEPA filter or other sterilizing gas filter.

In some embodiments, a portion of the atomized droplets 7155, traveling in the slow gas rotation 7240, can reach the intense gas vortex 7245, where they can be kicked outwards again by the intense centrifugal forces within the intense gas vortex 7245, and thus are not removed through the gas outlet 7310. For example, some of the atomized droplets 7155 kicked outwards by the gas vortex 7245 can travel again through the slow gas rotation 7240 and some of the atomized droplets begin to fall towards the domed bottom 7250. In one embodiment, very few of the atomized droplets 7155 escape with the carrier gas 7370 through the gas outlet 7310. In some embodiments, removal of substantially all the solvent from the atomized droplets 7155 can afford large diameter synthetic membrane vesicles droplets 7380 still coated in a fluid shell. In some embodiments, droplets 7380 permanently fall out of the gas vortex primarily to the domed bottom 7250 of the solvent removal vessel 710. In some embodiments, the plurality of large diameter synthetic membrane vesicles droplets 7380 form a suspension 7390 of large diameter synthetic membrane vesicles particles in a solution at the domed bottom 7250. In a typical embodiment, the large diameter synthetic membrane vesicles are multivesicular liposomes.

The solvent removal vessel 710 can optionally be equipped with a two-fluid rinse nozzle 7400 in the lid 7220 of the solvent removal vessel 710. In some embodiments, the two-fluid rinse nozzle 7400 can be positioned in the lid 7220 at 90 degrees clockwise from the atomizing nozzle 7510. In some embodiments, the two-fluid rinse nozzle 7400 can be positioned in the lid 7220 at 180 degrees clockwise from the atomizing nozzle 7510. The rinse nozzle 7400 can be fed a wall rinse solution 7410 and a filtered gas 7420 in order to spray atomized wall rinse solution droplets 7415 into the solvent removal vessel 710 for the purpose of rinsing any wayward atomized emulsion droplets from the wall 7350 and rinsing the large diameter synthetic membrane vesicles suspension 7390 to the product exit orifice 7260. In a typical embodiment, the large diameter synthetic membrane vesicles are multivesicular liposomes.

In some embodiments, solvent removal vessel 710 can be optionally equipped with a lid-protecting gas inlet 7430 in the lid 7220. In some embodiments, solvent removal vessel 710 can be optionally equipped with a lid-protecting gas inlet 7430 in the lid 7220 on a side opposite the atomizing nozzle 7510. In some embodiments, humidified, sterilized, and filtered gas 7440 can be streamed into the solvent removal chamber 7230 in a direction tangential to the solvent removal vessel wall 7350 through the lid-protecting gas inlet 7430, near the top of the solvent removal chamber 7230. In some embodiments, gas 7440 can travel circularly, as a lid protection jet, around the top of solvent removal chamber 7230 and, in essence, acts a gas cushion above the gas vortex 7245 and slow gas rotation 7240 to prevent droplet buildup on the lid 7220. In some embodiments, the gas streamed through the lid-protecting gas inlet can be, for example, nitrogen gas (or a nitrogen gas/aqueous vapor mixture) or air scrubbed of $CO_2$. In some embodiments, the carrier gas can be nitrogen gas (or a nitrogen gas/aqueous vapor mixture) or air scrubbed of $CO_2$.

In some embodiments, the vortex stabilizer 7360 can be a metal disk or ring extending radially outward from the conical fitting 7300 and can be fitted flush with the gas outlet 7310 at the end of the conical fitting 7300. In some embodiments, the diameter of the vortex stabilizer 7360 is twice to six times the diameter of the gas outlet 7310. In some embodiments, the vortex stabilizer 7360 acts to ensure helical stability and integrity of the intense gas vortex 7245 by protecting the tip of the intense gas vortex 7245 from the turbulence caused by the spray emanating from the atomizing nozzle 7510. In some embodiments, the stability of the gas vortex 7245 can be maintained by placement of the atomizing nozzle 7510 at a distance between ¼ lid radius from the wall 7350 and ¼ lid radius from the gas outlet pipe 7340. In some embodiments, the atomizing nozzle 7510 can be positioned at a distance of $7/11$ the radius of the lid 7220 from the gas outlet pipe 7340. Strategic placement of the atomizing nozzle 7510 minimizes the impact on the intense gas vortex 7245 of spraying the atomized droplets 7155 into the solvent removal chamber 7230 and also minimizes the number of the atomized droplets 7155 that impinge on the wall 7350. In some embodiments, the rinse nozzle 7400 placement is not critical as long as a substantial quantity of rinse solution droplets 7415 enter the slow gas rotation 7240 within the solvent removal vessel 7240 and deposit on the vessel walls 7350 and bottom 7250. In some embodiments, the rinse nozzle 7400 can also be of a one fluid (liquid) design fed by pressurized rinse solution. In some embodiments, the nozzle can be 180 degrees from the three fluid nozzle to suppress off access gas rotation.

In some embodiments, the suspension 7390 collected at the domed bottom 7250 of the solvent removal vessel 710 can be drained and optionally pumped by a pump (not shown) from the domed bottom 7250 through the product exit orifice 7260 into the product outlet pipe 7270 to optionally be further processed. In some embodiments, the suspension 7390 can be further processed by a buffer exchange through a series of diafilters.

Figure 7:
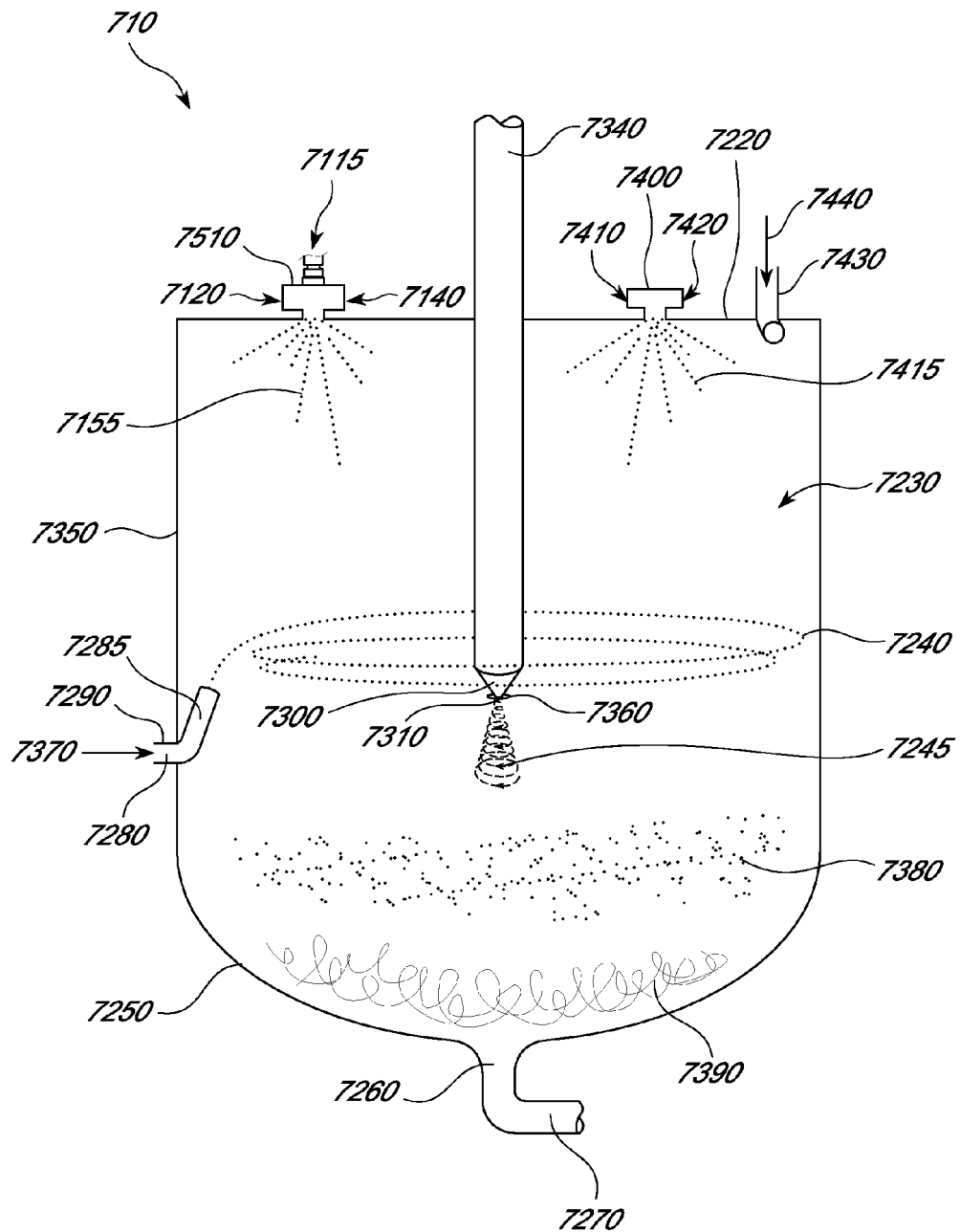
FIG. 7 is a schematic of one embodiment of a solvent removal vessel used for evaporating solvent from atomized particles in a manufacturing system such as the manufacturing system of FIG. 1A or FIG. 1B.

In some embodiments, the solvent removal vessel of FIG. 7 can be a component of FIGS. 1A and B (component 50). In some embodiments, the atomizing nozzle 7510 can receive fluid from the line 2180 of FIG. 2. In some embodiments, the large diameter synthetic membrane vesicles suspension 7390 can exit the solvent removal vessel of FIG. 7 through the product exit orifice 7260 and can enter the systems of FIG. 1C (through line 120), FIG. 8 (through line 8120), FIG. 10 (through line 0120) and/or FIG. 11 (through line 1120). Alternatively, the large diameter synthetic membrane vesicles suspension 7390 can be collected directly from the product exit orifice 7260.

In some embodiments, the apparatus is configured where the gas inlet can be situated in the chamber to cause the gas to rotate within the chamber around an axis of the chamber and a small diameter gas exit orifice situated on that same axis and adapted to form a small diameter, in relation to the tank diameter, intense rapidly rotating gas vortex capable of substantially preventing atomized droplets from exiting through the gas exit.

In some embodiments, the apparatus is configured where the gas inlet, tank dimensions and gas exit diameter and position are together adapted to retain the atomized droplets in the circulating gas stream rather that force them to a wall. In some embodiments, the atomized droplets can build up in the circulating gas stream until the rate of settling to the liquid exit equals the rate of generation by the atomizing nozzle.

Some embodiments provide an evaporation apparatus, comprising a sealed solvent removal vessel, comprised of a lid, a bottom, and a circular wall, at least one atomizing nozzle which is not located on the central axis of the circular wall, a carrier gas entrance orifice tangential to the circular wall, a carrier gas exit orifice located on the central axis of the circular wall and directed along the axis with a diameter of less than ⅕ of the circular wall diameter, and a product exit orifice in the bottom of the vessel. Additional embodiments include the processes for using such a device and the MVL products made by the same. In some embodiments, at least part of the vessel can be jacketed. In some embodiments, the atomizing nozzle can be mounted to and extending through the lid of the solvent removal vessel. In some embodiments, the apparatus further comprises a rinse nozzle mounted to and extending through the lid of the solvent removal vessel. In some embodiments, the atomizing nozzle can be used to cause the gas within the vessel to rotate. In some embodiments, the atomizing nozzle can be angled at least 5 degrees measured off the central axis of the wall and in a plane parallel to the wall nearest to it. In some embodiments, the gas entrance orifice can be combined with the atomizing nozzle. In some embodiments, the carrier gas exit orifice can comprise a tube extending approximately ⅔ of the way into the solvent removal vessel. In some embodiments, the tube can be fitted with a narrowing cone and an optional annular ring. In some embodiments, the gas exit orifice diameter can be less than a $1/10$ diameter of the diameter of the inside of the tank. In some embodiments, the atomizing nozzle can be a nozzle as disclosed herein. In some embodiments, the ratio of the inside diameter of the solvent removal vessel to the diameter of the carrier gas exit orifice can be between approximately 5:1 and 100:1. In some embodiments, the ratio of the inside diameter of the solvent removal vessel to the diameter of the carrier gas exit orifice can be between approximately 20:1 and 60:1. In some embodiments, the solvent removal vessel is comprised of two, three, or four atomizing nozzles which are used to spray the atomized droplets into the solvent removal vessel.

FIG. 8

In some embodiments, the large diameter synthetic membrane vesicles suspension resulting from the spray evaporation process may optionally undergo a filtration and/or concentration process in a continuous-flow particle-concentration system to concentrate the large diameter synthetic membrane vesicles and remove the buffer solution. One embodiment is a continuous-flow particle-concentration unit, as well as the process to concentrate and/or filter the large diameter synthetic membrane vesicles particles so produced. In a typical embodiment, the large diameter synthetic membrane vesicles are multivesicular liposomes. Other embodiments of particle-concentration systems include the use of one or more hydro-cyclones or one or more centrifuges. An example of a hydro-cyclone is the Minicyclone or Minicyclone Array available from ChemIndustrial Systems, Inc. of Cedarburg, Wis. An example of a disk centrifuge is Model No. Pathfinder SC1-06-177 manufactured by GEA Westfalia Separator of Oelde, Germany.

In this document the term concentration unit, concentration apparatus, concentration system, particle-concentration system, particle-concentrating device, and particle concentrator are meant to encompass units and processes that remove some or all of the particle suspending medium of a particle suspension and therefore concentrate the particles. Furthermore, the definition of these terms encompasses the exchange of the suspending medium with a new suspending medium, performed in one step or incrementally. These two processes are closely related as exchanging the suspending medium can be accomplished by concentrating the suspension and adding new suspending medium. These terms relate to concentrating the particle suspension and exchanging the suspending medium done separately or simultaneously.

An embodiment of the present application is a system for manufacturing formulations including a continuous-flow diafiltration system, the process of using the system, and the large diameter synthetic membrane vesicles made by the process. An example of a continuous-flow diafiltration system is presented in FIG. 8 and described herein. FIG. 8 is a schematic of one example of a continuous-flow diafiltration system 810. In some embodiments, the permeate discarded in the steps described herein contains a buffer solution in which large diameter synthetic membrane vesicles can be suspended as the large diameter synthetic membrane vesicles suspension exits the solvent removal vessel. In a typical embodiment, the large diameter synthetic membrane vesicles are multivesicular liposomes.

In some embodiments, the large diameter synthetic membrane vesicles suspension can be pumped from the solvent removal vessel, such as the example vessel depicted in FIG. 7 and described above, to the diafiltration system 810 through a particle suspension inlet line 8120 (also seen in FIG. 1A, component 120 and in FIG. 7, component 7270), reaching a first retentate vessel 8100. In some embodiments, for each 1 L of large diameter synthetic membrane vesicles suspension fed to the first retentate vessel 8100, a 2 L solution can be fed into the first retentate vessel 8100 through a line 8130, the solution first passing through a manual valve 8212 and a sterilizing hydrophilic filter 8170. In some embodiments, the large diameter synthetic membrane vesicles are multivesicular liposomes and the solution is a saline solution.

In some embodiments, a portion of the large diameter synthetic membrane vesicles suspension in the first retentate vessel 8100 can be pumped by pump 8110 through a cross-flow (tangential-flow) filtration module 8150. For example, this can be a hollow fiber type module. In one embodiment, the hollow fiber filter used is Model No. CFP-2-E-8A (0.2 micron) manufactured by Amersham Biosciences of Westborough, Mass. In some embodiments, the pore size of the cross-flow (tangential-flow) filtration modules 8150, 8152 and 8154, can be chosen to retain the large diameter synthetic membrane vesicles while allowing the suspending medium to pass through the filter membranes as permeate. The pumps used in the diafiltration system can be of various types, such as peristaltic or rotary lobe positive displacement pumps. In some embodiments, cross-flow recirculation pumps 8110, 8112 and 8114 operate with at least twice the permeate flow rate of their associated cross-flow filter module and preferably 3 times, 5 times or 10 times the permeate flow rates. In some embodiments, the permeate can be drawn off through a permeate line 8160 (passing through a sterilizing hydrophilic filter 8190 and a manual valve 8202), wherein for each 1 L of large diameter synthetic membrane vesicles suspension added to the first retentate vessel 8100, 2.25 L of permeate can be removed and discarded. In some embodiments, the retentate from the filtration module 8150 can be circulated back into the first retentate vessel 8100 via a retentate line 8140. In some embodiments, for each 1 L of large diameter synthetic membrane vesicles suspension added to the first retentate vessel 8100, a 0.75 L flow of the concentrated large diameter synthetic membrane vesicles suspension can be removed from the first retentate vessel 8100 through a feed line 8122 and a metering pump 8123 to be further filtered in a second retentate vessel 8200. In some embodiments, the large diameter synthetic membrane vesicles suspension exiting the first retentate vessel 8100 can be concentrated by a factor of 1.33 (large diameter synthetic membrane vesicles concentration is increased by 33%). In a typical embodiment, the large diameter synthetic membrane vesicles are multivesicular liposomes.

In some embodiments, similar filtration can occur in the second retentate vessel 8200 as described above for the first retentate vessel 8100. In some embodiments, the large diameter synthetic membrane vesicles suspension can enter the second retentate vessel 8200 at a rate of 0.75 L per 1 L added to the first retentate vessel 8100. In some embodiments, a solution can be fed into the second retentate vessel 8200 through a line 8132, the solution first passing through a manual valve 8204 and a sterilizing hydrophilic filter 8172, at a rate of 2 L per 0.75 L concentrated large diameter synthetic membrane vesicles suspension added to the second retentate vessel 8200. In some embodiments, a portion of the large diameter synthetic membrane vesicles suspension in the second retentate vessel 8200 can be pumped by pump 8112 through a cross-flow (tangential-flow) filtration module 8152. In some embodiments, the permeate can be drawn off through a permeate line 8162 (passing through a sterilizing hydrophilic filter 8192 and a manual valve 8206), wherein for each 0.75 L of large diameter synthetic membrane vesicles suspension added to the second retentate vessel 8200, 2.25 L of permeate can be removed and discarded. In some embodiments, the retentate from the filtration module 8152 can be circulated back into the second retentate vessel 8200 via a retentate line 8142. In some embodiments, for each 0.75 L of large diameter synthetic membrane vesicles suspension added to the second retentate vessel 8200, a 0.50 L flow of the concentrated large diameter synthetic membrane vesicles suspension can be removed from the second retentate vessel 8200 through a feed line 8124 and a metering pump 8125 to be further filtered in a final retentate vessel 8300. In some embodiments, the large diameter synthetic membrane vesicles suspension exiting the second retentate vessel 8200 can now be concentrated 200%, whereas the buffer solution concentration in the large diameter synthetic membrane vesicles suspension can be roughly 9.1% with respect to the large diameter synthetic membrane vesicles suspension in the inlet line 8120.

In some embodiments, similar filtration can occur in the final retentate vessel 8300 as described above for the first retentate vessel 8100 and second retentate vessel 8200. In some embodiments, the concentrated large diameter synthetic membrane vesicles suspension traveling through the feed line 8124 can enter the final product vessel 8300 where it is further filtered and concentrated to contain all the large diameter synthetic membrane vesicles entering through the inlet line 8120, in the final product vessel 8300. In some embodiments, a solution can be fed into the final retentate vessel 8300 through a line 8132, the solution first passing through a manual valve 8208 and a sterilizing hydrophilic filter 8174, at a rate of 1.75 L per 0.50 L concentrated large diameter synthetic membrane vesicles suspension added to the final retentate vessel 8300. In some embodiments, the large diameter synthetic membrane vesicles suspension can be pumped through the pump 8114 to the cross-flow filtration module 8154, wherein the permeate can be drawn off to be discarded through a permeate line 8164 (passing through a sterilizing hydrophilic filter 8194 and a manual valve 8210) at a rate of 2.25 L per 0.5 L of large diameter synthetic membrane vesicles suspension fed to the final product vessel 8300. In some embodiments, in the final product vessel 8300, the large diameter synthetic membrane vesicles suspension can contain a buffer concentration. In some embodiments, the buffer concentration can be as low as 2%.

Filters 8170, 8190, 8172, 8192, 8174, and 8194 are sterilizing hydrophilic filters. Filters 8180, 8182, and 8184 are sterilizing hydrophobic gas vent filters used in the retentate vessels and fed by gas lines 8131, 8133, and 8135, respectively. In some embodiments, the systems depicted in FIG. 1A through FIG. 8 can be operated in a sterile (aseptic) fashion). For example, the addition of appropriate steam lines, condensate drain lines and valves, can allow the system to be sterilized. In some embodiments, all inputs and outputs are equipped with sterile barrier filters. In a typical embodiment, the large diameter synthetic membrane vesicles are multivesicular liposomes.

In some embodiments, a continuous-flow particle concentration system can be configured where a set of cascading particle suspension concentrators can be in series together adapted to remove and/or replace the suspending medium of a particle suspension in a continuous fashion. In some embodiments, the cascading particle suspension concentrators can be cross flow filters (FIG. 8, components 8150, 8152, 8154) and the suspending medium can be replaced by diafiltration. In some embodiments, the cascading particle suspension concentrators can be hydro-cyclones or disk centrifuge units.

FIG. 9

Figure 9A:
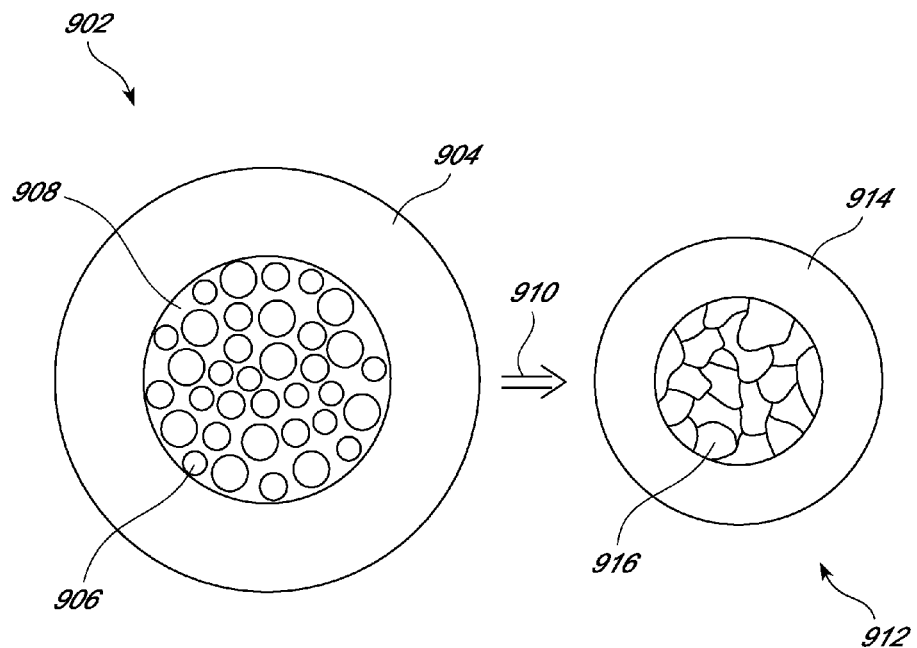
FIG. 9A and FIG. 9B provide cross-sectional views of a droplet, a more detailed view of a droplet, and a large diameter synthetic membrane vesicle particle. In some embodiments, the large diameter synthetic membrane vesicle particle can be a MVL particle. The large diameter synthetic membrane vesicle particle can be formed by removal of the organic solvent from the emulsion droplet.

FIG. 9A provides cross-sectional views of an atomized droplet 902, and a large diameter synthetic membrane vesicles particle 912. In a typical embodiment, the large diameter synthetic membrane vesicles particle 912 can be formed by removal of an organic solvent from the atomized droplet 902. In a typical embodiment, the atomized droplet 902 can comprise a first component core and a buffer solution shell 904. In some embodiments, first component core can comprise a continuous phase 908 and a suspension of droplets 906 in the continuous phase 908. In some embodiments, the droplets 906 can be aqueous phase droplets and can be surrounded by a continuous phase 908 that can be an organic solvent. In some embodiments, the aqueous phase droplets can be from about 10 nm to about 10µ in diameter. In some embodiments, the aqueous phase droplets can be from about 500 nm to about 5µ in diameter. In a typical embodiment, the aqueous phase droplets can be from about 100 nm to about 2µ in diameter. For example the average diameter of the aqueous phase droplets can be about 1µ in diameter. In some embodiments, the organic solvent can then be removed in the solvent removal chamber to provide droplets of large diameter synthetic membrane vesicles 912 within a shell of dextrose/lysine 914. In a typical embodiment, the large diameter synthetic membrane vesicles droplet 912 are a multivesicular liposomes droplet. Multivesicular liposomes (MVL) are uniquely different from other lipid-based drug delivery systems. Topologically, MVL are defined as liposomes containing multiple non-concentric chambers 916 within each droplet 912, resembling a "foam-like" matrix. The chambers 916 of the MVL can have the same volume as the first component particles, (e.g. 1µ) as shown in FIG. 9A. The presence of internal membranes distributed as a network throughout the MVL may serve to confer increased mechanical strength to the vesicle, while still maintaining a high volume:lipid ratio. Thus, both structurally and functionally the MVL are unusual, novel and distinct from all other types of liposomes.

Figure 9B:
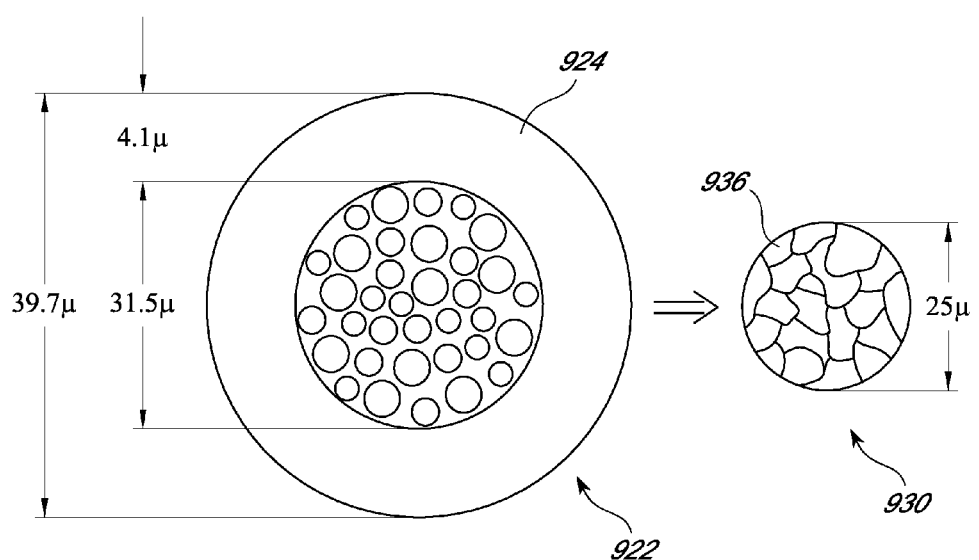

In one embodiment, a large diameter synthetic membrane vesicles droplet 930 made by the instant processes can be, as depicted in FIG. 9B, for example, an atomized droplet 922 containing equal volumes of dextrose/lysine 924 and first component, where the diameter of the atomized droplet is approximately 39.7 µm. In a typical embodiment, the large diameter synthetic membrane vesicles droplet 930 can be a multivesicular liposomes droplet. In this embodiment, the first component core then is approximately 31.5 µm and the dextrose/lysine shell 924 can be approximately 4.1 µm thick. When the organic solvent is removed from this atomized droplet 922, the resultant MVL 930 is 25 µm in diameter (the dextrose/lysine shell 924 is omitted for clarity). In some embodiments, chambers 936 of the MVL 930 can have the same volume as the suspension of droplets in the continuous phase of the first component.

FIG. 10 is a schematic of one example of a continuous-flow diafiltration system 1010 comprising a continuous flow centrifuge. The large diameter synthetic membrane vesicles suspension can be pumped from a solvent removal vessel to the continuous-flow diafiltration system 1010.

In some embodiments, the continuous-flow diafiltration system 1010 can include a solvent removal vessel as depicted in FIG. 7 and as in component 70 of FIG. 1A and FIG. 1B. The large diameter synthetic membrane vesicles suspension can travel to the diafiltration system 1010 through a particle suspension inlet line 10120 (also seen in FIG. 7, component 7270), reaching a first retentate vessel 10100. In some embodiments, for each 1 L of large diameter synthetic membrane vesicles suspension fed to the first retentate vessel 10100, a 2 L solution can be fed into the first retentate vessel 10100 through a line 10130, the solution first passing through a manual valve 10600 and a sterilizing hydrophilic filter 10170. In some embodiments, the large diameter synthetic membrane vesicles are multivesicular liposomes and the solution is a saline solution.

In some embodiments, a portion of the large diameter synthetic membrane vesicles suspension in the first retentate vessel 10100 can be pumped by pump 10110 through a cross-flow (tangential-flow) filtration module 10150. For example, this can be a hollow fiber type module. In one embodiment, the hollow fiber filter used is Model No. CFP-2-E-10A (0.2 micron) manufactured by Amersham Biosciences of Westborough, Mass. In some embodiments, the pore size of the cross-flow (tangential-flow) filtration modules 10150, 10152 and 10154, can be chosen to retain the large diameter synthetic membrane vesicles while allowing the suspending medium to pass through the filter membranes as permeate. The pumps used in the diafiltration system can be of various types, such as peristaltic or rotary lobe positive displacement pumps. In some embodiments, cross-flow recirculation pumps 10110, 10112 and 10114 operate with at least twice the permeate flow rate of their associated cross-flow filter module and preferably 3 times, 5 times or 10 times the permeate flow rates. In some embodiments, the permeate can be drawn off through a permeate line 10160 (passing through a sterilizing hydrophilic filter 10190 and a manual valve 10602), wherein for each 1 L of large diameter synthetic membrane vesicles suspension added to the first retentate vessel 10100, 2.25 L of permeate can be removed and discarded. In some embodiments, the retentate from the filtration module 10150 can be circulated back into the first retentate vessel 10100 via a retentate line 10140. In some embodiments, for each 1 L of large diameter synthetic membrane vesicles suspension added to the first retentate vessel 10100, a 0.75 L flow of the concentrated large diameter synthetic membrane vesicles suspension can be removed from the first retentate vessel 10100 through a feed line 10122 and a metering pump 10123 to be further filtered in a second retentate vessel 10200. In some embodiments, the large diameter synthetic membrane vesicles suspension exiting the first retentate vessel 10100 can be concentrated by a factor of 1.33 (large diameter synthetic membrane vesicles concentration is increased by 33%). In a typical embodiment, the large diameter synthetic membrane vesicles are multivesicular liposomes.

In some embodiments, similar filtration can occur in the second retentate vessel 10200 as described above for the first retentate vessel 10100. In some embodiments, the large diameter synthetic membrane vesicles suspension can enter the second retentate vessel 10200 at a rate of 0.75 L per 1 L added to the first retentate vessel 10100. In some embodiments, a solution can be fed into the second retentate vessel 10200 through a line 10132, the solution first passing through a manual valve 10204 and a sterilizing hydrophilic filter 10172, at a rate of 2 L per 0.75 L concentrated large diameter synthetic membrane vesicles suspension added to the second retentate vessel 10200. In some embodiments, a portion of the large diameter synthetic membrane vesicles suspension in the second retentate vessel 10200 can be pumped by pump 10112 through a cross-flow (tangential-flow) filtration module 10152. In some embodiments, the permeate can be drawn off through a permeate line 10162 (passing through a sterilizing hydrophilic filter 10192 and a manual valve 10606), wherein for each 0.75 L of large diameter synthetic membrane vesicles suspension added to the second retentate vessel 10200, 2.25 L of permeate can be removed and discarded. In some embodiments, the retentate from the filtration module 10152 can be circulated back into the second retentate vessel 10200 via a retentate line 10142. In some embodiments, for each 0.75 L of large diameter synthetic membrane vesicles suspension added to the second retentate vessel 10200, a 0.50 L flow of the concentrated large diameter synthetic membrane vesicles suspension can be removed from the second retentate vessel 10200 through a feed line 10124 and a metering pump 10125 to be further filtered in a third retentate vessel 10300. In some embodiments, the large diameter synthetic membrane vesicles suspension exiting the second retentate vessel 10200 can now be concentrated 200%, whereas the buffer solution concentration in the large diameter synthetic membrane vesicles suspension is roughly 9.1% with respect to the large diameter synthetic membrane vesicles suspension in the inlet line 10120.

In some embodiments, similar filtration can occur in the third retentate vessel 10300 as described above for the first retentate vessel 10100 and second retentate vessel 10200. In some embodiments, the concentrated large diameter synthetic membrane vesicles suspension traveling through the feed line 10124 can enter the third product vessel 10300 where it is further filtered and concentrated to contain all the large diameter synthetic membrane vesicles entering through the inlet line 10120, in the third product vessel 10300. In some embodiments, a solution can be fed into the third retentate vessel 10300 through a line 10132, the solution first passing through a manual valve 102010 and a sterilizing hydrophilic filter 10174, at a rate of 1.75 L per 0.50 L concentrated large diameter synthetic membrane vesicles suspension added to the third retentate vessel 10300. In some embodiments, the large diameter synthetic membrane vesicles suspension can be pumped through the pump 10114 to the cross-flow filtration module 10154, wherein the permeate can be drawn off to be discarded through a permeate line 10164 (passing through a sterilizing hydrophilic filter 10194 and a manual valve 10610) at a rate of 2.25 L per 0.5 L of large diameter synthetic membrane vesicles suspension fed to the third product vessel 10300. In some embodiments, in the third product vessel 10300, the large diameter synthetic membrane vesicles suspension can contain a buffer concentration. In some embodiments, the buffer concentration can be as low as 2%.

In some embodiments, the large diameter synthetic membrane vesicles suspension traveling through a feed line 10126, can be metered by a pump 10127 and can enter a continuous flow centrifuge module 10400 wherein the supernantant can be pumped to be discarded through a pump 10116 through a permeate line 10166 (passing through a sterilizing hydrophilic filter 10196). In a typical embodiment, the large diameter synthetic membrane vesicles are multivesicular liposomes.

In some embodiments, the large diameter synthetic membrane vesicles suspension traveling through a feed line 10128, can be metered by a pump 10129 and can enter a final retentate vessel 10500. In a typical embodiment, the large diameter synthetic membrane vesicles are multivesicular liposomes.

Filters 10170, 10190, 10172, 10192, 10174, 10194, and 10196 are sterilizing hydrophilic filters. Filters 10180, 10182, 10184 and 10186 are sterilizing hydrophobic gas vent filters used in the retentate vessels and fed by gas lines 10131, 10133, 10135 and 10137, respectively.

FIG. 11 is a schematic of one example of a continuous-flow centrifuge system 1110 comprising a plurality of continuous flow centrifuges. The large diameter synthetic membrane vesicles suspension can be pumped from a solvent removal vessel to the continuous-flow centrifuge system 1110.

In some embodiments, the continuous-flow centrifuge system 1110 can include the solvent removal vessel as depicted in FIG. 7. The large diameter synthetic membrane vesicles suspension can travel to the centrifuge system 1110 through a particle suspension inlet line 11120 (also seen in FIG. 7, component 7270, and as represented by components 70 in FIG. 1a and FIG. 1B), reaching a first retentate vessel 11100. In some embodiments, a large diameter synthetic membrane vesicles suspension can be fed to the first retentate vessel 11100, and a solution can be fed into the first retentate vessel 11100 through a line 11130, the solution first passing through a manual valve 11600 and a sterilizing hydrophilic filter 11170. The large diameter synthetic membrane vesicles suspension in the first retentate vessel 11100 can be pumped by a pump 11220 to a first centrifuge module 11150. In some embodiments, the permeate can be drawn off from the first centrifuge 11150 through a permeate line 11160 (passing through a sterilizing hydrophilic filter 11190 being pumped by a pump 11110), and discarded. In some embodiments, large diameter synthetic membrane vesicles suspension can exit the first centrifuge module 11150 through a feed line 11122, metered by a pump 11123, to be further processed in a second retentate vessel 11200. In some embodiments, the large diameter synthetic membrane vesicles suspension flowing in feed line 11122 can be concentrated by at least 33%. In a typical embodiment, the large diameter synthetic membrane vesicles are multivesicular liposomes and the solution is a saline solution.

In some embodiments, the concentrated large diameter synthetic membrane vesicles suspension can enter the second retentate vessel 11200 for further processing, and a solution can be fed through a line 11132, the solution first passing through a manual valve 11604 and a sterilizing hydrophilic filter 11172. The large diameter synthetic membrane vesicles suspension from the second retentate vessel 11200 can be pumped by a pump 11240 to a second centrifuge module 11152. In some embodiments, the permeate can be drawn off from the second centrifuge 11152 through a permeate line 11162 (passing through a sterilizing hydrophilic filter 11192 being pumped by a pump 11120), and discarded. In some embodiments, large diameter synthetic membrane vesicles suspension can exit the second centrifuge module 11152 through a feed line 11124, metered by a pump 11125, to be further processed in a third retentate vessel 11300. In some embodiments, the large diameter synthetic membrane vesicles suspension flowing in feed line 11125 can be concentrated by at least 33%. In a typical embodiment, the large diameter synthetic membrane vesicles are multivesicular liposomes and the solution is a saline solution.

In some embodiments, the large diameter synthetic membrane vesicles suspension traveling through the feed line 11124, can be metered by a pump 11125 and can enter the third retentate vessel 11300 where it can be further processed. In some embodiments, a solution can be fed into the third retentate vessel 11300 through a line 11134, the solution first passing through a manual valve 11608 and a sterilizing hydrophilic filter 11174. In some embodiments, the large diameter synthetic membrane vesicles suspension can be pumped by a pump 11260 to a third centrifuge module 11154. In some embodiments, the permeate can be drawn off from the centrifuge through a permeate line 11164 (passing through a sterilizing hydrophilic filter 11194 being pumped by pump 11130), and discarded. In a typical embodiment, the large diameter synthetic membrane vesicles are multivesicular liposomes.

In some embodiments, the concentrated large diameter synthetic membrane vesicles suspension traveling through feed line 11166, can be metered by pump 11127 and can enter a final retentate vessel 11400. In a typical embodiment, the large diameter synthetic membrane vesicles are multivesicular liposomes.

Filters 11170, 11190, 11172, 11192, 11174, and 11194 are sterilizing hydrophilic filters. Filters 11180, 11182, 11184 and 11186 are sterilizing hydrophobic gas vent filters used in the retentate vessels and fed by gas lines 11131, 11133, 11135 and 11137, respectively. In a typical embodiment, the large diameter synthetic membrane vesicles are multivesicular liposomes.

The systems depicted in FIG. 1A through FIG. 11 can be operated in a sterile (aseptic) fashion. With the addition of appropriate steam lines, condensate drain lines and valves, the system can be sterilized. All inputs and outputs are equipped with sterile barrier filters.

In some embodiments, the large diameter synthetic membrane vesicles are multivesicular liposomes. In some embodiments, the multivesicular liposomes further comprise bupivaciane, DEPC, DPPG, and tricaprylin. In some embodiments, the multivesicular liposomes further comprise bupivacaine phosphate, DEPC, DPPG, and tricaprylin. In some embodiments, the multivesicular liposomes further comprise bupivacaine, DEPC, DPPG, tricaprylin and cholesterol. In some embodiments, the multivesicular liposomes further comprise bupivacaine phosphate, DEPC, DPPG, tricaprylin and cholesterol.

In some embodiments, the multivesicular liposomes further comprise bupivaciane, dextrose, L-Lysine, DEPC, DPPG, and tricaprylin. In some embodiments, the multivesicular liposomes further comprise bupivacaine phosphate, dextrose, L-Lysine, DEPC, DPPG, and tricaprylin. In some embodiments, the multivesicular liposomes further comprise bupivacaine, dextrose, L-Lysine, DEPC, DPPG, tricaprylin and cholesterol. In some embodiments, the multivesicular liposomes further comprise bupivacaine phosphate, dextrose, L-Lysine, DEPC, DPPG, tricaprylin and cholesterol.

In some embodiments, the multivesicular liposomes further comprise bupivaciane, dextrose, DEPC, DPPG, and tricaprylin. In some embodiments, the multivesicular liposomes further comprise bupivacaine phosphate, dextrose, DEPC, DPPG, and tricaprylin. In some embodiments, the multivesicular liposomes further comprise bupivacaine, dextrose, DEPC, DPPG, tricaprylin and cholesterol. In some embodiments, the multivesicular liposomes further comprise bupivacaine phosphate, dextrose, DEPC, DPPG, tricaprylin and cholesterol.

In some embodiments, the multivesicular liposomes further comprise bupivaciane, L-Lysine, DEPC, DPPG, and tricaprylin. In some embodiments, the multivesicular liposomes further comprise bupivacaine phosphate, L-Lysine, DEPC, DPPG, and tricaprylin. In some embodiments, the multivesicular liposomes further comprise bupivacaine, L-Lysine, DEPC, DPPG, tricaprylin and cholesterol. In some embodiments, the multivesicular liposomes further comprise bupivacaine phosphate, L-Lysine, DEPC, DPPG, tricaprylin and cholesterol.

In some embodiments, the multivesicular liposomes further comprise bupivacaine, morphine, cytarabine, or their pharmaceutically acceptable salts as the therapeutic agent. In some embodiments, the multivesicular liposomes further comprise bupivacaine phosphate, morphine sulfate, or cytarabine HCl.

In another embodiment, any one of the above described embodiments can be used alone or in combination with any one or more of the above described embodiments. For example, any above described atomizing nozzle, evaporation apparatus, continuous-flow emulsification system, continuous-flow diafiltration system, continuous-flow diafiltration further comprising one or more centrifuges, continuous-flow centrifuge system, or continuous processing system can be used alone or in combination. Thus, an evaporation apparatus can be used in conjunction with a three-fluid atomizing nozzle. This evaporation system/atomizing nozzle can be used with a continuous-flow emulsification system, as depicted in FIGS. 1A, 1B, and 1C. The three-fluid atomizing nozzle/evaporation apparatus combination can be used in conjunction with a continuous-flow system, as depicted in FIGS. 8, 10, and 11. Any of these combinations can be used to make multivesicular liposomes. In particular any of the combinations can be used to make multivesicular liposomes containing bupivacaine or its salts as the therapeutic agent.

The following examples are meant to further illustrate the embodiments, they are not meant to be limiting in any way.

EXAMPLE 1

The following is an example utilizing the process parameters and steps of the devices depicted in the Figures. The three fluids applied to the atomizing nozzle (FIG. 1A and FIG. 1B, component 75; FIG. 3A, component 310; FIG. 7, component 7510) as part of the process of forming multivesicular liposomes have the following compositions per liter.

The first fluid (FIG. 3A-3L, component 3115; FIG. 5, component 5115; FIG. 7, component 7115) was a first liquid made up of the first component, the first component having two components: an organic phase and a first aqueous phase which are emulsified with equal volumes. The organic phase was composed of 1,2-dierucoyl-sn-glycero-3-phosphocholine (17.78 g), 1,2-dipalmitoyl-sn-glycero-3-phosphoglycerol (1.056 g), cholesterol (10.34 g), tricaprylin (4.32 g), water (0.70 g) and methylene chloride (quantity sufficient to make 1 L total volume of the organic phase. The first aqueous phase was composed of 0.2 molar (200 mM) phosphoric acid and bupivacaine (40 g) and water (quantity sufficient to make 1 L total volume of the first aqueous phase).

The second fluid (FIG. 3A-3L, component 3120; FIG. 5, component 5120; FIG. 7, component 7120) was a second liquid made up of a second aqueous phase composed of L-lysine (monohydrate) (16.8 g), dextrose (13.25 g), and water (quantity sufficient to make 1 L total volume of the second fluid.

The third fluid (FIG. 3A-3L, component 3140; FIG. 5, component 5140; FIG. 7, component 7140) was nitrogen gas containing water vapor (100% relative humidity at 42° C. and 25 psig).

Preparation of Solvent Evaporation Chamber

Nitrogen was supplied to the solvent removal vessel (FIG. 1A AND FIG. 1B, component 50; FIG. 7 component 710) through two solvent removal vessel gas inlet lines: FIG. 1A components 115 and 110; FIG. 7 components 7280 and 7430) the main carrier gas inlet line (component 115 of FIG. 1A AND FIG. 1B; component 7280 of FIG. 7), or main rotation jet, was tangential to vessel wall and approximately 40% up from vessel bottom, causing clockwise rotation viewed from above; and the lid protection gas inlet (component 110 of FIG. 1A AND FIG. 1B; component 7430 of FIG. 7), or lid protection jet, at the corner of 11d (component 7220 of FIG. 7) and vessel wall (component 7350 of FIG. 7), tangential to the wall and moving in the same rotational direction (component 7240 of FIG. 7). The nitrogen entering these inlet lines was humidified to 100% relative humidity at 42° C. and at 25 psig (pounds per square inch gauge). The main rotation jet supplies 335 L/min at 42° C. of humidified nitrogen while the lid protection jet flow was 25 L/min at 42° C. of humidified nitrogen (the lid protection jet keeps deposit buildup off the lid). The nitrogen was humidified prior to entering the solvent removal vessel by passing it through a heated tube-in-shell heat exchanger (component 90, FIG. 1A AND FIG. 1B) that was coated with water (humidification water) followed by an excess-liquid water removal chamber (component 45, FIG. 1A AND FIG. 1B) and liquid bleed. The nitrogen was humidified to reduce evaporation of water from the spray which raised the osmolality of the suspending buffer.

In this example, the solvent removal vessel had a volume of approximately 138 liters, the inside diameter was 56 cm, the walls were 52 cm high and the dome at the bottom was 10 cm deep. Thus the inside height of the solvent removal vessel was 62 cm from the lid to the bottom of the domed bottom. The gas outlet tube (component 80, FIG. 1A AND FIG. 1B; component 7340, FIG. 7) (including the conical fitting FIG. 7, component 300 and vortex stabilizer FIG. 7, component 7360) extends 42.5 cm into the solvent removal vessel down from lid. The diameter of the gas outlet tube was 2.3 cm (inside diameter) and the conical fitting tapers 20 degrees to a 1.5 cm inside diameter for the gas outlet orifice (FIG. 7, component 7310). The vortex stabilizer attached to the end of the conical fitting had a diameter of 2.5 cm. The main rotation (carrier) gas inlet was tangential to the wall and 37 cm down from the lid and had an inside diameter of 1.9 cm.

The three-fluid atomizing nozzle (FIG. 1A and FIG. 1B, component 75; FIG. 3A, component 310; FIG. 7, component 7510), the rinse nozzle (FIG. 1A AND FIG. 1B, component 105; FIG. 7, component 7400), and lid protection gas inlet (FIG. 1A, component 110; FIG. 7, component 7340) all extend through the lid of the solvent removal vessel (FIG. 1A AND FIG. 1B, component 50; FIG. 7 component 710) and were each centered 10.2 cm from the vessel wall (FIG. 7, component 7350). The lid protection gas inlet (FIG. 7, component 7430) had an inside diameter of 0.95 cm, extends through the lid of the vessel (FIG. 7, component 7220), and faced parallel to the inside of the lid in a direction to give clockwise (viewed down from above) rotation of the gas. Starting with the three-fluid atomizing nozzle (FIG. 1A and FIG. 1B, component 75; FIG. 3A, component 310; FIG. 7, component 7510) as zero degrees, the main carrier gas inlet line was located 52 degrees clockwise, the rinse nozzle was 90 degrees clockwise, and the lid protection gas inlet was 135 degrees clockwise with its outlet approximately 180 degrees clockwise.

The sides (FIG. 7, component 7350) and bottom (FIG. 7, component 7250) of the solvent removal vessel were jacketed at 24.1° C. by connection to a circulating bath. The temperature in the jacket was adjusted to approximately match the steady state gas exit temperature. Such a match prevented evaporation and drying of the multivesicular liposomes on the wall or condensation of water that could rupture, through osmotic shock, the multivesicular liposomes that are being formed in the vessel.

Preparation of a First Component

The recirculation loop (FIG. 2, component 2125) connected to the high-shear mixer (FIG. 1A AND FIG. 1B, component 25, FIG. 2, component 2130) (Ross model HSM-703XS-20 Sanitary Inline High Shear Mixer equipped with a 3" diameter X-5 Series rotor/stator for operation to 14,400 rpm. (11,300 feet/min. tip speed) with gap ring #3) was primed with methylene chloride to ensure that all air was removed from the high-shear mixer. The jacket of the heat exchanger (FIG. 1A AND FIG. 1B, component 30; FIG. 2 component 2170) was supplied with 5° C. coolant (water+50% ethylene glycol) (FIG. 1A, components 96 and 97; FIG. 2, components 2110 and 2105). The mixer seal lubricant tank (FIG. 1A AND FIG. 1B, component 10), filled with water, was also cooled with 5° C. coolant (water+50% ethylene glycol). The mixer was started at a setting of 30 Hz (approx. 7,200 rpm) causing a flow around the mixer loop estimated at 21,000 mL/min and with an internal volume of 280 mL. Thus, fluid in the loop went through the mixer blades and heat exchanger an average of every 0.8 seconds.

After the high shear mixer was primed with methylene chloride, the organic phase and first aqueous phase peristaltic pumps (components 12 and 2, respectively, of FIG. 1A AND FIG. 1B) were concurrently started. The organic phase was pumped at 33 mL/min and the first aqueous phase was also pumped at 33 mL/min. The organic phase and first aqueous phase entered the high-shear mixer starting the formation of the first component. As the first component circulated around the high shear mixer recirculation loop, a small fraction of the flow was forced through the first component exit line (FIG. 2, component 2180; FIG. 5, component 5114) to the three-fluid atomizing nozzle (FIG. 1A AND FIG. 1B, component 75; FIG. 3A-3L, component 310; FIG. 5, component 505; FIG. 7, component 7510) at 66 mL/min (total of the two flow rates). Consequently, the priming methylene chloride was soon flushed from the mixer loop by this flow (4.2 min per loop volume of flush).

Concurrent with the starting of the organic phase and first aqueous phase peristaltic pumps, the second aqueous phase (connected to the three-fluid atomizing nozzle) and wall rinse (to the rinse nozzle (FIG. 1A and FIG. 1B, component 105; FIG. 7, component 7400)) peristaltic pumps (components 22 and 64, respectively, of FIG. 1A and FIG. 1B) were started and pumped their respective components at 66 mL/min each. The wall rinse solution was 33.5 g of dextrose per liter of water. Nitrogen at 60 psig (room temperature, not humidified) was supplied to these two nozzles (FIG. 1A and FIG. 1B, components 75 and 105; FIG. 7, components 7510 and 7400). The second aqueous phase flowed through the three fluid nozzle at 66 mL/min. The three-fluid atomizing nozzle had a nitrogen flow rate of 51 L/min@1 atm and the wall rinse nozzle (manufactured by GEA Process Engineering of Columbia, Md.) had a flow rate of 66 L/min@1 atm.

After exiting the three-fluid atomizing nozzle, the formed atomized emulsion droplets came into contact with the carrier gas (nitrogen) in the solvent removal chamber (FIG. 7, component 7230) of the solvent removal vessel (FIG. 1A and FIG. 1B, component 50; (FIG. 7, component 710). The carrier gas rotated inside the chamber (FIG. 7, component 7240) as a small, rapidly rotating, intense gas vortex (FIG. 7, component 7245) formed at the exit orifice (FIG. 7, component 7310). This allowed the droplets to contact the gas for an extended period of time in order to effectuate methylene chloride evaporation and removal. After removal of the methylene chloride, the formed multivesicular liposome suspension droplets (FIG. 7, component 7380) were collected as a suspension of multivesicular liposomes (FIG. 7, component 7390) at the bottom of an evaporation vessel (FIG. 1A and FIG. 1B, component 50; FIG. 7, component 7250). The multivesicular liposomes were collected in the solvent removal vessel and then drained out of the drain port (FIG. 1A and FIG. 1B, component 130; FIG. 7, component 7270) through a peristaltic positive displacement pump (FIG. 1A and FIG. 1B, component 125), set to pump slightly faster (approximately 200 mL/min) than the suspension drains out of the bottom (approximately 165 mL/min), therefore the exit stream of multivesicular liposome suspension were periodically interrupted by small segments of chamber gas. This pump rate prevented any appreciable venting of solvent vapors into the room and protects the multivesicular liposome suspension from exposure to high velocity gas streams or foaming.

At system equilibrium, the nitrogen exiting the solvent removal vessel through the gas outlet (FIG. 1A and FIG. 1B, component 80; FIG. 7, component 7310) was at a temperature of approximately 21.5° C. The solvent removal vessel jacket was cooled to approximately 24.1° C. The temperature of the first component (part of which travels to the three-fluid atomizing nozzle) leaving the heat-exchanger was 15.3° C. After traveling through heat exchanger, and while traveling back to the high-shear mixer through the recirculation line, the temperature of the first component was approximately 14.3° C.

At equilibrium the system then ran continuously making multivesicular liposomes for as long as the feed solutions and nitrogen were supplied. Five hundred mL samples of multivesicular liposome suspension were taken from the suspension outlet (FIG. 7, component 7260) in the solvent removal vessel and diafiltered (using a hollow fiber filter, Model No. CFP-2-E-8A from Amersham Biosciences of Westborough, Mass.) with four volumes of normal saline on a small scale batch diafiltration system (FIG. 1A and FIG. 1B, component 70). Optionally, settling of the multivesicular liposomes and excess liquid could be decanted to obtain the final multivesicular liposomes in a chosen aqueous solution at a chosen MVL concentration. Full continuous operation can be obtained by connecting the solvent removal vessel outlet pump to the apparatus of FIG. 8.

EXAMPLE 2

Preparation of First Component

The recirculation loop connected to the high-shear mixer (FIG. 1A and FIG. 1B, component 25; FIG. 2, component 2130) (Ross Model HSM-703XS-20 Sanitary Inline High Shear Mixer equipped with a 3" diameter X-5 Series rotor/stator for operation to 14,400 rpm. (11,300 feet/min. tip speed) with gap ring #3) was primed with methylene chloride to ensure that all air was removed from the high-shear mixer. The jacket of the heat exchanger (FIG. 1A and FIG. 1B, component 30; FIG. 2, component 2170) was supplied with 5° C. coolant (water+50% ethylene glycol). The mixer seal lubricant tank, filled with water, was also cooled with 5° C. coolant (water+50% ethylene glycol). The high-shear mixer was started at a setting of 25 Hz (6,000 rpm), 30 Hz approx. (7,200 rpm) or 35 Hz (8,400 rpm).

After the high shear mixer was primed with methylene chloride, the organic phase and first aqueous phase peristaltic pumps (FIG. 1A and FIG. 1B, components 12 and 2, respectively) were concurrently started. The organic phase was pumped at 33 mL/min and the first aqueous phase was also pumped at 33 mL/min. Entry of the organic phase and first aqueous phase begin formation of the first component. As the first component circulates around the high shear mixer recirculation loop (FIG. 2, component 2125), a small fraction of the flow was forced through the first component exit line (FIG. 2, component 2180) to the three-fluid atomizing nozzle (FIG. 1A and FIG. 1B, component 75; FIG. 3A; FIG. 4A; FIG. 7 7510) at 66 mL/min (total of the two flow rates), the temperature of the emulsion being forced through the first component exit line (FIG. 2, component 2180) was from 16.5 to 21.1° C. The flow of the organic phase and first aqueous rapidly flushed the priming methylene chloride from the mixer loop (4.2 min per loop volume of flush).

TABLE 1

| Organic Phase Components (per 2 L Total Volume) | |
|---|---|
| cholesterol (Nippon) | 20.8 g |
| DEPC (Nippon) | 36.0 g |
| DPPG (Lipoid) | 1.89 g |
| tricaprylin (NOF) | 8.81 g |
| Water for injection | 0.49 mL |
| Methylene chloride (EMD) | 2,569 g |

The components of the organic phase are shown in Table 1.

TABLE 2

| First Aqueous Phase Components (per 2 L Total Volume) | |
|---|---|
| Bupivacaine (BASF) | 80 g |
| 0.20M $H_3PO_4$ (2 L, Mallinckrodt) | 200 mM |

The components of the first aqueous phase are shown in Table 2.

TABLE 3

Particle Sizing of Diluted Emulsion Samples by laser light scatter analysis.

| Batch | PSD (μm)(volume based) | | | |
|---|---|---|---|---|
| | $d_{10}$ | $d_{50}$ | $d_{90}$ | Span |
| Ross 30 Hz | 0.5 | 0.9 | 1.4 | 1.0 |
| Ross 35 Hz | 0.5 | 0.8 | 1.3 | 1.0 |
| Ross 25 Hz | 0.6 | 1.1 | 1.7 | 1.0 |
| Batch Lot D | 0.855 | 1.151 | 1.506 | 0.566 |
| Batch Lot E | 0.720 | 1.110 | 1.530 | 0.730 |

The emulsion samples were diluted and analyzed using a light scattering device (Horiba Instruments La-910) and the results are shown in Table 1.

The second aqueous phase (connected to the three-fluid atomizing nozzle) and wall rinse (to the rinse nozzle (FIG. 1A and FIG. 1B, component 105; FIG. 7, component 7400)) peristaltic pumps (components 22 and 64, respectively, of FIG. 1A and FIG. 1B) were started when the organic phase and first aqueous phase peristaltic pumps were started. The wall rinse solution having 33.5 g of dextrose per liter of water was introduced to the evaporation chamber at a flow rate of 66 mL/min. Nitrogen at 60 psig (room temperature, not humidified) was supplied to the atomizing nozzle. The second aqueous phase was introduced to the three fluid nozzle at a flow rate of 66 mL/min. The three-fluid atomizing nozzle has a nitrogen flow rate of 51 L/min @ 1 atm and the wall rinse nozzle (manufactured by GEA Process Engineering of Columbia, Md.) has a flow rate of 66 L/min @ 1 atm. The emulsion, second aqueous phase and nitrogen gas were combined using the three fluid nozzle to afford atomized droplets (FIG. 3, component 3155; FIG. 7, component 7155) which traveled in the evaporation chamber until the majority of the methylene chloride was removed from the atomized droplets. Removal of the methylene chloride produced multivesicular liposomes (FIG. 7, component 7380) which form a suspension (FIG. 7, component 7390) at the bottom of the evaporation chamber (FIG. 7, component 7250).

TABLE 4

| Second Aqueous Phase Components (per 5 L Total Volume) | |
|---|---|
| L-Lysine monohydrate | 84 g |
| 50% Dextrose soln (B Braun) | 132.5 mL |
| Deionized water (to final volume) | 5 L |

The Components of the Second Aqueous Phase are Shown in Table 4.

After system equilibrated (10 minutes), 500 mL samples of multivesicular liposomes suspension were collected. The Ross RPM was then changed and allowed to equilibrate for 10 minutes before collecting the next 500 mL sample. This was repeated for the last RPM. Each 500 mL batch was diafiltered in a batch mode (using a hollow fiber filter, Model No. CFP-6-D-9A from Amersham Biosciences of Westborough, Mass.), for four volumes with normal saline on a small scale batch diafiltration system (FIG. 1, component 70). The recirculation pump was set to 5,700 ml/min, while saline addition pump was set to 410 mL/min. The permeate valve was adjusted to keep the liquid volume in the diafiltration system constant at 1,000 and thus was also 410 mL/min, since the minimum working volume of this system was approximately 550 mL. In the present example, the processed multivesicular liposomes suspension was allowed to settle at 5° C. and then supernatant was decanted to achieve approximately 15 mg of bupivacaine per mL in the final multivesicular liposomes suspension.

TABLE 5

| Wall Rinse Solution (per 5 L Total Volume) | |
|---|---|
| 50% Dextrose soln (B Braun) | 335 mL |
| Deionized water (to final volume) | 5 L |

As can be seen in FIG. 12, controlled release of bupivacaine from MVL particles was examined in vitro at 37° C. in 0.5% ovine serum albumin dissolved in 50 mM phosphate buffered saline (pH7) showing a similar release of bupivacaine to that in Batch Lot A and B made by the process disclosed in patent WO 99/25319.

As can be seen in FIG. 13, the PK profile in rats of the continuous process samples shows a similar sustained release profile of bupivacaine to that in Batch Lot C made by the batch process disclosed in patent WO 99/25319.

TABLE 6

A

| Batch | Final Material Properties: Total Bupi[i] (mg/mL) | % PPV[ii] | Free Bupi[i] (mg/mL) | % Free | PSD[iii] (μm) d10 | d50 | d90 | pH Int | Ext |
|---|---|---|---|---|---|---|---|---|---|
| 30 Hz Batch | 14.9 | 41 | 0.79 | 3.2 | 18.0 | 44.7 | 102.8 | 5.7 | 7.0 |
| 35 Hz Batch | 13.5 | 38 | 0.81 | 3.7 | 14.2 | 36.3 | 83.2 | 6.0 | 7.3 |
| 25 Hz Batch | 12.8 | 38 | 0.83 | 4.0 | 14.8 | 32.4 | 69.4 | 5.9 | 7.4 |

B

| Batch | Final Material Properties Total Lipids: Chol[iv] | DEPC[v] | DPPG[vi] | TC[vii] |
|---|---|---|---|---|
| 30 Hz Batch | 3.24 | 5.98 | 0.23 | 1.50 |
| 35 Hz Batch | 3.70 | 6.72 | 0.31 | 1.61 |
| 25 Hz Batch | 3.30 | 6.15 | 0.22 | 1.51 |

[i]bupivacaine;
[ii]packed particle volume;
[iii]particle size distribution by mass;
[iv]cholesterol;
[v]1,2-dierucoyl-sn-glycero-3-phosphocholine;
[vi]1,2-dipalmitoyl-sn-glycero-3-phosphoglycerol;
[vii]tricaprylin

EXAMPLE 3

Heat Treatment of MVL Suspension

The system of FIG. 1B was used with the humidified rotation gas (N2) supplied by combination electric heater and tube-in shell heat exchanger as described for FIG. 1A, component 90. The system was equilibrated for 10 minutes and a 1,000 ml sample of MVL suspension, exiting the drain port (FIG. 1B, component 130) of the solvent removal vessel 50, was collected. The MVL sample was divided into two samples of 500 mL each. The first 500 mL MVL sample was heat treated as follows. The heat treatment was performed by rapidly adding 750 mL of 100° C. dextrose solution to the first sample to raise the mixture temperature up to approximately 63° C. After 30 seconds, 1,750 mL of +5° C. saline was rapidly added to lower the temperature of the mixture to near room temperature (35° C. or below). The sample volume was now 3,000 mL. The second 500 mL multivesicular liposomes sample was not heat treated. The second sample was diluted with the same volumes of dextrose solution (750 mL) and saline (1,750 mL) as the first sample but the solutions were at room temperature.

Each sample was diafiltered batch wise, with 4 volumes of saline. These 3,000 ml samples were each concentrated to 1 liter and then diafiltered in a batch mode (using a hollow fiber filter, Model No. CFP-6-D-9A from Amersham Biosciences of Westborough, Mass.), for four volumes with normal saline on a small scale batch diafiltration system (FIG. 1B, component 70). The recirculation pump (FIG. 8, component 8110, 8112, and 8114) was set to 5,700 mL/min, while saline addition pump (FIG. 8, component 8170, 8172, and 8174) was set to 410 mL/min. The permeate valve (FIG. 8, component 8202, 8206, and 8210) was adjusted to 410 mL/min to keep the liquid volume in the system constant at 1,000 mL. Since the minimum working volume of this system was approximately 550 ml, which was too large to allow these small samples to be concentrated to the target bupivacaine concentration of 15 mg/mL, they were allowed to settle at +5° C. and the supernatant was decanted to achieve approximately 15 mg of bupivacaine per ml in the final MVL suspensions.

The analytical results for the samples were as follows:

TABLE 7

|  | $d_{10}$ | $d_{50}$ | $d_{90}$ | ppv | bupi/ml |
|---|---|---|---|---|---|
| Not heat treated | 14.9 | 52.8 | 107.7 | 56% | 16.84 |
| Heat treated | 18.2 | 51.3 | 95.9 | 55% | 18 |

TABLE 8

| Sample | Chol | DEPC | DPPG | Tricap |
|---|---|---|---|---|
|  | | Total mg/ml | | |
| Not heat treated | 4.97 | 8.50 | 0.39 | 2.11 |
| Heat treated | 7.07 | 12.35 | 0.58 | 3.00 |

As can be seen in the Tables 7 and 8 above, the heat treatment did not significantly effect the particle size distribution of the MVLs and had only small effects on the bupivacaine (active agent) content and lipid composition of the particles.

Figure 14:
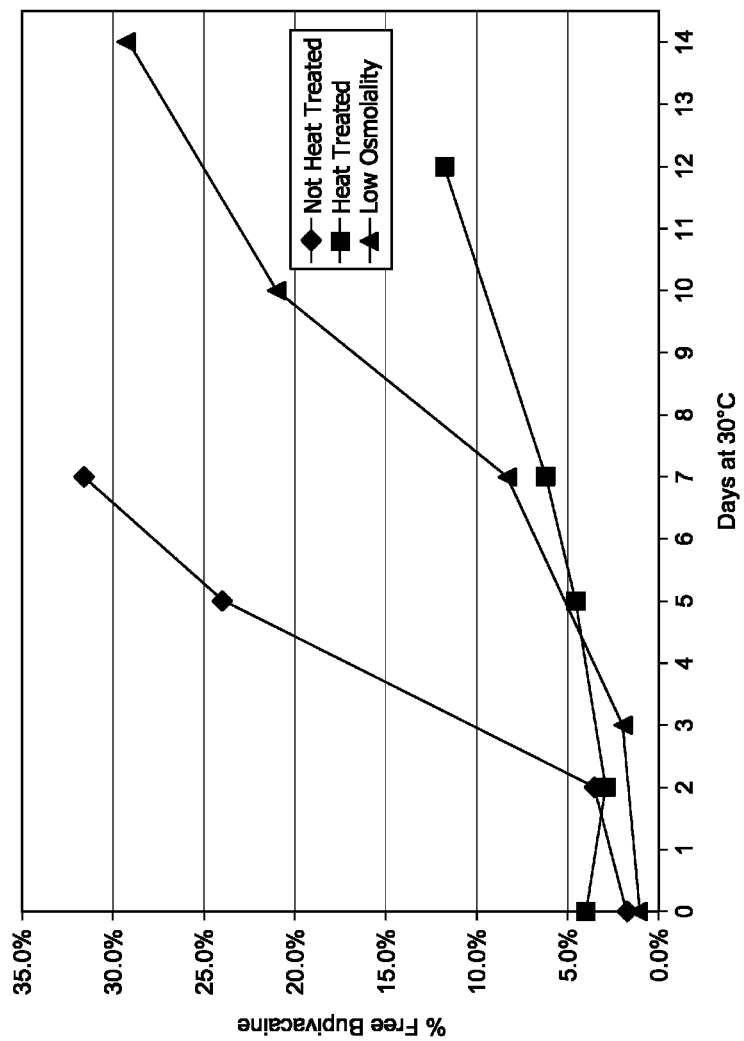
FIG. 14 is a graph of an accelerated stability profile study of a multivesicular formulation made with the instant manufacturing system with and without heat treatment. The low osmolality is more stable than the sample without heat treatment and the heat treated sample is most stable.

The heat treatment did have a surprising effect on the accelerated stability (30° C. stability) of these MVL suspensions, as can be seen in FIG. 14. Accelerated stability at 30° C. was greatly improved with heat treatment. A lower slope means less bupivacaine release and longer stability. Both samples were usable products when stored at +5° C. but the heat treated sample was projected to have a much longer shelf life.

As can be seen in FIG. 15, The PK profile in rats (measured substantially as per patent number WO 02/096368) also shows an improvement with heat treatment. Both samples have acceptable PK profiles. The heat treated sample gives longer lasting sustained release with higher serum values at 48 and 72 hours. The not heat treated sample was essentially zero at 72 hours. The heat treatment surprisingly improved the accelerated stability of the MVLs and also improved their in-vivo release profile.

EXAMPLE 4

Effect of Lowered 1st Aqueous Osmolality

The osmolality of the 1st aqueous solution in the previous examples was significantly above 300 mOsm/kg. If there was no appreciable loss of bupivacaine or phosphoric acid or water transport across the forming phospholipid membranes during the MVL production process, the internal chambers of the resultant MVLs will be filled with an aqueous solution with an osmolality at or near that of the final saline (300 mOsm/kg) storage suspending medium. If, on the other hand, the osmolality of the 1st aqueous and resultant MVLs was lower than that of saline, the MVLs will shrink slightly as the saline draws water out of the internal chambers. This will compress the phospholipids making up the MVL membranes and make them more stable and less bupivacaine permeable.

Both the lipid-solvent (LC) and the bupivacaine-acid (1st aqueous) were made up at ½ the concentration of normal (see below for formulations). This gave a 1st aqueous solution with an osmolality of 189 mOsm/kg which was expected to cause the MVLs to shrink and compress their membranes when diafiltered into normal saline of 300 mOsm/kg.

TABLE 9

| FIG. 2 #s | FIG. 1B #s | (but with no sterile filters) | |
|---|---|---|---|
| 2160 | 12 | LC, Solvent-lipids pump | 33 ml/min |
| 2120 | 2 | 1st aqueous, acid Bupi pump | 33 ml/min |
|  | 22 | Dextrose-lysine pump, 3 fluid noz | 66 ml/min |
|  | 64 | Dextrose only pump, wall rinse noz | 66 ml/min |
|  | 120 | Output rate out of spray chamber | 165 ml/min |
|  | 115 & 110 | Temperature of water humidified N2 feeding rotation jets | 44.6 C. |
|  | 90 | Temperature of N2 exiting electric heater 90 | 46 C. |
|  | 40 | Flow rate of humidification water into steam generator | 9 ml/min |
|  | 33 | Flow to both rotation jets (N2 before steam) | 400 L/min |
|  | 57 | Flow to top rotation jet | 15 L/min |
|  |  | Chamber Jacket supply temperature | 25 C. |
|  |  | Chamber exit temperature | 21.9 C. |
|  | 2150 & 2180 | heat exchanger emulsion inlet supplied to 3 fluid nozzle | 18.8 C. |
|  | 2175 | heat exchanger emulsion outlet | 17.2 C. |
|  | 2110 | Heat exchanger coolant supply | 4 C. |
|  | 11 | 3 Fluid nozzle N2 pressure | 60 psig |
|  | 21 | Wall rinse nozzle pressure | 60 psig |
|  | 13 | 3 fluid nozzle N2 flow | 54 L/min |
|  | 23 | Wall rinse nozzle N2 flow | 53 L/min |
|  | 25 | Ross Mixer always with gap ring #3 Run at resulting in this blade rotation rate | 30 Hz on VFD 7,200 RPM |
| 2160 | 10 | Solvent solution (LC), 4 liters | 4 liters |
|  |  | cholesterol (Nippon) | 20.8 g |
|  |  | DEPC (Nippon) | 36.0 g |
|  |  | DPPG (Lipoid) | 1.89 g |
|  |  | tricaprylin (NOF) | 8.81 g |
|  |  | WFI | 1.4 ml |
|  |  | MeCl (EMD) | 5,138 g |
| 2120 | 5 | 1st aqueous soln. Acid & Bupi, 2 liters (emulsified by Ross, fed to rotor center) | 2 liters |
|  |  | Dissolve Bupivacaine base (BASF) | 40 g |
|  |  | in 2 liters of 0.112M H3PO4 (Mallinckrodt) | 112 mM |
|  |  | Osmolality | 189 mOsm |
|  | 60 | Dextrose/lysine solution (fed to sheath of 3 fluid nozzle) | 5 liters |
|  |  | L-Lysine monohydrate | 84 g |
|  |  | 50% Dextrose soln (B Braun) | 105 g |
|  |  | DI water to final volume of | 5 L |
|  |  | Osmolality | 145 mOsm |
|  | 66 | Dextrose wall rinse solution | 5 liters |
|  |  | 50% Dextrose soln (B Braun) | 329 g |
|  |  | DI water to final volume of | 5 L |
|  |  | Osmolality | 148 mOsm |

Since only ½ the lipids and ½ the previous examples bupivacaine are processed per minute but the Dextrose Lysine (second aqueous) and Dextrose only (wall rinse) solutions are pumped at the normal rate, the concentration of bupivacaine MVLs out of the spray chamber (FIG. 1, component 50) will be ½ of that seen in the previous examples. A larger 1,000 mL sample was therefore taken for concentration and diafiltration as in the previous example. This sample was not heat treated.

TABLE 10

Analysis of the final decanted product MVLs are as follows:

| Bupi mg/ml | % free | PPV % | d10 | d50 | D90 |
|---|---|---|---|---|---|
| 15.21 | 1.1% | 71% | 9.3 | 22.5 | 55.5 |

The accelerated stability (30 C) plot for this low osmolality sample can be seen in FIG. 14. The low osmolality sample was significantly more stable than the not heat treated sample but less stable than the heat treated sample.

As seen in FIG. 15, the Rat in-vivo release profile of the low osmolality sample can be the most desirable as it has the lowest initial peak and the longest duration; highest blood concentrations at 72 and 96 hours. In this process, starting with a $1^{st}$ aqueous solution with an osmolality lower than the final MVL suspending solution was unexpectedly found to both increase MVL storage stability, reduce the initial in-vivo release peak and prolong the duration of bupivacaine delivery.

As can be seen from Table 10, this example produced a smaller particle size d50 than the previous examples. As can be seen from FIG. 14, the low osmolality sample, which was not heat treated, has a much better accelerated stability than the not heat treated sample of the previous example.

EXAMPLE 5

Solvent Exchange/Concentration

FIGS. 8, 10 and 11 depict example continuous buffer exchange and MVL concentration systems (seen in FIG. 1A and FIG. 1B, component 70) which are fed a MVL suspension from a solvent removal vessel (seen in FIG. 1A and FIG. 1B, component 50) by a solvent line (seen in FIG. 1A and FIG. 1B, component 120).

These systems take the continuous flow of MVL suspension produced in a solvent removal vessel (seen in FIG. 1A and FIG. 1B, component 50) and exchange the suspending buffer for another suspending medium (e.g. normal saline) and at the same time optionally concentrate the MVL suspension. In most cases it is desired to produce slightly over concentrated MVL suspensions in a retentate vessel (seen in FIG. 8, component 8300; FIG. 10, component 10500; and FIG. 11, component 11400). The lot is analyzed and sterilely diluted to exact concentration before filling into vials aseptically. The final concentration of the MVL is obtained by processing in two or more stages connected in series. Additionally, processing results in any percent of original suspending buffer removal.

These systems include medium supply source, such as a tank and a particle concentrating device. The particle concentrating device is a hollow fiber tangential flow filter (e.g. Model No. CFP-6-D-9A from Amersham Biosciences of Westborough, Mass.) or a continuous or semi-continuous centrifuge (Centritech Lab III or CARR ViaFuge Pilot from Pneumatic Scale Angelus Corp., Clearwater, Fla.) or any other device that separates the MVLs from the suspending medium.

The following constraints apply to analogous components of all the steady state stages of the continuous buffer exchange and MVL concentration systems:

In a continuous manner, the first stage of FIG. 8 consisting of components 8120, 8100, 8122, 8123, 8110, 8190, 8202, 8160, 8150, 8140, 8180, 8131, 8130, 8212 and 8170 will exchange the initial suspending buffer with normal saline.

In reference to FIG. 8, at steady state where a constant volume is in the tank, the input volume flows; MVL suspension in 8120 and saline in 8130 must equal the volume out flows; permeate 8160 and MVL suspension transferred to the next stage by metering pump 8123. This is done by controlling/fine adjusting any of the above 4 flow rates to keep the volume in the tank constant, e.g. saline fine adjustment valve 8212.

At steady state the mass or number of MVLs is conserved and thus the input rate of the number of MVLs, concentration times the flow rate, from pipe 8120 must equal the MVL outflow from 8122, again number concentration times flow rate. This means that if the volume outflow rate in 8122 is lower than the input volume flow rate in 8120, the concentration of MVLs in the tank 8100 and pipe 8122 rises until the MVL in matches the MVL out. This gives a MVL concentration factor, output MVL concentration divided by the input MVL concentration equal to the volume flow in MVL input pipe, 8120, divided by the volume flow in the output pipe, 8122.

The original buffer is diluted by saline at each stage. This dilution factor is the flow rate of buffer in to the tank, 8100, divided by the total of the volume flow rate of buffer in pipe 8120 and the volume flow rate of saline in pipe 8212. The MVLs take up appreciable volume and so the flow rate of buffer into the tank, 8100, is the volume flow rate in pipe 8120 times one minus the volume percentage of that suspension that is MVLs, (PPV %, Packed Particle Volume percentage).

Adhering to these constraints, the first 2 stages of FIG. 8, containing tanks 8100 and 8200 will reach steady state. The smaller the tanks, the faster the equilibration time and the lower the total holdup in the system. For the systems described in Examples 2 and 3, a tank volume of from 0.25 liter to 10 liters and preferably 0.75 liters is appropriate.

The third stage in FIG. 8 contains the final retentate vessel, 8300, and is large enough to hold one lot of product, e.g. 40 liters. As shown, the volume in final retentate vessel 8300 remains constant but the concentration is continuously rising as there is no MVL out flow, until it reaches the desired final concentration of MVLs. By choosing appropriate flow rates in pipes 8124, 8208 and 8164 this stage is alternatively run with a constant MVL concentration and rising volume.

When starting these systems, the systems are either started with each tank filled to the appropriate volume with saline or they are started empty and filled with the MVL suspension input and saline input but only start the output pump, e.g. 8123, and hollow fiber recirculation pump, e.g. 8110 when the tank for that stage fills to its desired volume. Likewise at the end of a lot, the MVL input line is switched to saline which moves all MVLs to the product tank, or the saline and MVL inputs and the hollow fiber recirculation pump is stopped to allow each tank to empty into the next until the lot is again all in the product vessel.

Flow rate and additional parameters for the system of FIG. 8 using the hollow fiber cartridge and filtration rates and MVL output rate of the 25 Hz Process, 30 Hz Process, or 35 Hz Process of Example 1 is given below:

TABLE 11

(flow rates are for fluid traveling through the components from FIG. 8)
concentration factor of 100% in 1st 2 stages (buffer exchange only)

| Stage | MVL suspension in | (mL/min) | Saline in | (mL/min) | MVL suspension out | (mL/min) | permeate | (mL/min) |
|---|---|---|---|---|---|---|---|---|
| 1 | 8120 | 165 | 8130 | 410 | 8122 | 165 | 8160 | 410 |
| 2 | 8122 | 165 | 8132 | 410 | 8124 | 165 | 8162 | 410 |
| 3 | 8124 | 165 | 8134 | 245 |  | 0 | 8164 | 410 |

| Stage | Net tank volume change |  | part conc. out | PPV % | Lysine dilution factor | % Lysine left | % exchanged |
|---|---|---|---|---|---|---|---|
|  | System 810 Input, 8120 >>> |  | 100% | 20.0% |  | 100% |  |
| 1 | 8100 | 0 | 100% | 20.0% | 0.2435 | 24.4% | 75.6% |
| 2 | 8200 | 0 | 100% | 20.0% | 0.2435 | 5.9% | 94.1% |
| 3 | 8300 | 0 | rising | rising | 0.3501 | 2.1% | 97.9% |

The flow rates in Table 11 result in buffer exchange only. The MVL PPV remains at 20% but the original buffer concentration is reduced by 99.7% with its concentration in the product being 2.1% of original. For comparison, a 4 volume batch diafiltration exchange as used in the examples, reduces the buffer concentration to 1.8% or 98.2% exchanged.

TABLE 12

(flow rates are for fluid traveling through the components from FIG. 8)
A total concentration factor of 200% in 1st 2 stages and buffer exchange

| Stage | MVL suspension in | (mL/min) | Saline in | (mL/min) | MVL suspension out | (mL/min) | permeate | (mL/min) |
|---|---|---|---|---|---|---|---|---|
| 1 | 8120 | 165 | 8130 | 369 | 8122 | 124 | 8160 | 410 |
| 2 | 8122 | 124 | 8132 | 396 | 8124 | 110 | 8162 | 410 |
| 3 | 8124 | 110 | 8134 | 300 |  | 0 | 8164 | 410 |

| Stage | Net tank volume change |  | Stage concentration factor | PPV % | Lysine dilution factor | % Lysine left | % exchanged |
|---|---|---|---|---|---|---|---|
|  | System 810 Input, 8120 >>> |  | 100% | 20.0% |  | 100% |  |
| 1 | 8100 | 0 | 133% | 26.6% | 0.2635 | 26.3% | 73.7% |
| 2 | 8200 | 0 | 150% | 40.0% | 0.1870 | 4.9% | 95.1% |
| 3 | 8300 | 0 | rising | rising | 0.1798 | 0.9% | 99.1% |

The flow rates in Table 12 result in buffer 99.1% exchanged down to 0.9% of the original concentration.

TABLE 13

(flow rates are for fluid traveling through the components from FIG. 11)
concentration factor of 300% in 3 stages and buffer exchange
Product is collected in Tank 11400 with volume rising at 114.3 mL/min

| Stage | MVL suspension in | (mL/min) | Saline | (mL/min) | MVL suspension out | (mL/min) | Supernatant out | (ml/min) |
|---|---|---|---|---|---|---|---|---|
| 1 | 11120 | 165 | 11130 | 949 | 11122 | 114.3 | 11160 | 1,000 |
| 2 | 11122 | 114 | 11132 | 1000 | 11124 | 114.3 | 11162 | 1,000 |
| 3 | 11124 | 114 | 11134 | 1000 | 11166 | 114.3 | 11164 | 1,000 |

TABLE 13-continued (flow rates are for fluid traveling through the components from FIG. 11)
concentration factor of 300% in 3 stages and buffer exchange
Product is collected in Tank 11400 with volume rising at 114.3 mL/min

| Stage | Net tank volume change | | Stage concentration factor | PPV % | Lysine dilution factor | % Lysine left | % exchanged |
|---|---|---|---|---|---|---|---|
| | System 1110 Input, 11120 >>> | | 100% | 20.0% | | 100% | |
| 1 | 11100 | 0 | 144% | 28.9% | 0.1221 | 12.2% | 87.8% |
| 2 | 11200 | 0 | 144% | 41.7% | 0.0752 | 0.9% | 99.1% |
| 3 | 1130 | 0 | 144% | 60.1% | 0.0625 | 0.1% | 99.9% |

The flow rates in Table 13 result in a concentration factor of 300% with the same input conditions used for Tables 11 and 12.

Systems can be assembled with any combination of hollow fiber cartridges and centrifuges. They can have two or three or more stages. With more stages the buffer is exchanged with less saline but there is more equipment to keep aseptic.

The semi-continuous centrifuges above, Centritech Lab III or CARR ViaFuge Pilot, are operated in an aseptic fashion. The semi-continuous centrifuges are capable of very high particle concentration factors e.g. 100 to 1 and can also discharge MVL concentrate up to 80% PPV %. The Centritech Lab III is semi-continuous as it has a constant feed with an intermittent concentrate discharge, every 10 seconds to 2 minutes. The ViaFuge Pilot has a constant feed which is interrupted every 2 to 10 minutes by a rapid discharge cycle.

FIG. 10 depicts continuous buffer exchange and MVL concentration systems where the hollow fiber filters operate at lower particle concentrations, a condition where they have higher permeate rates. The centrifuge (seen in FIG. 10, component 10400), e.g. CARR ViaFuge Pilot, is used to do a final concentration into the final product vessel (seen in FIG. 10, component 10500). In this system all three stages including the tanks (seen in FIG. 10, components 10100, 10200 and 10300) run at both constant volume and MVL concentration while the final tank (seen in FIG. 10, component 10500) collects the concentrated buffer exchanged MVL suspension.

FIG. 11 depicts a system for continuous buffer exchange and MVL concentration including only centrifuges. Using typical process rates for the ViaFuge Pilot and the same feed conditions as the hollow fiber system, provides a system that exchanges 99.9% of the buffer while concentrating the MVL suspension by a factor of 3 when using the parameters from Table 13. The saline inputs should only flow when the input MVL stream is flowing.

Any tanks connected to these centrifuges must be large enough to accommodate the intermittent nature of the centrifuge input and output.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A continuous processing system, comprising:

a first concentrator unit comprising:
- a first retentate vessel;
- a first particle suspension inlet line, connected to the first retentate vessel;
- a first outlet line, connecting the first retentate vessel and a first hollow fiber tangential flow filter;
- a first solution inlet line;
- a first sterilizing hydrophilic filter, connecting the first retentate vessel and the first solution inlet line;
- a first pump located along the first outlet line between the first retentate vessel and the first hollow fiber tangential flow filter;
- a second outlet line, leading to a second concentrator unit, said second concentrator unit comprising:
- a second retentate vessel;
- a second particle suspension inlet line, connected to the second retentate vessel and the second outlet line;
- a third outlet line, connecting the second retentate vessel and a second hollow fiber tangential flow filter;
- a second solution inlet line;
- a second sterilizing hydrophilic filter, connecting the second retentate vessel and the second solution inlet line; and
- a second pump located along the third outlet line between the second retentate vessel and the second hollow fiber tangential flow filter.

2. The system of claim 1, further comprising a new suspending medium inlet line connected to the first retentate vessel.

3. The system of claim 1, wherein the continuous processing system is a continuous-flow particle-concentration system or continuous phase exchange system.

4. The system of claim 1, further comprising an evaporation apparatus, connected to the first particle suspension inlet line, wherein the evaporation apparatus comprises:

at least one atomizing nozzle apparatus and a solvent removal vessel having a top, a bottom and a circular wall for removing an organic solvent from a droplet, wherein at least one atomizing nozzle apparatus comprises:
- a first fluid conduit and a second fluid conduit each having at least one entrance orifice and at least one exit orifice;
- a fluid contacting chamber having a top comprising at least one entrance orifice and having a bottom comprising at least one exit orifice and connecting to the at least one exit orifice of the first fluid conduit and the at least one exit orifice of the second fluid conduit; and a third fluid conduit, wherein the third fluid conduit annularly surrounds a portion of the fluid contacting chamber, and wherein the solvent removal chamber comprises:

a carrier gas entrance orifice;

a solvent removal gas exit orifice centrally connected to the top; and a product exit orifice connected to the bottom of the solvent removal vessel.

5. The system of claim 4, wherein the at least one exit orifice of the fluid contacting chamber and the at least one exit orifice of the third fluid conduit are flush.

6. The system of claim 4, wherein the at least one exit orifice of the fluid contacting chamber is recessed within the at least one exit orifice of the third fluid conduit.

7. The system of claim 4, wherein the at least one exit orifice of the fluid contacting chamber extends beyond the at least one exit orifice of the third fluid conduit.

8. The system of claim 4, wherein the first fluid conduit and the second fluid conduit are co-axial for a first portion of the first fluid conduit length.

9. The system of claim 4, wherein the second fluid conduit annularly surrounds a first portion of the first fluid conduit.

10. The system of claim 4, wherein a diameter of the fluid contacting chamber is larger than a diameter of the first fluid conduit.

11. The system of claim 4, wherein the fluid contacting chamber conically narrows in diameter from the top of the fluid contacting chamber to the bottom of the fluid contacting chamber.

12. The system of claim 4, wherein the fluid contacting chamber conically narrows in diameter from a point below the top of the fluid contacting chamber to the bottom of the fluid contacting chamber.

13. The system of claim 4, wherein the at least one exit orifice of the first fluid conduit and the at least one exit orifice of the second fluid conduit are flush with each other.

14. The system of claim 4, wherein the atomizing nozzle is mounted to and extending through the top of the solvent removal vessel.

15. The system of claim 4, further comprising a rinse nozzle mounted to and extending through the top of the solvent removal vessel.

16. The system of claim 4, wherein the circular wall has a central axis and the solvent removal gas exit orifice further comprises a tube extending into the solvent removal vessel residing along the central axis.

17. The system of claim 4, wherein the solvent removal gas exit orifice further comprises a tube extending into the solvent removal vessel, wherein the tube is fitted with a narrowing cone.

18. The system of claim 4, wherein the solvent removal gas exit orifice further comprises a tube extending into the solvent removal vessel, wherein the tube is fitted with a narrowing cone and an annular ring.

19. The system of claim 4, wherein the solvent removal gas exit orifice diameter is less than $1/10$ of a diameter of the inside of the solvent removal vessel wall.

* * * * *